United States Patent
Niimi et al.

(10) Patent No.: US 11,732,311 B2
(45) Date of Patent: Aug. 22, 2023

(54) TM MAPPING METHOD

(71) Applicant: National University Corporation University of Toyama, Toyama (JP)

(72) Inventors: Hideki Niimi, Toyama (JP); Shinya Otsuki, Toyama (JP); Isao Kitajima, Toyama (JP)

(73) Assignee: National University Corporation University of Toyama

( * ) Notice: Subject to any disclaimer, the term of this patent is extended or adjusted under 35 U.S.C. 154(b) by 338 days.

(21) Appl. No.: 16/906,115

(22) Filed: Jun. 19, 2020

(65) Prior Publication Data

US 2021/0032686 A1 Feb. 4, 2021

Related U.S. Application Data

(63) Continuation of application No. PCT/JP2018/023382, filed on Jun. 20, 2018.

(30) Foreign Application Priority Data

Dec. 20, 2017 (JP) .................................. 2017-244461

(51) Int. Cl.
*C12Q 1/689* (2018.01)
*G16B 30/00* (2019.01)

(52) U.S. Cl.
CPC ............. *C12Q 1/689* (2013.01); *G16B 30/00* (2019.02)

(58) Field of Classification Search
None
See application file for complete search history.

(56) References Cited

U.S. PATENT DOCUMENTS

| | | |
|---|---|---|
| 8,323,898 B2 | 12/2012 | Niimi et al. |
| 9,243,272 B2 | 1/2016 | Tabata et al. |
| 10,501,813 B2 | 12/2019 | Tabata et al. |
| 2012/0282611 A1* | 11/2012 | Wangh ................ C12Q 1/6858 435/6.11 |
| 2016/0257999 A1 | 9/2016 | Tabata et al. |

FOREIGN PATENT DOCUMENTS

| | | |
|---|---|---|
| WO | 2007/097323 A1 | 8/2007 |
| WO | 2010/082640 A1 | 7/2010 |

OTHER PUBLICATIONS

Niimi, "Development of the Novel Method for Detecting and Identifying Pathogenic Bacteria Directly From Whole Blood Samples", Antibiotics & Chemotherapy, vol. 31, S-1, pp. 1089-1097, 2015 (19 pages including partial English Translation).

Niimi, "System for Quickly Identifying Sepsis Pathogenic Bacteria So as to Achieve Immediate Report of Bloodstream Infection Symptoms (BSI): Melting Temperature (Tm) Mapping Method", Clinical Microbiology, , vol. 44, No. 5, pp. 447-455, Sep. 2017 (16 pages with partial English Translation).

Chakravorty et al., "Rapid Universal Identification of Bacterial Pathogens from Clinical Cultures by Using a Novel Sloppy Molecular Beacon Melting Temperature Signature Technique." Journal of Clinical Microbiology, vol. 48, No. 1, pp. 258-267, Jan. 2010.

Otsuki, "Melting Temperature Mapping Method Using Imperfect-Match Linear Long Probes" posted to https://toyama.repo.nii.ac.jp/ on Jun. 22, 2017 (13 pages, including partial English translation).

* cited by examiner

*Primary Examiner* — Teresa E Strzelecka

(74) *Attorney, Agent, or Firm* — Harness, Dickey & Pierce, P.L.C.

(57) ABSTRACT

The improved Tm mapping method using imperfect-match linear long quenching probes can accurately distinguish among and identify microorganisms at least at the genus level and often at the species level even in a real-time PCR instrument having measurement errors of Tm values between PCR tubes within ±0.5° C. Therefore, the Tm mapping method can be performed in almost all real-time PCR instruments and can identify unspecified infection-causing pathogenic microorganisms in about 4 hours after sample collection.

7 Claims, 44 Drawing Sheets

Specification includes a Sequence Listing.

| IMLL Q-PROBE | BINDS TO | PCR AMPLIFIED PRODUCT | BINDING SITE* (PROBE LENGTH: BP) |
|---|---|---|---|
| PROBE 1-1 | → | REGION 1 AMPLIFIED PRODUCT | 84 – 126 (44) |
| PROBE 1-2 | → | REGION 1 AMPLIFIED PRODUCT | 193 – 230 (38) |
| PROBE 2-1 | → | REGION 2 AMPLIFIED PRODUCT | 335 – 379 (45) |
| PROBE 3-1 | → | REGION 3 AMPLIFIED PRODUCT | 503 – 543 (41) |
| PROBE 3-2 | → | REGION 3 AMPLIFIED PRODUCT | 557 – 600 (44) |
| PROBE 4-1 | → | REGION 4 AMPLIFIED PRODUCT | 776 – 813 (38) |
| PROBE 5 | → | REGION 5 AMPLIFIED PRODUCT | 949 – 990 (42) |

*: *Escherichia coli* 16S ribosomal RNA (Accession No. AB548582)

IMLL PROBE 1-2 (MISMATCHED SEQUENCES ARE UNDERLINED)

(5' →3')

| | |
|---|---|
| BASE SEQUENCE OF IMLL PROBE 1-1 | GCCATCGGATGTGCCCAGATAAGATTAGCTAGTAGGTG |
| *Acinetobacter baumanii* | GCTAATAGATGAGCCTAAGTCGGATTAGCTAGTTGGTG |
| *Acinetobacter calcoaceticus* | GCTAATAGATGAGCCTAAGTCGGATTAGCTAGTTGGTG |
| *Actinomyces israelii* | GCCGCATGGTGTGGCTGGGAAAGATTCACTTTTGTGGTG |
| *Aeromonas hydrophila* | GCGATTGGATATGCCCAGGTGGGATTAGCTAGTTGGTG |
| *Arthrobacter cumminsii* | GTTATCCGGAATTATTGGGCGTAAAGAGCTCGTAGGCG |
| *Bacillus cereus* | ACTTATGGATGGACCCGCGTCGCATTAGCTAGTTGGTG |
| *Bacteroides fragilis* | GGTAAAGGATGGGGATGCGTTCCATTAGGTTGTTGGTG |
| *Bacteroides nordii* | GGTAAAAGATGGGGATGCGTTCCATTAGGCAGTTGGCG |
| *Bacteroides thetaiotaomicron* | GTTATCGGATGGGGATGCGTTCCATTAGGCAGTTGGTG |
| *Bifidobacterium bifidum* | GGCGTGGGATGGGGTCGCGTCCTATCAGCTTGTTGGTG |
| *Bilophila wadsworthia* | GCTTAAGGATGAGTCCGCGTCCCATTAGCTAGTTGGCG |
| *Chryseobacterium gleum* | GGATAGAGATGGGCACGCGCAAGATTAGATAGTTGGTG |
| *Citrobacter amalonaticus* | GCCATCGGATGTGCCCAGATGGGATTAGCTAGTTGGTG |
| *Citrobacter freundii* | GCCATCGGATGTGCCCAGATGGGATTAGCTAGTAGGTG |
| *Clostridium difficile* | AGTACAGGATGGACCCGCGTCTGATTAGCTAGTTGGTA |

FIG. 8A

| | |
|---|---|
| *Clostridium hylemonae* | GGTGTAAGATGGGCCCGCGTCT GATTAGGTAGTTGGTA |
| *Clostridium leptum* | GCTCTGAGATGAGCTCGCGTCT GATTAGCTAGTTGGTC |
| *Corynebacterium striatum* | GGTGCAAGATGAGCTCGCGGCC TATCAGCTTGTTGGTG |
| *Eggerthella lenta* | GGCAAGGATGGGGTCGCGGC CCATTAGGTAGTAGGCG |
| *Eikenella corrodens* | GTTATTCGAGCGGCCGATAACT GATTAGCTAGTTGGTG |
| *Enterobacter aerogenes* | GCCATCAGATGTGCCCAGATGG GATTAGCTAGTAGGTG |
| *Enterobacter cloacae* | GCCATCAGATGTGCCCAGATGG GATTAGCTAGTAGGTG |
| *Enterococcus avium* | ACTGATGGATGGACCCGCGGTG CATTAGCTAGTTGGTG |
| *Enterococcus casseliflavus* | ACTGATGGATGGACCCGCGGTG CATTAGCTAGTTGGTG |
| *Enterococcus faecalis* | GCTGATGGATGGACCCGCGGTG CATTAGCTAGTTGGTG |
| *Enterococcus faecium* | GCTGATGGATGGACCCGCGGTG CATTAGCTAGTTGGTG |
| *Escherichia albertii* | GCCATCGGATGTGCCCAGATGG GATTAGCTTGTTGGTG |
| *Escherichia coli* | GCCATCGGATGTGCCCAGATGG GATTAGCTAGTAGGTG |
| *Finegoldia magna* | GTCAT−AGATGGGCTCGCGTCT GATTAGCTAGTTGGTG |
| *Fusobacterium necrophorum* | GCTAAGAGAGCTTTGCGTCC CATTAGCTAGTTGGTG |
| *Gardnerella vaginalis* | GGCATGGGATGGGGTCGCGTCC TATCAGCTTGTAGCTG |

FIG. 8B

| | |
|---|---|
| *Gemella morbillorum* | ACTATGAGATGGCTTTGCGGTG CATTAGCTAGTTGGTG |
| *Haemophilus influenzae* | GCCATAGGATGAGCCCAAGTGG GATTAGGTAGTTGGTG |
| *Halomonas venusta* | GCTATTGGATGAGCCTATGTCG GATTAGCTAGTTGGTG |
| *Klebsiella oxytoca* | GCCATCGGATGTGCCCAGATGG GATTAGCTTGTAGGTG |
| *Klebsiella pneumoniae* | GCCATCAGATGTGCCCAGATGG GATTAGCTAGTAGGTG |
| *Lactobacillus crispatus* | GCTATGGGATGGCCCCGCGGTG CATTAGCTAGTTGGTA |
| *Lactobacillus jensenii* | GCTAAAGGATGGACCTGCGATG CATTAGCTAGTTGGTA |
| *Lactococcus garvieae* | ACTACTTGATGATCCCGCGTTG TATTAGCTAGTTGGTA |
| *Listeria monocytogenes* | GCTTACAGATGGGCCCGCGGTG CATTAGCTAGTTGGTA |
| *Morganella morganii* | GCCATCAGATGAACCCATATGG GATTAGCTAGTAGGTG |
| *Mycoplasma hominis* | ACTAAAGATGAGGGTGCGGAA CATTAGTTAGTTGGTG |
| *Nocardia cyriacigeorgica* | GGTGCGAGATGGGCCCGCGGC CTATCAGCTTGTTGGTG |
| *Odoribacter splanchnicus* | GGTATCGGATGGGCATGCGTCC TATTAGTTAGTTGGCG |
| *Parvimonas micra* | GGTGTAAGAAGGGCTCGCGTCT GATTAGCTAGTTGGAA |
| *Pasteurella multocida* | GCCATAAGATGAGCCCAAGTGG GATTAGGTAGTTGGTG |
| *Prevotella corporis* | GGTATGGGATGGGGATGCGTCT GATTAGCTTGTTGGCG |

FIG. 8C

| | |
|---|---|
| *Prevotella intermedia* | GGTGGAGGATGGGGATGCGTCT GATTAGCTTGTTGGTG |
| *Propionibacterium acnes* | GCTTTCGCCTGTGACGAAGCGT GAGTGACGGTAATGGG |
| *Proteus mirabilis* | ACTATCGGATGAACCCATATGG GATTAGCTAGTAGGTG |
| *Pseudomonas aeruginosa* | GCTATCAGATGAGCCTAGGTCG GATTAGCTAGTTGGTG |
| *Raoultella planticola* | GCCATCAGATGTGCCCAGATGG GATTAGCTAGTAGGTG |
| *Salmonella enterica* | GCCATCAGATGTGCCCAGATGG GATTAGCTTGTTGGTG |
| *Serratia marcescens* | GCCATCAGATGTGCCCAGATGG GATTAGCTAGTAGGTG |
| *Sphingomonas paucimobilis* | GCCTGAGGATGAGCCCGCGTTG GATTAGGTAGTTGGTG |
| *Staphylococcus aureus* | ACTTATAGATGGATCCGCGCTG CATTAGCTAGTTGGTA |
| *Staphylococcus capitis/epidermidis* | ACTTATAGATGGATCCGCGCCG CATTAGCTAGTTGGTA |
| *Staphylococcus cohnii* | ACTTATAGATGGACCCGCGCCG TATTAGCTAGTTGGTA |
| *Staphylococcus haemolyticus* | ACTTATAGATGGACCCGCGCCG TATTAGCTAGTTGGTA |
| *Staphylococcus hominis* | ACTTATAGATGGACCTGCGCCG TATTAGCTAGTTGGTA |
| *Staphylococcus lugdunensis* | ACTTATAGATGGACCCGCGCCG TATTAGCTAGTTGGTG |
| *Stenotrophomonas maltophilia* | GCGATTGAATGAGCCGATGTCG GATTAGCTAGTTGGCG |
| *Streptococcus agalactiae* | ACTGTGAGATGGACCTGCGTTG TATTAGCTAGTTGGTG |

FIG. 8D

| | |
|---|---|
| *Streptococcus anginosus* | GCTAGTAGATGGACCTGCGTTG TATTAGCTAGTAGGTA |
| *Streptococcus constellatus* | ACTACCAGATGGACCTGCGTTG TATTAGCTAGTTGGTG |
| *Streptococcus dysgalactiae* | ACTATGAGATGGACCTGCGTTG TATTAGCTAGTTGGTG |
| *Streptococcus gordonii* | ACTACCAGATGGACCTGCGTTG TATTAGCTAGTAGGTG |
| *Streptococcus mitis* | ACTACCAGATGGACCTGCGTTG TATTAGCTAGTTGGTG |
| *Streptococcus pneumoniae* | ACTACCAGATGGACCTGCGTTG TATTAGCTAGTTGGTG |
| *Streptococcus pyogenes* | ACTATGAGATGGACCTGCGTTG TATTAGCTAGTTGGTG |
| *Streptococcus salivarius* | ACTACAAGATGGACCTGCGTTG TATTAGCTAGTAGGTG |

FIG. 8E

TABLE 1　　　　　　　　　　　　　　　　　　　D: DIFFERENCE VALUE

| THERMAL VARIATION OF INSTRUMENT | ±0.1℃ | ±0.2℃ | ±0.3℃ | ±0.4℃ | ±0.5℃ | ±0.6℃ |
|---|---|---|---|---|---|---|
| ERROR RANGE OF DIFFERENCE VALUE THAT IDENTICAL MICROORGANISM MAY HAVE | 0 ≤ D ≤ 0.28 | 0.28 < D ≤ 0.53 | 0.53 < D ≤ 0.80 | 0.80 < D ≤ 1.06 | 1.06 < D ≤ 1.33 | 1.33 < D ≤ 1.59 |

| BACTERIAL SPECIES REGISTERED IN DATABASE | NUMBER OF SIMILAR BACTERIAL SPECIES | | | | | | | MOST SIMILAR BACTERIAL SPECIES IN DATABASE (Difference Value) |
|---|---|---|---|---|---|---|---|---|
| | 0 ≤ D ≤ 0.28 | 0.28 < D ≤ 0.53 | 0.53 < D ≤ 0.80 | 0.80 < D ≤ 1.06 | 1.06 < D ≤ 1.33 | 1.33 < D ≤ 1.59 | 1.59 < D | |
| Acinetobacter baumanii | 0 | 0 | 0 | 0 | 0 | 0 | 70 | A. calcoaceticus (1.99) |
| Acinetobacter calcoaceticus | 0 | 0 | 0 | 0 | 0 | 0 | 70 | A. baumanii (1.99) |
| Actinomyces israelii | 0 | 0 | 0 | 0 | 0 | 0 | 70 | C. striatum (6.15) |
| Aeromonas hydrophilla | 0 | 0 | 0 | 0 | 0 | 0 | 70 | P. aeruginosa (8.56) |
| Arthrobacter cumminsii | 0 | 0 | 0 | 0 | 0 | 0 | 70 | P. micra (4.48) |
| Bacillus cereus | 0 | 0 | 0 | 0 | 0 | 0 | 70 | S. capitis/epidermidis (4.46) |
| Bacteroides fragilis | 0 | 0 | 0 | 0 | 0 | 1 | 69 | B. thetaiotaomicron (1.48) |
| Bacteroides nordii | 0 | 0 | 0 | 0 | 0 | 0 | 70 | B. fragilis (5.16) |
| Bacteroides thetaiotaomicron | 0 | 0 | 0 | 0 | 0 | 1 | 69 | B. fragilis (1.48) |
| Bifidobacterium bifidum | 0 | 0 | 0 | 0 | 0 | 0 | 70 | N. cyriacigeorgica (4.54) |
| Bilophila wadsworthia | 0 | 0 | 0 | 0 | 0 | 0 | 70 | P. micra (8.45) |
| Chryseobacterium gleum | 0 | 0 | 0 | 0 | 0 | 0 | 70 | P. micra (5.15) |

FIG 9A

| BACTERIAL SPECIES REGISTERED IN DATABASE | NUMBER OF SIMILAR BACTERIAL SPECIES | | | | | | | MOST SIMILAR BACTERIAL SPECIES IN DATABASE (Difference Value) |
|---|---|---|---|---|---|---|---|---|
| | 0 ≤ D ≤ 0.28 | 0.28 < D ≤ 0.53 | 0.53 < D ≤ 0.80 | 0.80 < D ≤ 1.06 | 1.06 < D ≤ 1.33 | 1.33 < D ≤ 1.59 | 1.59 < D | |
| Citrobacter amalonaticus | 0 | 0 | 0 | 0 | 0 | 2 | 68 | K. pneumoniae (1.52) |
| Citrobacter freundii | 0 | 0 | 0 | 0 | 0 | 0 | 70 | E. aerogenes (1.63) |
| Clostridium difficile | 0 | 0 | 0 | 0 | 0 | 0 | 70 | H. influenzae (11.48) |
| Clostridium hylemonae | 1 | 0 | 0 | 0 | 0 | 0 | 69 | C. leptum (0.17) |
| Clostridium leptum | 1 | 0 | 0 | 0 | 0 | 0 | 69 | C. hylemonae (0.17) |
| Corynebacterium striatum | 0 | 0 | 0 | 0 | 0 | 0 | 70 | S. maltophilia (10.74) |
| Eggerthella lenta | 0 | 0 | 0 | 0 | 0 | 0 | 70 | N. cyriacigeorgica (4.69) |
| Eikenella corrodens | 0 | 0 | 0 | 0 | 0 | 0 | 70 | S. maltophilia (10.24) |
| Enterobacter aerogenes | 1 | 0 | 0 | 0 | 0 | 0 | 69 | E. cloacae (0.12) |
| Enterobacter cloacae | 1 | 0 | 0 | 0 | 0 | 0 | 69 | E. aerogenes (0.12) |
| Enterococcus avium | 0 | 0 | 0 | 0 | 0 | 0 | 70 | E. casseliflavus (2.74) |
| Enterococcus casseliflavus | 0 | 0 | 0 | 0 | 0 | 0 | 70 | E. faecalis (0.3) |
| Enterococcus faecalis | 1 | 0 | 0 | 0 | 0 | 0 | 69 | E. faecium (0.11) |
| Enterococcus faecium | 1 | 0 | 0 | 0 | 0 | 0 | 69 | E. faecalis (0.41) |
| Escherichia albertii | 0 | 0 | 0 | 0 | 0 | 0 | 70 | K. pneumoniae (4.65) |
| Escherichia coli | 0 | 0 | 0 | 0 | 0 | 0 | 70 | E. albertii (6.09) |
| Finegoldia magna | 0 | 0 | 0 | 0 | 0 | 0 | 70 | P. mirabilis (4.44) |
| Fusobacterium nucleatum | 0 | 0 | 0 | 0 | 0 | 0 | 70 | None |
| Gardnerella vaginalis | 0 | 0 | 0 | 0 | 0 | 0 | 70 | C. striatum (5.88) |

FIG 9B

| BACTERIAL SPECIES REGISTERED IN DATABASE | NUMBER OF SIMILAR BACTERIAL SPECIES | | | | | | | MOST SIMILAR BACTERIAL SPECIES IN DATABASE (Difference Value) |
|---|---|---|---|---|---|---|---|---|
| | $0 \leq D \leq 0.28$ | $0.28 < D \leq 0.53$ | $0.53 < D \leq 0.80$ | $0.80 < D \leq 1.06$ | $1.06 < D \leq 1.33$ | $1.33 < D \leq 1.59$ | $1.59 < D$ | |
| Gemella morbillorum | 0 | 0 | 0 | 0 | 0 | 0 | 70 | L. crispatus (5.26) |
| Haemophilus influenzae | 0 | 0 | 0 | 0 | 0 | 0 | 70 | P. mirabilis (8.07) |
| Halomonas venusta | 0 | 0 | 0 | 0 | 0 | 0 | 70 | A. calcoaceticus (6.14) |
| Klebsiella oxytoca | 0 | 0 | 0 | 0 | 0 | 1 | 69 | C. amalonaticus (1.55) |
| Klebsiella pneumoniae | 0 | 0 | 0 | 0 | 0 | 1 | 69 | C. amalonaticus (1.52) |
| Lactobacillus crispatus | 0 | 0 | 0 | 0 | 0 | 0 | 70 | L. monocytogenes (4.96) |
| Lactobacillus jensenii | 0 | 0 | 0 | 0 | 0 | 0 | 70 | S. aureus (2.22) |
| Lactococcus garvieae | 0 | 0 | 0 | 0 | 0 | 0 | 70 | S. gordonii (3.49) |
| Listeria monocytogenes | 0 | 0 | 0 | 0 | 0 | 0 | 70 | E. faecium (4.86) |
| Morganella morganii | 0 | 0 | 0 | 0 | 0 | 0 | 70 | P. mirabilis (10.39) |
| Mycoplasma hominis | 0 | 0 | 0 | 0 | 0 | 0 | 70 | E. avium (5.54) |
| Nocardia cyriacigeorgica | 0 | 0 | 0 | 0 | 0 | 0 | 70 | None |
| Odoribacter splanchnicus | 0 | 0 | 0 | 0 | 0 | 0 | 70 | None |
| Parvimonas micra | 0 | 0 | 0 | 0 | 0 | 0 | 70 | A. cumminsii (5.07) |
| Pasteurella multocida | 0 | 0 | 0 | 0 | 0 | 0 | 70 | P. aeruginosa (7.71) |
| Prevotella corporis | 0 | 0 | 0 | 0 | 0 | 0 | 70 | B. nordii (9.60) |
| Prevotella intermedia | 0 | 0 | 0 | 0 | 0 | 0 | 70 | S. maltophilia (10.36) |
| Propionibacterium acnes | 0 | 0 | 0 | 0 | 0 | 0 | 70 | N. cyriacigeorgica (10.28) |
| Proteus mirabilis | 0 | 0 | 0 | 0 | 0 | 0 | 70 | F. magna (4.44) |

FIG. 9C

| BACTERIAL SPECIES REGISTERED IN DATABASE | NUMBER OF SIMILAR BACTERIAL SPECIES | | | | | | | MOST SIMILAR BACTERIAL SPECIES IN DATABASE (Difference Value) |
|---|---|---|---|---|---|---|---|---|
| | $0 \le D \le 0.28$ | $0.28 < D \le 0.53$ | $0.53 < D \le 0.80$ | $0.80 < D \le 1.06$ | $1.06 < D \le 1.33$ | $1.33 < D \le 1.59$ | $1.59 < D$ | |
| Pseudomonas aeruginosa | 0 | 0 | 0 | 0 | 0 | 0 | 70 | A. calcoaceticus (6.41) |
| Raoultella planticola | 0 | 0 | 0 | 0 | 0 | 0 | 70 | S. marcescens (3.09) |
| Salmonella enterica | 0 | 0 | 0 | 0 | 0 | 0 | 70 | K. pneumoniae (4.25) |
| Serratia marcescens | 0 | 0 | 0 | 0 | 0 | 0 | 70 | R. planticola (3.09) |
| Sphingomonas paucimobilis | 0 | 0 | 0 | 0 | 0 | 0 | 70 | A. hydrophila (10.59) |
| Staphylococcus aureus | 3 | 0 | 1 | 1 | 0 | 0 | 65 | S. hemolyticus (0.16) |
| Staphylococcus capitis/epidermidis | 0 | 1 | 3 | 0 | 0 | 1 | 65 | S. lugdunensis (0.48) |
| Staphylococcus cohnii | 0 | 0 | 0 | 3 | 1 | 1 | 65 | S. haemolyticus (0.96) |
| Staphylococcus hemolyticus | 3 | 0 | 1 | 1 | 0 | 0 | 65 | S. aureus (0.16) |
| Staphylococcus hominis | 3 | 0 | 1 | 1 | 0 | 0 | 65 | S. lugdunensis (0.10) |
| Staphylococcus lugdunensis | 3 | 1 | 0 | 0 | 1 | 0 | 65 | S. hominis (0.10) |
| Stenotrophomonas maltophilia | 0 | 0 | 0 | 0 | 0 | 0 | 70 | C. striatum (10.74) |
| Streptococcus agalactiae | 0 | 0 | 0 | 0 | 0 | 0 | 70 | S. pyogenes (4.59) |
| Streptococcus anginosus | 0 | 0 | 0 | 0 | 0 | 0 | 70 | S. pyogenes (2.85) |
| Streptococcus constellatus | 0 | 0 | 0 | 0 | 0 | 0 | 70 | S. salivarius (2.27) |
| Streptococcus dysgalactiae | 0 | 0 | 0 | 0 | 0 | 0 | 70 | S. mitis (2.45) |
| Streptococcus gordnii | 0 | 0 | 0 | 0 | 0 | 0 | 70 | E. faecium (3.24) |
| Streptococcus mitis | 0 | 0 | 0 | 0 | 0 | 0 | 70 | S. dysgalactiae (2.45) |

FIG. 9D

| BACTERIAL SPECIES REGISTERED IN DATABASE | NUMBER OF SIMILAR BACTERIAL SPECIES | | | | | | | MOST SIMILAR BACTERIAL SPECIES IN DATABASE (Difference Value) |
|---|---|---|---|---|---|---|---|---|
| | 0 ≤ D ≤ 0.28 | 0.28 < D ≤ 0.53 | 0.53 < D ≤ 0.80 | 0.80 < D ≤ 1.06 | 1.06 < D ≤ 1.33 | 1.33 < D ≤ 1.59 | 1.59 < D | |
| Streptococcus pneumoniae | 0 | 0 | 0 | 0 | 0 | 0 | 70 | S. mitis (5.52) |
| Streptococcus pyogenes | 0 | 0 | 0 | 0 | 0 | 0 | 70 | S. anginosus (2.85) |
| Streptococcus salivarius | 0 | 0 | 0 | 0 | 0 | 0 | 70 | S. constellatus (2.27) |

FIG. 9E

TABLE 2

| IDENTIFICATION RESULTS | | | | CONSISTENCY | | COMMENTS |
|---|---|---|---|---|---|---|
| IMPROVED TM MAPPING METHOD USING 1MLL PROBES | DIFF. | CONVENTIONAL BLOOD CULTURE METHOD | SEQUENCING | CULTURE | SEQ. | |

CONTROL: BLOOD FROM HEALTHY SUBJECTS

| | | | | | | |
|---|---|---|---|---|---|---|
| NO DETECTION OF MICROORGANISMS | - | NEGATIVE IN BLOOD CULTURE METHOD | | - | - | NEGATIVE CONTROL |

PATIENTS WITH SEPSIS

| # | | | | | | |
|---|---|---|---|---|---|---|
| 1 | Klebsiella pneumoniae | 0.05 | Staphylococcus epidermidis | | YES | - |
| 2 | Enterobacter aerogenes | 0.16 | Enterobacter aerogenes | | YES | - |
| 3 | Pseudomonas aeruginosa | 0.16 | Pseudomonas aeruginosa | | YES | - |
| 4 | Escherichia coli | 0.22 | Escherichia coli | | YES | - |
| 5 | Escherichia coli | 0.23 | Escherichia coli | | YES | - |
| 6 | genus Staphylococcus (S. aureus) | 0.23 | Staphylococcus aureus | | YES | - | SHORT PROBE FOR DETECTING S. AUREUS WAS ADDITIONALLY USED |

DIFF. = DIFFERENCE VALUE
SEQ. = IDENTIFICATION RESULT FROM SEQUENCING
-: NO BLOOD CULTURE OR SEQUENCING

FIG. 10A

IDENTIFICATION RESULTS

| | IMPROVED TM MAPPING METHOD USING IMLL PROBES | DIFF. | CONVENTIONAL BLOOD CULTURE METHOD | SEQUENCING | CONSISTENCY CULTURE | CONSISTENCY SEQ. | COMMENTS |
|---|---|---|---|---|---|---|---|
| PATIENTS WITH SEPSIS | | | | | | | |
| 7 | Klebsiella pneumoniae | 0.27 | Klebsiella pneumoniae | | YES | — | |
| 8 | Staphylococcus capitis / epidermidis | 0.28 | coagulase negative Staphylococcus (CNS) | Staphylococcus epidermidis | — | YES | SHORT PROBE FOR DETECTING S. AUREUS WAS ADDITIONALLY USED |
| 9 | genus Staphylococcus (CNS) | 0.28 | coagulase negative Staphylococcus (CNS) | Staphylococcus caprae | YES | YES | |
| 10 | Bacillus cereus | 0.31 | Bacillus cereus | | YES | — | |
| 11 | Proteus mirabilis | 0.31 | Proteus mirabilis | | YES | — | |
| 12 | Klebsiella pneumoniae | 0.33 | Klebsiella pneumoniae | | YES | — | |
| 13 | Escherichia coli | 0.35 | Escherichia coli | | YES | — | |
| 14 | Haemophilus influenzae | 0.50 | Haemophilus influenzae Klebsiella oxytoca Streptococcus pneumoniae | Haemophilus influenzae | YES | YES | ONLY NUMERICALLY DOMINANT MICROORGANISMS WERE DETECTED |

DIFF. = DIFFERENCE VALUE
SEQ. = IDENTIFICATION RESULT FROM SEQUENCING
—: NO BLOOD CULTURE OR SEQUENCING

FIG. 10B

TABLE 3-1
BLIND TEST PERFORMED BY USING IMPROVED Tm MAPPING METHOD WITH IML PROBES (IN REAL-TIME PCR INSTRUMENT WITH THERMAL VARIATION OF ± 0.4°C)

| No. | BACTERIAL DNA USED | IDENTIFICATION RESULTS | DIFF. | CONSISTENCY OF RESULTS SPECIES LEVEL | CONSISTENCY OF RESULTS GENUS LEVEL | SECOND MOST SIMILAR MICROORGANISM IN IDENTIFICATION RESULT (DIFF.) | SPECIFICITY IN DATABASE (Difference Value ≦ 0.8) |
|---|---|---|---|---|---|---|---|
| 1 | Achromobacter xylosoxidans | Achromobacter xylosoxidans | 0.41 | ○ | ○ | Bordetella pertussis (5.81) | |
| 2 | Acinetobacter baumannii | Acinetobacter baumannii | 0.33 | ○ | ○ | Acinetobacter calcoaceticus (2.25) | |
| 3 | Acinetobacter calcoaceticus | Acinetobacter calcoaceticus | 0.36 | ○ | ○ | Acinetobacter baumannii (2.26) | |
| 4 | Aeromonas hydrophila | Aeromonas hydrophila | 0.55 | ○ | ○ | Aeromonas sobria (3.09) | |
| 5 | Alistipes onderdonkii | Alistipes onderdonkii | 0.25 | ○ | ○ | Prevotella corporis (10.86) | |
| 6 | Anaerococcus vaginalis | Anaerococcus vaginalis | 0.19 | ○ | ○ | Pasteurella multocida (15.61) | |
| 7 | Arthrobacter cumminsii | Arthrobacter cumminsii | 0.19 | ○ | ○ | Bacillus megaterium (3.8) | |
| 8 | Bacillus cereus | Bacillus cereus | 0.64 | ○ | ○ | Bacillus pumilus (2.48) | |
| 9 | Bacillus coagulans | Bacillus coagulans | 0.12 | ○ | ○ | Actinomyces sp. (6.17) | |
| 10 | Bacillus licheniformis | Bacillus licheniformis | 0.13 | ○ | ○ | Bacillus subtilis subsp. subtilis (0.16) | #2 |
| 11 | Bacillus megaterium | Bacillus megaterium | 0.21 | ○ | ○ | Arthrobacter megaterium (3.64) | |
| 12 | Bacillus pumilus | Bacillus licheniformis | 0.2 | × | ○ | Bacillus pumilus (0.27) | #2 |
| 13 | Bacillus subtilis subsp. Subtilis | Bacillus licheniformis | 0.14 | × | ○ | Bacillus subtilis subsp. subtilis (0.17) | #2 |
| 14 | Bacteroides dorei | Bacteroides dorei | 0.27 | ○ | ○ | Bacteroides vulgatus (1.36) | |

DIFF. = DIFFERENCE VALUE
○ = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 11A

| BLIND TEST PERFORMED BY USING IMPROVED TM MAPPING METHOD WITH IMLL PROBES (IN REAL-TIME PCR INSTRUMENT WITH THERMAL VARIATION OF ± 0.4°C) | | | | | | | |
|---|---|---|---|---|---|---|---|
| No. | BACTERIAL DNA USED | IDENTIFICATION RESULTS | DIFF. | CONSISTENCY OF RESULTS | | SECOND MOST SIMILAR MICROORGANISM IN IDENTIFICATION RESULT (DIFF.) | SPECIFICITY IN DATABASE (Difference Value ≦ 0.8) |
| | | | | SPECIES LEVEL | GENUS LEVEL | | |
| 15 | Bacteroides finegoldii | Bacteroides finegoldii | 0.21 | O | O | Bacteroides thetaiotaomicron (2.63) | |
| 16 | Bacteroides fragilis | Bacteroides fragilis | 0.15 | O | O | Prevotella nigrescens (1.29) | |
| 17 | Bacteroides nordii | Bacteroides nordii | 0.21 | O | O | Bacteroides salyersiae (0.47) | #2 |
| 18 | Bacteroides salyersiae | Bacteroides salyersiae | 0.17 | O | O | Bacteroides nordii (0.43) | #2 |
| 19 | Bacteroides thetaiotaomicron | Bacteroides thetaiotaomicron | 0.27 | O | O | Bacteroides fragilis (1.44) | |
| 20 | Bacteroides uniformis | Bacteroides uniformis | 0.25 | O | O | Bacteroides fragilis (1.5) | |
| 21 | Bacteroides vulgatus | Bacteroides vulgatus | 0.26 | O | O | Bacteroides nordii (0.98) | |
| 22 | Bartonella henselae | Bartonella henselae | 0.61 | O | O | Borrelia burgdorferi (5.34) | |
| 23 | Bifidobacterium bifidum | Bifidobacterium bifidum | 0.43 | O | O | Prevotella veroralis (1.91) | |
| 24 | Bilophila wadsworthia | Bilophila wadsworthia | 0.41 | O | O | Borrelia burgdorferi (7.24) | |
| 25 | Bordetella pertussis | Bordetella pertussis | 0.25 | O | O | Achromobacter xylosoxidans (5.78) | |

DIFF. = DIFFERENCE VALUE
O = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 11B

BLIND TEST PERFORMED BY USING IMPROVED TM MAPPING METHOD WITH IMLL PROBES (IN REAL-TIME PCR INSTRUMENT WITH THERMAL VARIATION OF ± 0.4°C)

| No. | BACTERIAL DNA USED | IDENTIFICATION RESULTS | DIFF. | CONSISTENCY OF RESULTS | | SECOND MOST SIMILAR MICROORGANISM IN IDENTIFICATION RESULT (DIFF.) | SPECIFICITY IN DATABASE (Difference Value ≤ 0.8) |
|---|---|---|---|---|---|---|---|
| | | | | SPECIES LEVEL | GENUS LEVEL | | |
| 26 | Borrelia burgdorferi | Borrelia burgdorferi | 0.17 | ○ | ○ | Chryseobacterium gleum (4.03) | |
| 27 | Brevibacillus laterosporus | Brevibacillus laterosporus | 0.16 | ○ | ○ | Lactobacillus crispatus (3.89) | |
| 28 | Campylobacter coli | Campylobacter coli | 0.26 | ○ | ○ | Campylobacter jejuni subsp. jejuni (0.3) | #1 |
| 29 | Campylobacter jejuni subsp. jejuni | Campylobacter coli | 0.21 | × | ○ | Campylobacter jejuni subsp. jejuni (0.3) | #1 |
| 30 | Campylobacter rectus | Campylobacter rectus | 0.12 | ○ | ○ | Eggerthella lenta (4.55) | |
| 31 | Capnocytophaga gingivalis | Capnocytophaga gingivalis | 0.25 | ○ | ○ | Capnocytophaga granulosa (1.4) | |
| 32 | Capnocytophaga granulosa | Capnocytophaga granulosa | 0.16 | ○ | ○ | Capnocytophaga gingivalis (0.99) | |
| 33 | Capnocytophaga haemolytica | Capnocytophaga haemolytica | 0.24 | ○ | ○ | Capnocytophaga sputigena (1.13) | |
| 34 | Capnocytophaga ochracea | Capnocytophaga ochracea | 0.15 | ○ | ○ | Capnocytophaga haemolytica (1.31) | |
| 35 | Capnocytophaga sputigena | Capnocytophaga sputigena | 0.18 | ○ | ○ | Capnocytophaga haemolytica (1.49) | |
| 36 | Chryseobacterium gleum | Chryseobacterium gleum | 0.12 | ○ | ○ | Borrelia burgdorferi (3.94) | |

DIFF. = DIFFERENCE VALUE
○ = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 11C

BLIND TEST PERFORMED BY USING IMPROVED TM MAPPING METHOD WITH LNA PROBES (IN REAL-TIME PCR INSTRUMENT WITH THERMAL VARIATION OF ± 0.4°C)

| No. | BACTERIAL DNA USED | IDENTIFICATION RESULTS | DIFF. | CONSISTENCY OF RESULTS | | SECOND MOST SIMILAR MICROORGANISM IN IDENTIFICATION RESULT (DIFF.) | SPECIFICITY IN DATABASE (Difference Value ≦ 0.8) |
|---|---|---|---|---|---|---|---|
| | | | | SPECIES LEVEL | GENUS LEVEL | | |
| 37 | Citrobacter amalonaticus | Citrobacter amalonaticus | 0.38 | O | O | Enterobacter aerogenes (1.36) | |
| 38 | Citrobacter freundii | Citrobacter freundii | 0.63 | O | O | Enterobacter cloacae subsa.cloacae (4.66) | |
| 39 | Clostridium difficile | Clostridium difficile | 0.42 | O | O | Staphylococcus capitis/epidermidis (6.78) | |
| 40 | Clostridium histolyticum | Clostridium histolyticum | 0.4 | O | O | Lactobacillus crispatus (7.24) | |
| 41 | Clostridium hylemonae | Clostridium hylemonae | 0.24 | O | O | Prevotella timonesis (4.4) | |
| 42 | Clostridium paraputrificum | Clostridium paraputrificum | 0.23 | O | O | Clostridium tertium (2.47) | |
| 43 | Clostridium perfringus | Clostridium perfringus | 0.46 | O | O | Clostridium paraputrificum (3.16) | |
| 44 | Clostridium sporogenes | Clostridium sporogenes | 0.3 | O | O | Bacillus cereu (3.75) | |
| 45 | Clostridium subterminal | Clostridium subterminal | 0.31 | O | O | Bacillus licheniformis (4.54) | |
| 46 | Clostridium tertium | Clostridium tertium | 0.3 | O | O | Clostridium paraputrificum (2.74) | |
| 47 | Corynebacterium amycolatum | Corynebacterium xerosis | 0.42 | × | O | Corynebacterium amycolatum (0.51) | #1 |

DIFF. = DIFFERENCE VALUE
O = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 11D

BLIND TEST PERFORMED BY USING IMPROVED Tm MAPPING METHOD WITH TmL PROBES (IN REAL-TIME PCR INSTRUMENT WITH THERMAL VARIATION OF ± 0.4°C)

| No. | BACTERIAL DNA USED | IDENTIFICATION RESULTS | DIFF. | CONSISTENCY OF RESULTS SPECIES LEVEL | CONSISTENCY OF RESULTS GENUS LEVEL | SECOND MOST SIMILAR MICROORGANISM IN IDENTIFICATION RESULT (DIFF.) | SPECIFICITY IN DATABASE (Difference Value ≦ 0.8) |
|---|---|---|---|---|---|---|---|
| 48 | Corynebacterium macginleyi | Corynebacterium macginleyi | 0.22 | ○ | ○ | Gardnerella vaginalis (4.61) | |
| 49 | Corynebacterium striatum | Corynebacterium striatum | 0.36 | ○ | ○ | Corynebacterium xerosis (4.32) | |
| 50 | Corynebacterium xerosis | Corynebacterium xerosis | 0.43 | ○ | ○ | Corynebacterium amycolatum (0.55) | #1 |
| 51 | Eggerthella lenta | Eggerthella lenta | 0.19 | ○ | ○ | Campylobacter rectus (4.52) | |
| 52 | Eikenella corrodens | Eikenella corrodens | 0.51 | ○ | ○ | Bartonella henselae (9.47) | |
| 53 | Empedobacter brevis | Empedobacter brevis | 0.22 | ○ | ○ | None≧10 | |
| 54 | Enterobacter aerogenes | Enterobacter aerogenes | 0.39 | ○ | ○ | Klebsiella oxytoca (1.32) | |
| 55 | Enterobacter cloacae subsp. cloacae | Enterobacter cloacae subsp. cloacae | 0.36 | ○ | ○ | Enterobacter aerogenes (1.52) | |
| 56 | Enterococcus avium | Enterococcus avium | 0.22 | ○ | ○ | Enterococcus gallinarum (2.83) | |
| 57 | Enterococcus casseliflavus | Enterococcus faecium | 0.22 | × | ○ | Enterococcus casseliflavus (0.24) | #4 |
| 58 | Enterococcus durans | Enterococcus raffinosus | 0.17 | × | ○ | Enterococcus durans (0.21) | |
| 59 | Enterococcus faecalis | Enterococcus faecalis | 0.15 | ○ | ○ | Enterococcus casseliflavus (1.78) | #4 |

DIFF. = DIFFERENCE VALUE
○ = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 11E

| BLIND TEST PERFORMED BY USING IMPROVED TM MAPPING METHOD WITH 1MALL PROBES (IN REAL-TIME PCR INSTRUMENT WITH THERMAL VARIATION OF ± 0.4°C) | | | | | | | |
|---|---|---|---|---|---|---|---|
| No. | BACTERIAL DNA USED | IDENTIFICATION RESULTS | DIFF. | CONSISTENCY OF RESULTS | | SECOND MOST SIMILAR MICROORGANISM IN IDENTIFICATION RESULT (DIFF.) | SPECIFICITY IN DATABASE (Difference Value ≦ 0.8) |
| | | | | SPECIES LEVEL | GENUS LEVEL | | |
| 60 | Enterococcus faecium | Enterococcus casseliflavus | 0.23 | × | ○ | Enterococcus faecium (0.30) | #4 |
| 61 | Enterococcus gallinarum | Enterococcus durans | 0.15 | × | ○ | Enterococcus gallinarum (0.2) | #4 |
| 62 | Enterococcus raffinosus | Enterococcus raffinosus | 0.12 | ○ | ○ | Enterococcus casseliflavus (0.17) | #4 |
| 63 | Escherichia alberti | Escherichia alberti | 0.27 | ○ | ○ | Enterobacter cloacae subsp. cloacae (4.53) | |
| 64 | Escherichia coli | Escherichia coli | 0.31 | ○ | ○ | Escherichia alberti (5.44) | |
| 65 | Eubacterium limosum | Eubacterium limosum | 0.32 | ○ | ○ | Haemophilus influenzae (12.41) | |
| 66 | Finegoldia magna | Finegoldia magna | 0.25 | ○ | ○ | Proteus vulgaris (4.89) | |
| 67 | Fusobacterium necrophorum | Fusobacterium necrophorum | 0.24 | ○ | ○ | Streptobacillus moniliformis (9.46) | |
| 68 | Fusobacterium periodonticum | Fusobacterium periodonticum | 0.52 | ○ | ○ | Prevotella bivia (10.42) | |
| 69 | Fusobacterium varium | Fusobacterium varium | 0.33 | ○ | ○ | Clostridium difficile (6.78) | |
| 70 | Gardnerella vaginalis | Gardnerella vaginalis | 0.44 | ○ | ○ | Corynebacterium macginleyi (4.83) | |
| 71 | Gemella morbillorum | Gemella morbillorum | 0.35 | ○ | ○ | Geobacillus stearothermophilus (4.14) | |

DIFF. = DIFFERENCE VALUE
○ = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 11F

| BLIND TEST PERFORMED BY USING IMPROVED TM MAPPING METHOD WITH IMI PROBES (IN REAL-TIME PCR INSTRUMENT WITH THERMAL VARIATION OF ± 0.4°C) | | | | | | |
|---|---|---|---|---|---|---|
| No. | BACTERIAL DNA USED | IDENTIFICATION RESULTS | DIFF. | CONSISTENCY OF RESULTS | | SECOND MOST SIMILAR MICROORGANISM IN IDENTIFICATION RESULT (DIFF.) | SPECIFICITY IN DATABASE (Difference Value ≤ 0.8) |
| | | | | SPECIES LEVEL | GENUS LEVEL | | |
| 72 | Geobacillus stearothermophilus | Geobacillus stearothermophilus | 0.27 | ○ | ○ | Gemella morbillorum (4.15) | |
| 73 | Haemophilus influenzae | Haemophilus influenzae | 0.56 | ○ | ○ | Salmonella enterica (5.94) | |
| 74 | Halomonas venusta | Halomonas venusta | 0.2 | ○ | ○ | Pseudoxanthomonas aeruginosa (6.16) | |
| 75 | Klebsiella oxytoca Klebsiella | Klebsiella oxytoca | 0.33 | ○ | ○ | Enterobacter aerogenes (1.06) | |
| 76 | pneumoniae | Klebsiella pneumoniae | 0.45 | ○ | ○ | Klebsiella oxytoca (3.63) | |
| 77 | Kocuria rosea | Kocuria rosea | 0.43 | ○ | ○ | Micrococcus luteus (7.55) | |
| 78 | Lactobacillus acidophilus | Lactobacillus acidophilus | 0.39 | ○ | ○ | Lactobacillus crispatus (2.83) | |
| 79 | Lactobacillus crispatus | Lactobacillus crispatus | 0.3 | ○ | ○ | Lactobacillus acidophilus (2.22) | |
| 80 | Lactobacillus fermentum | Lactobacillus fermentum | 0.33 | ○ | ○ | Lactobacillus crispatus (4.96) | |
| 81 | Lactobacillus jensenii | Lactobacillus jensenii | 0.16 | ○ | ○ | Enterococcus durans (4.13) | |
| 82 | Lactococcus garvieae | Lactococcus garvie | 0.22 | ○ | ○ | Gemella morbillorum (6.01) | |
| 83 | Legionella pneumophila subsp.pneumophila | Legionella pneumophila subsp.pneumophila | 0.49 | ○ | ○ | Corynebacterium macginleyi (7.17) | |

DIFF. = DIFFERENCE VALUE
○ = CONSISTENT, × = INCONSISTENT

1 = ONE SPECIES BELONGING TO IDENTICAL GENUS WITHIN DIFF. ≤ 0.8
2 = TWO SPECIES BELONGING TO IDENTICAL GENUS WITHIN DIFF. ≤ 0.8
3 = THREE SPECIES BELONGING TO IDENTICAL GENUS WITHIN DIFF. ≤ 0.8
4 = FOUR SPECIES BELONGING TO IDENTICAL GENUS WITHIN DIFF. ≤ 0.8

FIG. 11G

TABLE 3-2

BLIND TEST PERFORMED BY USING IMPROVED TM MAPPING METHOD WITH TM PROBES (IN REAL-TIME PCR INSTRUMENT WITH THERMAL VARIATION OF ± 0.4℃)

| No. | BACTERIAL DNA USED | IDENTIFICATION RESULTS | DIFF. | CONSISTENCY OF RESULTS SPECIES LEVEL | CONSISTENCY OF RESULTS GENUS LEVEL | SECOND MOST SIMILAR MICROORGANISM IN IDENTIFICATION RESULT (DIFF.) | SPECIFICITY IN DATABASE (Difference Value ≦ 0.8) |
|---|---|---|---|---|---|---|---|
| 84 | Leptospira interrogans serovar Copenhageni | Leptospira interrogans serovar Copenhageni | 0.34 | ○ | ○ | Prevotella corporis (8.74) | |
| 85 | Listeria monocytogenes | Listeria monocytogenes | 0.24 | ○ | ○ | Enterococcus faecalis (5.41) | |
| 86 | Micrococcus luteus | Micrococcus luteus | 0.18 | ○ | ○ | Corynebacterium striatum (7.05) | |
| 87 | Morganella morganii | Morganella morganii | 0.29 | ○ | ○ | Providencia rettgeri (6.44) | |
| 88 | Nocardia cyriacigeorgica | Nocardia cyriacigeorgica | 0.13 | ○ | ○ | Prevotella veroralis (4.21) | |
| 89 | Odoribacter splanchnicus | Odoribacter splanchnicus | 0.13 | ○ | ○ | Porphyromonas gingivalis (5.93) | |
| 90 | Pantoea agglomerans | Pantoea agglomerans | 0.35 | ○ | ○ | Salmonella enterica (5.39) | |
| 91 | Parvimonas micra | Parvimonas micra | 0.24 | ○ | ○ | Prevotella intermedia (8.45) | |
| 92 | Pasteurella multocida | Pasteurella multocida | 0.37 | ○ | ○ | Providencia rettgeri (7.28) | |
| 93 | Peptoniphilus asaccharolyticus | Peptoniphilus asaccharolyticus | 0.25 | ○ | ○ | Arthrobacter cumminsii (9.45) | |
| 94 | Peptoniphilus gorbachii | Peptoniphilus gorbachii | 0.34 | ○ | ○ | Legionella pneumophila subsp. Pneumophila (9.72) | |
| 95 | Peptostreptococcus anaerobius | Peptostreptococcus anaerobius | 0.2 | ○ | ○ | None #1 | |
| 96 | Plesiomonas shigelloides | Plesiomonas shigelloides | 0.24 | ○ | ○ | Vibrio vulnificus (5.86) | |

DIFF. = DIFFERENCE VALUE
○ = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 12A

BLIND TEST PERFORMED BY USING IMPROVED TM MAPPING METHOD WITH IMLL PROBES (IN REAL-TIME PCR INSTRUMENT WITH THERMAL VARIATION OF ± 0.4°C)

| No. | BACTERIAL DNA USED | IDENTIFICATION RESULTS | DIFF. | CONSISTENCY OF RESULTS SPECIES LEVEL | CONSISTENCY OF RESULTS GENUS LEVEL | SECOND MOST SIMILAR MICROORGANISM IN IDENTIFICATION RESULT (DIFF.) | SPECIFICITY IN DATABASE (Difference Value ≦ 0.8) |
|---|---|---|---|---|---|---|---|
| 97 | Porphyromonas gingivalis | Porphyromonas gingivalis | 0.21 | ○ | ○ | Odoribacter splanchnicus (6.01) | |
| 98 | Prevotella corporis | Prevotella corporis | 0.36 | ○ | ○ | Porphyromonas gingivalis (6.95) | |
| 99 | Prevotella intermedia | Prevotella intermedia | 0.25 | ○ | ○ | Parvimonas micra (8.27) | |
| 100 | Prevotella melaninogenica | Prevotella melaninogenica | 0.44 | ○ | ○ | Prevotella veroralis (5.93) | |
| 101 | Prevotella timonensis | Prevotella timonensis | 0.2 | ○ | ○ | Prevotella veroralis (1.81) | |
| 102 | Prevotella veroralis | Prevotella veroralis | 0.2 | ○ | ○ | Prevotella timonensis (1.73) | |
| 103 | Propionibacterium acnes | Propionibacterium acnes | 0.22 | ○ | ○ | Propionibacterium granulosum (4.41) | |
| 104 | Propionibacterium granulosum | Propionibacterium granulosum | 0.16 | ○ | ○ | Propionibacterium acnes (4.27) | |
| 105 | Proteus vulgaris | Proteus mirabilis | 0.2 | × | ○ | Proteus mirabilis (0.34) | #1 |
| 106 | Proteus vulgaris | Proteus vulgaris | 0.23 | ○ | ○ | Proteus mirabilis (0.3) | #1 |
| 107 | Pseudomonas aeruginosa | Pseudomonas aeruginosa | 0.33 | ○ | ○ | Acinetobacter calcoaceticus (5.82) | |
| 108 | Pseudomonas fluorescens | Pseudomonas fluorescens | 0.39 | ○ | ○ | Pseudomonas putida (3.27) | |
| 109 | Pseudomonas putida | Pseudomonas putida | 0.44 | ○ | ○ | Pseudomonas fluorescens (3.44) | |
| 110 | Salmonella enterica | Salmonella enterica | 0.42 | ○ | ○ | Klebsiella oxytoca (4.63) | |
| 111 | Serratia marcescens | Serratia marcescens | 0.22 | ○ | ○ | Raoultella planticola (3.85) | |

DIFF. = DIFFERENCE VALUE
○ = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 12B

BLIND TEST PERFORMED BY USING IMPROVED TM MAPPING METHOD WITH IMLL PROBES (IN REAL TIME PCR INSTRUMENT WITH THERMAL VARIATION OF ± 0.4°C)

| No. | BACTERIAL DNA USED | IDENTIFICATION RESULTS | DIFF. | CONSISTENCY OF RESULTS SPECIES LEVEL | CONSISTENCY OF RESULTS GENUS LEVEL | SECOND MOST SIMILAR MICROORGANISM IN IDENTIFICATION RESULT (DIFF.) | SPECIFICITY IN DATABASE (Difference Value ≤ 0.8) |
|---|---|---|---|---|---|---|---|
| 112 | Serratia plymuthia | Serratia plymuthia | 0.27 | ○ | ○ | Yersinia pseudotuberculosis (3.39) | |
| 113 | Staphylococcus aureus | Staphylococcus warneri | 0.26 | × | ○ | Staphylococcus aureus (0.4) | #3 |
| 114 | Staphylococcus capitis/epidermidis | Staphylococcus capitis/epidermidis | 0.2 | ○ | ○ | Staphylococcus warneri (0.57) | #2 |
| 115 | Staphylococcus cohnii | Staphylococcus cohnii | 0.23 | ○ | ○ | Staphylococcus saprophyticus subsp.saprophyticus (0.7) | |
| 116 | Staphylococcus haemolyticus | Staphylococcus haemolyticus | 0.25 | ○ | ○ | Staphylococcus simulans (0.27) | #4 |
| 117 | Staphylococcus hominis | Staphylococcus hominis | 0.28 | ○ | ○ | Shaemolyticus (2.15) | |
| 118 | Staphylococcus intermedius | Staphylococcus intermedius | 0.23 | ○ | ○ | Staphylococcus lugdunensis (0.3) | #4 |
| 119 | Staphylococcus lugdunensis | Staphylococcus intermedius | 0.21 | × | ○ | Staphylococcus lugdunensis (0.23) | #4 |
| 120 | Staphylococcus saprophyticus subsp.saprophyticus | Staphylococcus saprophyticus subsp.saprophyticus | 0.35 | ○ | ○ | Staphylococcus cohnii (0.59) | #1 |
| 121 | Staphylococcus schleiferi subsp.coagulans | Staphylococcus intermedius | 0.23 | × | ○ | Staphylococcus schleiferi subsp.coagulans (0.3) | #4 |
| 122 | Staphylococcus simulans | Staphylococcus simulans | 0.26 | ○ | ○ | Staphylococcus haemolyticus (0.29) | #4 |

DIFF. = DIFFERENCE VALUE
○ = CONSISTENT, × = INCONSISTENT

1 = ONE SPECIES BELONGING TO IDENTICAL GENUS WITHIN DIFF. ≤ 0.8
2 = TWO SPECIES BELONGING TO IDENTICAL GENUS WITHIN DIFF. ≤ 0.8
3 = THREE SPECIES BELONGING TO IDENTICAL GENUS WITHIN DIFF. ≤ 0.8
4 = FOUR SPECIES BELONGING TO IDENTICAL GENUS WITHIN DIFF. ≤ 0.8

FIG. 12C

| BLIND TEST PERFORMED BY USING IMPROVED TM MAPPING METHOD WITH IMLL PROBES (IN REAL-TIME PCR INSTRUMENT WITH THERMAL VARIATION OF ± 0.4°C) | | | | | | | |
|---|---|---|---|---|---|---|---|
| No. | BACTERIAL DNA USED | IDENTIFICATION RESULTS | DIFF. | CONSISTENCY OF RESULTS | | SECOND MOST SIMILAR MICROORGANISM IN IDENTIFICATION RESULT (DIFF.) | SPECIFICITY IN DATABASE (Difference Value ≦ 0.8) |
| | | | | SPECIES LEVEL | GENUS LEVEL | | |
| 123 | Staphylococcus warneri | Staphylococcus aureus | 0.33 | × | ○ | Staphylococcus warneri (0.34) | #3 |
| 124 | Stenotrophomonas maltophilia | Stenotrophomonas maltophilia | 0.2 | ○ | ○ | Pseudomonas fluorescens (8.51) | |
| 125 | Streptobacillus moniliformis | Streptobacillus moniliformis | 0.3 | ○ | ○ | Fusobacterium varium (6.79) | |
| 126 | Streptococcus agalactiae | Streptococcus agalactiae | 0.28 | ○ | ○ | Streptococcus oralis (1.66) | |
| 127 | Streptococcus anginosus | Streptococcus anginosus | 0.3 | ○ | ○ | Streptococcus salivarius (4.07) | |
| 128 | Streptococcus bovis | Streptococcus bovis | 0.16 | ○ | ○ | Streptococcus gallolyticus subsp.pasteurianus (0.25) | #1 |
| 129 | Streptococcus constellatus | Streptococcus constellatus | 0.22 | ○ | ○ | Streptococcus salivarius (1.74) | |
| 130 | Streptococcus dysgalactiae | Streptococcus dysgalactiae | 0.07 | ○ | ○ | Streptococcus pyogenes (2.16) | |
| 131 | Streptococcus gallolyticus subsp.pasteurianus | Streptococcus bovis | 0.31 | × | ○ | Streptococcus gallolyticus subsp.pasteurianus (0.43) | #1 |
| 132 | Streptococcus gordonii | Streptococcus gordonii | 0.13 | ○ | ○ | Staphylococcus oralis (0.69) | #2 |
| 133 | Streptococcus intermedius | Streptococcus intermedius | 0.24 | ○ | ○ | Streptococcus sanguinis (3.00) | |

DIFF. = DIFFERENCE VALUE
○ = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 12D

BLIND TEST PERFORMED BY USING IMPROVED TM MAPPING METHOD WITH IMLL PROBES (IN REAL-TIME PCR INSTRUMENT WITH THERMAL VARIATION OF ± 0.4°C)

| No. | BACTERIAL DNA USED | IDENTIFICATION RESULTS | DIFF. | CONSISTENCY OF RESULTS SPECIES LEVEL | CONSISTENCY OF RESULTS GENUS LEVEL | SECOND MOST SIMILAR MICROORGANISM IN IDENTIFICATION RESULT (DIFF.) | SPECIFICITY IN DATABASE (Difference Value ≦ 0.8) |
|---|---|---|---|---|---|---|---|
| 134 | Streptococcus mitis | Streptococcus mitis | 0.17 | ○ | ○ | Streptococcus oralis (0.2) | #2 |
| 135 | Streptococcus orali | Streptococcus mitis | 0.11 | × | ○ | Streptococcus oralis (0.16) | #2 |
| 136 | Streptococcus pneumoniae | Streptococcus pneumoniae | 0.57 | ○ | ○ | Streptococcus oralis (4.97) | |
| 137 | Streptococcus pyogenes | Streptococcus pyogenes | 0.16 | ○ | ○ | Streptococcus dysgalatiae (2.24) | |
| 138 | Streptococcus salivarius | Streptococcus salivarius | 0.19 | ○ | ○ | Streptococcus constellatus (1.56) | |
| 139 | Streptococcus sanguinis | Streptococcus sanguinis | 0.21 | ○ | ○ | Streptococcus bovis (1.3) | |
| 140 | Tannerella forsythus | Tannerella forsythus | 0.16 | ○ | ○ | Porphyromonas gingivalis (7.06) | |
| 141 | Treponema denticola | Treponema denticola | 0.19 | ○ | ○ | Bordetella pertussis (7.13) | |
| 142 | Vibrio fluvialis | Vibrio fluvialis | 0.39 | ○ | ○ | Vibrio vulnificus (7.29) | |
| 143 | Vibrio vulnificus | Vibrio vulnificus | 0.66 | ○ | ○ | Plesiomonas shigelloides (6.48) | |
| 144 | Yersinia enterocolitica subsp. enterocolitica | Yersinia enterocolitica subsp. enterocolitica | 0.32 | ○ | ○ | Serratia plymuthica (4.26) | |
| 145 | Yersinia pseudotuberculosis | Yersinia pseudotuberculosis | 0.49 | ○ | ○ | Serratia plymuthica (3.91) | |

DIFF. = DIFFERENCE VALUE
○ = CONSISTENT, × = INCONSISTENT

1 = ONE SPECIES BELONGING TO IDENTICAL GENUS WITHIN DIFF. ≦ 0.8
2 = TWO SPECIES BELONGING TO IDENTICAL GENUS WITHIN DIFF. ≦ 0.8
3 = THREE SPECIES BELONGING TO IDENTICAL GENUS WITHIN DIFF. ≦ 0.8
4 = FOUR SPECIES BELONGING TO IDENTICAL GENUS WITHIN DIFF. ≦ 0.8

FIG. 12E

TABLE 4

| No. | CONVENTIONAL CULTURE METHOD IDENTIFICATION RESULT | TM MAPPING METHOD WITH IMLL PROBES (IN LIGHTCYCLER 480 : THERMAL VARIATION ± 0.4°C) IDENTIFICATION RESULT (DIFFERENCE VALUE) | SHORT PROBE FOR DETECTING S. AUREUS (TM VALUE) | CONSISTENCY |
|---|---|---|---|---|
| 1 | Bacillus cereus | Bacillus cereus (0.21) | | ○ |
| 2 | Bacillus cereus | Bacillus cereus (0.45) | | ○ |
| 3 | Enterobacter aerogenes | Enterobacter aerogenes (0.4) | | ○ |
| 4 | Enterococcus faecalis | Enterococcus faecalis (0.28) | | ○ |
| 5 | E. coli and Klebsiella pneumoniae | Escherichia coli (0.24) | | ○ |
| 6 | Escherichia coli | Escherichia coli (0.25) | | ○ |
| 7 | Escherichia coli | Escherichia coli (0.29) | | ○ |
| 8 | Escherichia coli | Escherichia coli (0.30) | | ○ |
| 9 | Escherichia coli | Escherichia coli (0.43) | | ○ |
| 10 | Escherichia coli | Escherichia coli (0.44) | | ○ |
| 11 | Proteus mirabilis and E. coli | Escherichia coli (0.5) | | ○ |
| 12 | Escherichia coli | Escherichia coli (0.52) | | ○ |
| 13 | Escherichia coli | Escherichia coli (0.59) | | ○ |
| 14 | Klebsiella oxytoca | Klebsiella oxytoca (0.40) | | ○ |
| 15 | Proteus mirabilis | Proteus mirabilis (0.38) or Proteus vulgatus (0.38) | | ○ |
| 16 | Proteus mirabilis | Proteus mirabilis (0.49) or Proteus vulgalis (0.54) | | ○ |
| 17 | Proteus mirabilis | Proteus vulgalis (0.36) or Proteus mirabilis (0.37) | | ○ |
| 18 | Pseudomonas aeruginosa | Pseudomonas aeruginosa (0.52) | | ○ |

○ = CONSISTENT, × = INCONSISTENT

FIG. 13A

| No. | CONVENTIONAL CULTURE METHOD IDENTIFICATION RESULT | TM MAPPING METHOD WITH IMLL PROBES (IN LIGHTCYCLER 480 : THERMAL VARIATION ± 0.4°C) | | CONSISTENCY |
|---|---|---|---|---|
| | | IDENTIFICATION RESULT (DIFFERENCE VALUE) | SHORT PROBE FOR DETECTING S. AUREUS (TM VALUE) | |
| 19 | Serratia marcescens | Serratia marcescens (0.43) | | ○ |
| 20 | Staphylococcus epidermidis | GENUS STAPHYLOCOCCUS | Staphylococcus capitis/epidermidis (53.25°C) | ○ |
| 21 | Staphylococcus epidermidis | GENUS STAPHYLOCOCCUS | Staphylococcus capitis/epidermidis (53.31°C) | ○ |
| 22 | Staphylococcus epidermidis | GENUS STAPHYLOCOCCUS | Staphylococcus capitis/epidermidis (53.13°C) | ○ |
| 23 | coagulase-negative staphylococci (CNS) | GENUS STAPHYLOCOCCUS | Staphylococcus capitis/epidermidis (53.25°C) | ○ |
| 24 | Staphylococcus aureus | GENUS STAPHYLOCOCCUS | Staphylococcus aureus (61.49°C) | ○ |
| 25 | Staphylococcus epidermidis | GENUS STAPHYLOCOCCUS | Staphylococcus capitis/epidermidis (53.25°C) | ○ |
| 26 | Staphylococcus epidermidis | GENUS STAPHYLOCOCCUS | Staphylococcus capitis/epidermidis (53.19°C) | ○ |
| 27 | Enterococcus faecalis and CNS | GENUS STAPHYLOCOCCUS | Staphylococcus capitis/epidermidis (53.15°C) | ○ |
| 28 | Staphylococcus epidermidis | GENUS STAPHYLOCOCCUS | Staphylococcus capitis/epidermidis (53.27°C) | ○ |
| 29 | Staphylococcus aureus | GENUS STAPHYLOCOCCUS | Staphylococcus aureus (61.31°C) | ○ |

○ = CONSISTENT, × = INCONSISTENT

FIG. 13B

| No. | CONVENTIONAL CULTURE METHOD IDENTIFICATION RESULT | TM MAPPING METHOD WITH IMLL PROBES (IN LIGHTCYCLER 480 : THERMAL VARIATION ± 0.4°C) IDENTIFICATION RESULT (DIFFERENCE VALUE) | SHORT PROBE FOR DETECTING S. AUREUS (TM VALUE) | CONSISTENCY |
|---|---|---|---|---|
| 30 | *Staphylococcus epidermidis* | GENUS STAPHYLOCOCCUS | *Staphylococcus capitis/epidermidis* (53.59°C) | ○ |
| 31 | *Staphylococcus epidermidis* | GENUS STAPHYLOCOCCUS | *Staphylococcus capitis/epidermidis* (53.21°C) | ○ |
| 32 | *Staphylococcus epidermidis* | GENUS STAPHYLOCOCCUS | *Staphylococcus capitis/epidermidis* (53.34°C) | ○ |
| 33 | *Staphylococcus aureus* | GENUS STAPHYLOCOCCUS | *Staphylococcus aureus* (61.26°C) | ○ |
| 34 | *Staphylococcus epidermidis* | GENUS STAPHYLOCOCCUS | *Staphylococcus capitis/epidermidis* (53.56°C) | ○ |
| 35 | *Staphylococcus epidermidis* | GENUS STAPHYLOCOCCUS | *Staphylococcus capitis/epidermidis* (53.63°C) | ○ |
| 36 | *Staphylococcus aureus* | GENUS STAPHYLOCOCCUS | *Staphylococcus aureus* (61.40°C) | ○ |
| 37 | *Staphylococcus epidermidis* | GENUS STAPHYLOCOCCUS | *Staphylococcus capitis/epidermidis* (53.67°C) | ○ |
| 38 | *Staphylococcus epidermidis* | GENUS STAPHYLOCOCCUS | *Staphylococcus capitis/epidermidis* (53.52°C) | ○ |
| 39 | *S. epidermidis and Bacillus cereus* | GENUS STAPHYLOCOCCUS | *Staphylococcus capitis/epidermidis* (53.86°C) | ○ |
| 40 | *Proteus mirabilis and S. aureus* | #1 | | × |

○ = CONSISTENT, × = INCONSISTENT

1 = DETERMINED TO BE INFECTED WITH A PLURALITY OF MICROORGANISMS (FAILURE TO BE IDENTIFIED)

FIG. 13C

SEQUENCE LISTING

```
<160> NUMBER OF SEQ ID NOS: 106

<210> SEQ ID NO 1
<211> LENGTH: 38
<212> TYPE: DNA
<213> ORGANISM: Artificial Sequence
<220> FEATURE:
<223> OTHER INFORMATION: probe

<400> SEQUENCE: 1
cacctactag ctaatcttat ctgggcacat ccgatggc                              38

<210> SEQ ID NO 2
<211> LENGTH: 42
<212> TYPE: DNA
<213> ORGANISM: Artificial Sequence
<220> FEATURE:
<223> OTHER INFORMATION: probe

<400> SEQUENCE: 2
ctcagaccag ctaacgatcg ttgccttagt aagccgttac ct                         42

<210> SEQ ID NO 3
<211> LENGTH: 45
<212> TYPE: DNA
<213> ORGANISM: Artificial Sequence
<220> FEATURE:
<223> OTHER INFORMATION: probe

<400> SEQUENCE: 3
```
cacgcggcat ggctccatca ggctttcccc cattgtcgaa gattc        45

<210> SEQ ID NO 4
<211> LENGTH: 41
<212> TYPE: DNA
<213> ORGANISM: Artificial Sequence
<220> FEATURE:
<223> OTHER INFORMATION: probe

<400> SEQUENCE: 4
cgccctgtaa ttccgaataa cgctagctcc caccgtatta c            41

<210> SEQ ID NO 5
<211> LENGTH: 44
<212> TYPE: DNA
<213> ORGANISM: Artificial Sequence
<220> FEATURE:
<223> OTHER INFORMATION: probe

<400> SEQUENCE: 5
ccaagttgag cccgggcctt tcactactga cttaacaaac cgcc         44

<210> SEQ ID NO 6
<211> LENGTH: 38
<212> TYPE: DNA
<213> ORGANISM: Artificial Sequence
<220> FEATURE:
<223> OTHER INFORMATION: probe

<400> SEQUENCE: 6
ggcacaacct cttaatactc atcgtttaca gcgtggac                38

<210> SEQ ID NO 7
<211> LENGTH: 42
<212> TYPE: DNA
<213> ORGANISM: Artificial Sequence
<220> FEATURE:
<223> OTHER INFORMATION: probe

<400> SEQUENCE: 7
atctctgcaa agttctaagg atgtcaagat taggtaaggt tc           42

<210> SEQ ID NO 8
<211> LENGTH: 20
<212> TYPE: DNA
<213> ORGANISM: Artificial Sequence
<220> FEATURE:
<223> OTHER INFORMATION: probe

<400> SEQUENCE: 8
gatccgcgct gcattagata                                    20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
agagtttgat catggctcag                                    20

<210> SEQ ID NO 10
<211> LENGTH: 17
<212> TYPE: DNA
<213> ORGANISM: Artificial Sequence

```
<220> FEATURE:
<223> OTHER INFORMATION: primer

<400> SEQUENCE: 10
ccgggaacgt attcacc                                                    17

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
tagagtttga tcatggctca g                                               21

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
cgtaggagtc tggaccgt                                                   18

<210> SEQ ID NO 13
<211> LENGTH: 17
<212> TYPE: DNA
<213> ORGANISM: Artificial Sequence
<220> FEATURE:
<223> OTHER INFORMATION: primer

<400> SEQUENCE: 13
gactcctacg ggaggca                                                    17

<210> SEQ ID NO 14
<211> LENGTH: 17
<212> TYPE: DNA
<213> ORGANISM: Artificial Sequence
<220> FEATURE:
<223> OTHER INFORMATION: primer

<400> SEQUENCE: 14
tattaccgcg gctgctg                                                    17

<210> SEQ ID NO 15
<211> LENGTH: 16
<212> TYPE: DNA
<213> ORGANISM: Artificial Sequence
<220> FEATURE:
<223> OTHER INFORMATION: primer

<400> SEQUENCE: 15
agcagccgcg gtaata                                                     16

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
ggactaccag ggtatctaat cct                                             23
```

```
<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
aacaggatta gataccctgg tag                                              23

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
aattaaacca catgctccac c                                                21

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
tggtttaatt cgatgcaacg c                                                21

<210> SEQ ID NO 20
<211> LENGTH: 17
<212> TYPE: DNA
<213> ORGANISM: Artificial Sequence
<220> FEATURE:
<223> OTHER INFORMATION: primer

<400> SEQUENCE: 20
gagctgacga cagccat                                                     17

<210> SEQ ID NO 21
<211> LENGTH: 40
<212> TYPE: DNA
<213> ORGANISM: Artificial Sequence
<220> FEATURE:
<223> OTHER INFORMATION: probe

<400> SEQUENCE: 21
cagaccagct aacgatcgtc gccttagtaa gccgttaccc                            40

<210> SEQ ID NO 22
<211> LENGTH: 42
<212> TYPE: DNA
<213> ORGANISM: Artificial Sequence
<220> FEATURE:
<223> OTHER INFORMATION: probe

<400> SEQUENCE: 22
ctcagaccag ctaaggatcg ttgccttagt aagccgttac ct                         42

<210> SEQ ID NO 23
<211> LENGTH: 43
<212> TYPE: DNA
<213> ORGANISM: Artificial Sequence
<220> FEATURE:
<223> OTHER INFORMATION: probe
```

<400> SEQUENCE: 23
gtactttaca acccgaaggc cttcttcata cacgcggcat ggc                43

<210> SEQ ID NO 24
<211> LENGTH: 35
<212> TYPE: DNA
<213> ORGANISM: Artificial Sequence
<220> FEATURE:
<223> OTHER INFORMATION: probe

<400> SEQUENCE: 24
ccttatcgcc ttcctccccg ctgaaagtgc tttac                        35

<210> SEQ ID NO 25
<211> LENGTH: 41
<212> TYPE: DNA
<213> ORGANISM: Artificial Sequence
<220> FEATURE:
<223> OTHER INFORMATION: probe

<400> SEQUENCE: 25
cgcccagtaa ttccgattaa cgcttgcacc ctccgtatta c                 41

<210> SEQ ID NO 26
<211> LENGTH: 41
<212> TYPE: DNA
<213> ORGANISM: Artificial Sequence
<220> FEATURE:
<223> OTHER INFORMATION: probe

<400> SEQUENCE: 26
ggccgactaa ttccgattaa cgattccacg ctccgtatta c                 41

<210> SEQ ID NO 27
<211> LENGTH: 50
<212> TYPE: DNA
<213> ORGANISM: Artificial Sequence
<220> FEATURE:
<223> OTHER INFORMATION: probe

<400> SEQUENCE: 27
cttaacaaac cgcctacgca cccttttaagc ccaataattc cgattaacgc       50

<210> SEQ ID NO 28
<211> LENGTH: 40
<212> TYPE: DNA
<213> ORGANISM: Artificial Sequence
<220> FEATURE:
<223> OTHER INFORMATION: probe

<400> SEQUENCE: 28
ctcaagtttg ccagtttccg atgaagttcc caggttgagc                   40

<210> SEQ ID NO 29
<211> LENGTH: 40
<212> TYPE: DNA
<213> ORGANISM: Artificial Sequence
<220> FEATURE:
<223> OTHER INFORMATION: probe

<400> SEQUENCE: 29
ctcaagtttg ccagtttcgg atgcagtttc caggttgagc                   40

<210> SEQ ID NO 30

```
<211> LENGTH: 42
<212> TYPE: DNA
<213> ORGANISM: Artificial Sequence
<220> FEATURE:
<223> OTHER INFORMATION: probe

<400> SEQUENCE: 30
ccacctctat gcagacatcg tttacggcgt ggactaccag gg            42

<210> SEQ ID NO 31
<211> LENGTH: 40
<212> TYPE: DNA
<213> ORGANISM: Artificial Sequence
<220> FEATURE:
<223> OTHER INFORMATION: probe

<400> SEQUENCE: 31
cctccagttt gtcatcggca gtctacattg agttcccaac               40

<210> SEQ ID NO 32
<211> LENGTH: 40
<212> TYPE: DNA
<213> ORGANISM: Artificial Sequence
<220> FEATURE:
<223> OTHER INFORMATION: probe

<400> SEQUENCE: 32
cctccagttt gtcaccggca gtctacattg agttcccaac               40

<210> SEQ ID NO 33
<211> LENGTH: 43
<212> TYPE: DNA
<213> ORGANISM: Artificial Sequence
<220> FEATURE:
<223> OTHER INFORMATION: probe

<400> SEQUENCE: 33
cttcatgtaa tcaggttgca gactccaatc cggactaaga cgc           43

<210> SEQ ID NO 34
<211> LENGTH: 42
<212> TYPE: DNA
<213> ORGANISM: Artificial Sequence
<220> FEATURE:
<223> OTHER INFORMATION: probe

<400> SEQUENCE: 34
ctagcgattc cgacttcatg aatacgagtt gcagcctaca at            42

<210> SEQ ID NO 35
<211> LENGTH: 38
<212> TYPE: DNA
<213> ORGANISM: Artificial Sequence
<220> FEATURE:
<223> OTHER INFORMATION: probe

<400> SEQUENCE: 35
gccatcggat gtgcccagat aagattagct agtaggtg                 38

<210> SEQ ID NO 36
<211> LENGTH: 38
<212> TYPE: DNA
<213> ORGANISM: Acinetobacter baumanii

<400> SEQUENCE: 36
gctaatagat gagcctaagt cggattagct agttggtg                 38
```

<210> SEQ ID NO 37
<211> LENGTH: 38
<212> TYPE: DNA
<213> ORGANISM: Acinetobacter calcoaceticus

<400> SEQUENCE: 37
gctaatagat gagcctaagt cggattagct agttggtg                              38

<210> SEQ ID NO 38
<211> LENGTH: 39
<212> TYPE: DNA
<213> ORGANISM: Actinomyces israelii

<400> SEQUENCE: 38
gccgcatggt gtggctggga agattcact tttgtggtg                              39

<210> SEQ ID NO 39
<211> LENGTH: 38
<212> TYPE: DNA
<213> ORGANISM: Aeromonas hydrophila

<400> SEQUENCE: 39
gcgattggat atgcccaggt gggattagct agttggtg                              38

<210> SEQ ID NO 40
<211> LENGTH: 38
<212> TYPE: DNA
<213> ORGANISM: Arthrobacter cumminsii

<400> SEQUENCE: 40
gttatccgga attattgggc gtaaagagct cgtaggcg                              38

<210> SEQ ID NO 41
<211> LENGTH: 38
<212> TYPE: DNA
<213> ORGANISM: Bacillus cereus

<400> SEQUENCE: 41
acttatggat ggacccgcgt cgcattagct agttggtg                              38

<210> SEQ ID NO 42
<211> LENGTH: 38
<212> TYPE: DNA
<213> ORGANISM: Bacteroides fragilis

<400> SEQUENCE: 42
ggtaaaggat ggggatgcgt tccattaggt tgttggtg                              38

<210> SEQ ID NO 43
<211> LENGTH: 38
<212> TYPE: DNA
<213> ORGANISM: Bacteroides nordii

<400> SEQUENCE: 43
ggtaaaagat ggggatgcgt tccattaggc agttggcg                              38

<210> SEQ ID NO 44
<211> LENGTH: 38
<212> TYPE: DNA
<213> ORGANISM: Bacteroides thetaiotaomicron

<400> SEQUENCE: 44

```
gttatcggat ggggatgcgt tccattaggc agttggtg                                   38

<210> SEQ ID NO 45
<211> LENGTH: 38
<212> TYPE: DNA
<213> ORGANISM: Bifidobacterium bifidum

<400> SEQUENCE: 45
ggcgtgggat ggggtcgcgt cctatcagct tgttggtg                                   38

<210> SEQ ID NO 46
<211> LENGTH: 38
<212> TYPE: DNA
<213> ORGANISM: Bilophila wadsworthia

<400> SEQUENCE: 46
gcttaaggat gagtccgcgt cccattagct agttggcg                                   38

<210> SEQ ID NO 47
<211> LENGTH: 38
<212> TYPE: DNA
<213> ORGANISM: Chryseobacterium gleum

<400> SEQUENCE: 47
ggatagagat gggcacgcgc aagattagat agttggtg                                   38

<210> SEQ ID NO 48
<211> LENGTH: 38
<212> TYPE: DNA
<213> ORGANISM: Citrobacter amalonaticus

<400> SEQUENCE: 48
gccatcggat gtgcccagat gggattagct agttggtg                                   38

<210> SEQ ID NO 49
<211> LENGTH: 38
<212> TYPE: DNA
<213> ORGANISM: Citrobacter freundii

<400> SEQUENCE: 49
gccatcggat gtgcccagat gggattagct agtaggtg                                   38

<210> SEQ ID NO 50
<211> LENGTH: 38
<212> TYPE: DNA
<213> ORGANISM: Clostridium difficile

<400> SEQUENCE: 50
agtacaggat ggacccgcgt ctgattagct agttggta                                   38

<210> SEQ ID NO 51
<211> LENGTH: 38
<212> TYPE: DNA
<213> ORGANISM: Clostridium hylemonae

<400> SEQUENCE: 51
ggtgtaagat gggcccgcgt ctgattaggt agttggta                                   38

<210> SEQ ID NO 52
<211> LENGTH: 38
<212> TYPE: DNA
<213> ORGANISM: Clostridium leptum

<400> SEQUENCE: 52
```
gctctgagat gagctcgcgt ctgattagct agttggtc                                  38

<210> SEQ ID NO 53
<211> LENGTH: 38
<212> TYPE: DNA
<213> ORGANISM: Corynebacterium striatum

<400> SEQUENCE: 53
ggtgcaagat gagctcgcgg cctatcagct tgttggtg                                  38

<210> SEQ ID NO 54
<211> LENGTH: 38
<212> TYPE: DNA
<213> ORGANISM: Eggerthella lenta

<400> SEQUENCE: 54
ggcaagggat ggggtcgcgg cccattaggt agtaggcg                                  38

<210> SEQ ID NO 55
<211> LENGTH: 38
<212> TYPE: DNA
<213> ORGANISM: Eikenella corrodens

<400> SEQUENCE: 55
gttattcgag cggccgataa ctgattagct agttggtg                                  38

<210> SEQ ID NO 56
<211> LENGTH: 38
<212> TYPE: DNA
<213> ORGANISM: Enterobacter aerogenes

<400> SEQUENCE: 56
gccatcagat gtgcccagat gggattagct agtaggtg                                  38

<210> SEQ ID NO 57
<211> LENGTH: 38
<212> TYPE: DNA
<213> ORGANISM: Enterobacter cloacae

<400> SEQUENCE: 57
gccatcagat gtgcccagat gggattagct agtaggtg                                  38

<210> SEQ ID NO 58
<211> LENGTH: 38
<212> TYPE: DNA
<213> ORGANISM: Enterococcus avium

<400> SEQUENCE: 58
actgatggat ggacccgcgg tgcattagct agttggtg                                  38

<210> SEQ ID NO 59
<211> LENGTH: 38
<212> TYPE: DNA
<213> ORGANISM: Enterococcus casseliflavus

<400> SEQUENCE: 59
actgatggat ggacccgcgg tgcattagct agttggtg                                  38

<210> SEQ ID NO 60
<211> LENGTH: 38
<212> TYPE: DNA
<213> ORGANISM: Enterococcus faecalis -continued

<400> SEQUENCE: 60
gctgatggat ggacccgcgg tgcattagct agttggtg             38

<210> SEQ ID NO 61
<211> LENGTH: 38
<212> TYPE: DNA
<213> ORGANISM: Enterococcus faecium

<400> SEQUENCE: 61
gctgatggat ggacccgcgg tgcattagct agttggtg             38

<210> SEQ ID NO 62
<211> LENGTH: 38
<212> TYPE: DNA
<213> ORGANISM: Escherichia albertii

<400> SEQUENCE: 62
gccatcggat gtgcccagat gggattagct tgttggtg             38

<210> SEQ ID NO 63
<211> LENGTH: 38
<212> TYPE: DNA
<213> ORGANISM: Escherichia coli

<400> SEQUENCE: 63
gccatcggat gtgcccagat gggattagct agtaggtg             38

<210> SEQ ID NO 64
<211> LENGTH: 37
<212> TYPE: DNA
<213> ORGANISM: Finegoldia magna

<400> SEQUENCE: 64
gtcatagatg ggctcgcgtc tgattagcta gttggtg              37

<210> SEQ ID NO 65
<211> LENGTH: 38
<212> TYPE: DNA
<213> ORGANISM: Fusobacterium necrophorum

<400> SEQUENCE: 65
gctaagagag agctttgcgt cccattagct agttggtg             38

<210> SEQ ID NO 66
<211> LENGTH: 38
<212> TYPE: DNA
<213> ORGANISM: Gardnerella vaginalis

<400> SEQUENCE: 66
ggcatgggat ggggtcgcgt cctatcagct tgtagctg             38

<210> SEQ ID NO 67
<211> LENGTH: 38
<212> TYPE: DNA
<213> ORGANISM: Gemella morbillorum

<400> SEQUENCE: 67
actatgagat ggctttgcgg tgcattagct agttggtg             38

<210> SEQ ID NO 68
<211> LENGTH: 38
<212> TYPE: DNA
<213> ORGANISM: Haemophilus influenzae

```
<400> SEQUENCE: 68
gccataggat gagcccaagt gggattaggt agttggtg                           38

<210> SEQ ID NO 69
<211> LENGTH: 38
<212> TYPE: DNA
<213> ORGANISM: Halomonas venusta

<400> SEQUENCE: 69
gctattggat gagcctatgt cggattagct agttggtg                           38

<210> SEQ ID NO 70
<211> LENGTH: 38
<212> TYPE: DNA
<213> ORGANISM: Klebsiella oxytoca

<400> SEQUENCE: 70
gccatcggat gtgcccagat gggattagct tgtaggtg                           38

<210> SEQ ID NO 71
<211> LENGTH: 38
<212> TYPE: DNA
<213> ORGANISM: Klebsiella pneumoniae

<400> SEQUENCE: 71
gccatcagat gtgcccagat gggattagct agtaggtg                           38

<210> SEQ ID NO 72
<211> LENGTH: 38
<212> TYPE: DNA
<213> ORGANISM: Lactobacillus crispatus

<400> SEQUENCE: 72
gctatgggat ggccccgcgg tgcattagct agttggta                           38

<210> SEQ ID NO 73
<211> LENGTH: 38
<212> TYPE: DNA
<213> ORGANISM: Lactobacillus jensenii

<400> SEQUENCE: 73
gctaaaggat ggacctgcga tgcattagct agttggta                           38

<210> SEQ ID NO 74
<211> LENGTH: 38
<212> TYPE: DNA
<213> ORGANISM: Lactococcus garvieae

<400> SEQUENCE: 74
actacttgat gatcccgcgt tgtattagct agttggta                           38

<210> SEQ ID NO 75
<211> LENGTH: 38
<212> TYPE: DNA
<213> ORGANISM: Listeria monocytogenes

<400> SEQUENCE: 75
gcttacagat gggcccgcgg tgcattagct agttggta                           38

<210> SEQ ID NO 76
<211> LENGTH: 38
<212> TYPE: DNA
```

```
<213> ORGANISM: Morganella morganii

<400> SEQUENCE: 76
gccatcagat gaacccatat gggattagct agtaggtg                              38

<210> SEQ ID NO 77
<211> LENGTH: 38
<212> TYPE: DNA
<213> ORGANISM: Mycoplasma hominis

<400> SEQUENCE: 77
actaaaagat gagggtgcgg aacattagtt agttggtg                              38

<210> SEQ ID NO 78
<211> LENGTH: 38
<212> TYPE: DNA
<213> ORGANISM: Nocardia cyriacigeorgica

<400> SEQUENCE: 78
ggtgcgagat gggcccgcgg cctatcagct tgttggtg                              38

<210> SEQ ID NO 79
<211> LENGTH: 38
<212> TYPE: DNA
<213> ORGANISM: Odoribacter splanchnicus

<400> SEQUENCE: 79
ggtatcggat gggcatgcgt cctattagtt agttggcg                              38

<210> SEQ ID NO 80
<211> LENGTH: 38
<212> TYPE: DNA
<213> ORGANISM: Parvimonas micra

<400> SEQUENCE: 80
ggtgtaagaa gggctcgcgt ctgattagct agttggaa                              38

<210> SEQ ID NO 81
<211> LENGTH: 38
<212> TYPE: DNA
<213> ORGANISM: Pasteurella multocida

<400> SEQUENCE: 81
gccataagat gagcccaagt gggattaggt agttggtg                              38

<210> SEQ ID NO 82
<211> LENGTH: 38
<212> TYPE: DNA
<213> ORGANISM: Prevotella corporis

<400> SEQUENCE: 82
ggtatgggat ggggatgcgt ctgattagct tgttggcg                              38

<210> SEQ ID NO 83
<211> LENGTH: 38
<212> TYPE: DNA
<213> ORGANISM: Prevotella intermedia

<400> SEQUENCE: 83
ggtggaggat ggggatgcgt ctgattagct tgttggtg                              38

<210> SEQ ID NO 84
<211> LENGTH: 38
```

```
<212> TYPE: DNA
<213> ORGANISM: Propionibacterium acnes

<400> SEQUENCE: 84
gctttcgcct gtgacgaagc gtgagtgacg gtaatggg                              38

<210> SEQ ID NO 85
<211> LENGTH: 38
<212> TYPE: DNA
<213> ORGANISM: Proteus mirabilis

<400> SEQUENCE: 85
actatcggat gaacccatat gggattagct agtaggtg                              38

<210> SEQ ID NO 86
<211> LENGTH: 38
<212> TYPE: DNA
<213> ORGANISM: Pseudomonas aeruginosa

<400> SEQUENCE: 86
gctatcagat gagcctaggt cggattagct agttggtg                              38

<210> SEQ ID NO 87
<211> LENGTH: 38
<212> TYPE: DNA
<213> ORGANISM: Raoultella planticola

<400> SEQUENCE: 87
gccatcagat gtgcccagat gggattagct agtaggtg                              38

<210> SEQ ID NO 88
<211> LENGTH: 38
<212> TYPE: DNA
<213> ORGANISM: Salmonella enterica

<400> SEQUENCE: 88
gccatcagat gtgcccagat gggattagct tgttggtg                              38

<210> SEQ ID NO 89
<211> LENGTH: 38
<212> TYPE: DNA
<213> ORGANISM: Serratia marcescens

<400> SEQUENCE: 89
gccatcagat gtgcccagat gggattagct agtaggtg                              38

<210> SEQ ID NO 90
<211> LENGTH: 38
<212> TYPE: DNA
<213> ORGANISM: Sphingomonas paucimobilis

<400> SEQUENCE: 90
gcctgaggat gagcccgcgt tggattaggt agttggtg                              38

<210> SEQ ID NO 91
<211> LENGTH: 38
<212> TYPE: DNA
<213> ORGANISM: Staphylococcus aureus

<400> SEQUENCE: 91
acttatagat ggatccgcgc tgcattagct agttggta                              38

<210> SEQ ID NO 92
```

<211> LENGTH: 38
<212> TYPE: DNA
<213> ORGANISM: Staphylococcus capitis

<400> SEQUENCE: 92
acttatagat ggatccgcgc cgcattagct agttggta                          38

<210> SEQ ID NO 93
<211> LENGTH: 38
<212> TYPE: DNA
<213> ORGANISM: Staphylococcus cohnii

<400> SEQUENCE: 93
acttatagat ggacccgcgc cgtattagct agttggta                          38

<210> SEQ ID NO 94
<211> LENGTH: 38
<212> TYPE: DNA
<213> ORGANISM: Staphylococcus haemolyticus

<400> SEQUENCE: 94
acttatagat ggacccgcgc cgtattagct agttggta                          38

<210> SEQ ID NO 95
<211> LENGTH: 38
<212> TYPE: DNA
<213> ORGANISM: Staphylococcus hominis

<400> SEQUENCE: 95
acttatagat ggacctgcgc cgtattagct agttggta                          38

<210> SEQ ID NO 96
<211> LENGTH: 38
<212> TYPE: DNA
<213> ORGANISM: Staphylococcus lugdunensis

<400> SEQUENCE: 96
acttatagat ggacccgcgc cgtattagct agttggtg                          38

<210> SEQ ID NO 97
<211> LENGTH: 38
<212> TYPE: DNA
<213> ORGANISM: Stenotrophomonas maltophilia

<400> SEQUENCE: 97
gcgattgaat gagccgatgt cggattagct agttggcg                          38

<210> SEQ ID NO 98
<211> LENGTH: 38
<212> TYPE: DNA
<213> ORGANISM: Streptococcus agalactiae

<400> SEQUENCE: 98
actgtgagat ggacctgcgt tgtattagct agttggtg                          38

<210> SEQ ID NO 99
<211> LENGTH: 38
<212> TYPE: DNA
<213> ORGANISM: Streptococcus anginosus

<400> SEQUENCE: 99
gctagtagat ggacctgcgt tgtattagct agtaggta                          38

```
<210> SEQ ID NO 100
<211> LENGTH: 38
<212> TYPE: DNA
<213> ORGANISM: Streptococcus constellatus

<400> SEQUENCE: 100
actaccagat ggacctgcgt tgtattagct agttggtg                              38

<210> SEQ ID NO 101
<211> LENGTH: 38
<212> TYPE: DNA
<213> ORGANISM: Streptococcus dysgalactiae

<400> SEQUENCE: 101
actatgagat ggacctgcgt tgtattagct agttggtg                              38

<210> SEQ ID NO 102
<211> LENGTH: 38
<212> TYPE: DNA
<213> ORGANISM: Streptococcus gordonii

<400> SEQUENCE: 102
actaccagat ggacctgcgt tgtattagct agtaggtg                              38

<210> SEQ ID NO 103
<211> LENGTH: 38
<212> TYPE: DNA
<213> ORGANISM: Streptococcus mitis

<400> SEQUENCE: 103
actaccagat ggacctgcgt tgtattagct agttggtg                              38

<210> SEQ ID NO 104
<211> LENGTH: 38
<212> TYPE: DNA
<213> ORGANISM: Streptococcus pneumoniae

<400> SEQUENCE: 104
actaccagat ggacctgcgt tgtattagct agttggtg                              38

<210> SEQ ID NO 105
<211> LENGTH: 38
<212> TYPE: DNA
<213> ORGANISM: Streptococcus pyogenes

<400> SEQUENCE: 105
actatgagat ggacctgcgt tgtattagct agttggtg                              38

<210> SEQ ID NO 106
<211> LENGTH: 38
<212> TYPE: DNA
<213> ORGANISM: Streptococcus salivarius

<400> SEQUENCE: 106
actacaagat ggacctgcgt tgtattagct agtaggtg                              38
```

TM MAPPING METHOD

CROSS REFERENCE TO RELATED APPLICATION

This application is a continuation of International Patent Application No. PCT/JP2018/023382, having an international filing date of Jun. 20, 2018, which designated the United States, the entirety of which is incorporated herein by reference. Japanese Patent Application No. 2017-244461 filed on Dec. 20, 2017 is also incorporated herein by reference in its entirety.

BACKGROUND ART

The present disclosure relates to a Tm mapping method using Imperfect-Match Linear Long (IMLL) probes.

To save lives of patients with severe sepsis by performing an appropriate antimicrobial therapy, it is important to detect and identify pathogenic microorganisms present in patient samples as rapidly as possible.

However, it typically takes 2 to 3 days from the sample collection to the pathogenic microorganism identification in current common examinations.

Accordingly, there are still significant risks in the initial infection-treatment, including emergence of multidrug-resistant microbes caused by using broad-spectrum antimicrobial agents and risk of life-threatening conditions in patients with severe infections due to incorrect choice of antimicrobial agents.

To solve the problem, the Tm mapping method (Melting Temperature Mapping Method), which allows identification of unspecified pathogenic microorganisms within 3 hours after sample collection, has been suggested (WO 2007/097323, WO 2010/082640, and Antibiotics & chemotherapy, Vol. 31, S-1, 2015).

The Tm mapping method identifies a microorganism by performing PCR with bacterial universal primers designed to target base sequence regions shared by all bacteria, measuring Tm values (temperatures at which 50% of double-stranded DNA dissociates into single-stranded DNAs) of the resultant seven PCR amplified products, and searching a database using the combination of the seven Tm values, which reflects differences in base sequences among bacterial species, as a finger print of the microorganism. This method is a genetic testing that identifies unknown pathogenic microorganisms without blood culture in about 3 hours after blood collection.

In the Tm mapping method, differences in base sequences among microorganisms are identified using differences in Tm values of PCR amplified products, and there will be 200 or more microorganisms within the scope of difference as slight as about 5° C. (×7 combinations).

As a result, high measurement accuracy, which is a measurement error within ±0.1° C. of Tm values between PCR tubes, is required, but there are only a few commercial real-time PCR instruments that fulfill the requirement.

This has stood in the way of the widespread adoption of the Tm mapping method.

BRIEF DESCRIPTION OF THE DRAWINGS

FIGS. 8A-8E illustrates the mismatches between the IMLL probe 1-2 and the target sequence in each bacterial species (71 bacterial species). The sequence identification numbers for each sequence are:

Figure 1:
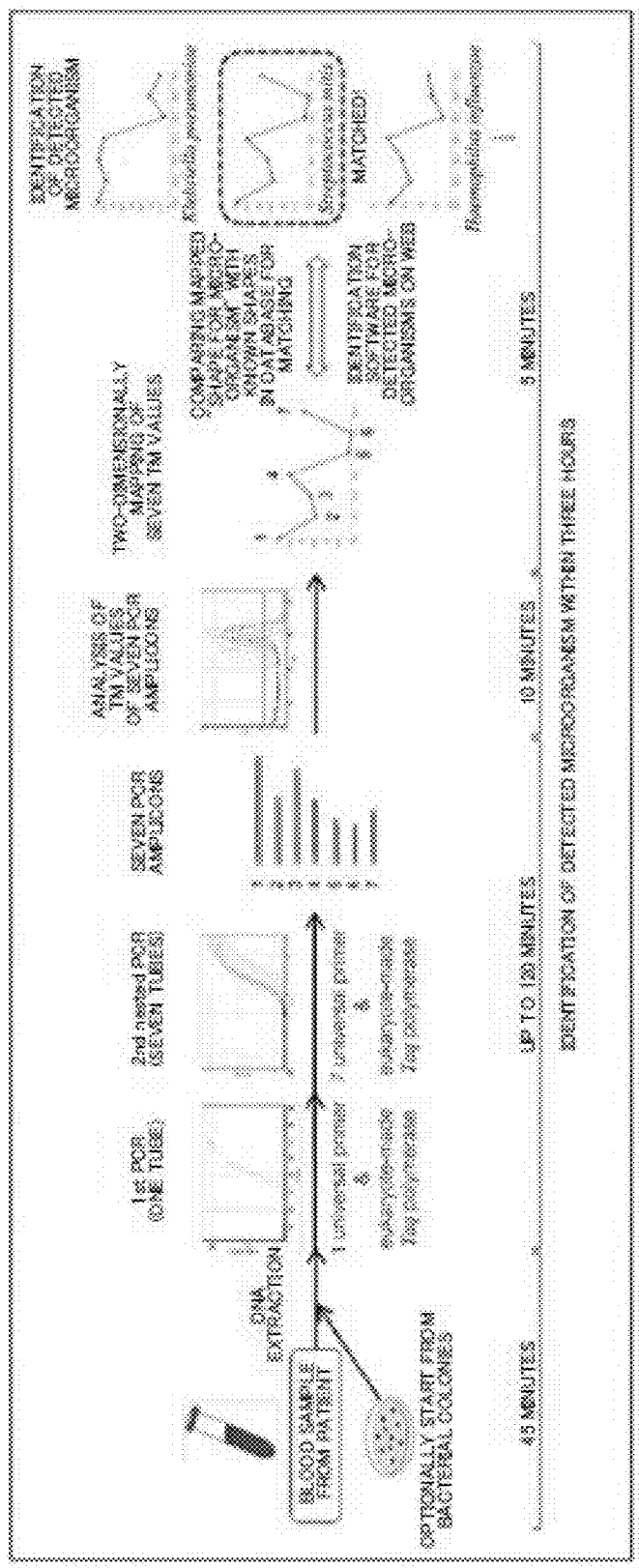
FIG. 1 illustrates an overview of a conventional Tm mapping method. The graphs shown in the overview are conceptual illustrations and display no numerical values.

BASE SEQUENCE OF IMLL PROBE 1-1: SEQ ID NO: 35;
*Acinetobacter baumanii* SEQ ID NO: 36
*Acinetobacter calcoaceticus* SEQ ID NO: 37
*Actinomyces israelii* SEQ ID NO: 38
*Aeromonas hydrophila* SEQ ID NO: 39
*Arthrobacter cumminsii* SEQ ID NO: 40
*Bacillus cereus* SEQ ID NO: 41
*Bacteroides fragilis* SEQ ID NO: 42
*Bacteroides nordii* SEQ ID NO: 43
*Bacteroides thetaiotaomicron* SEQ ID NO: 44
*Bifidobacterium bifidum* SEQ ID NO: 45
*Bilophila wadsworthia* SEQ ID NO: 46
*Chryseobacterium gleum* SEQ ID NO: 47
*Citrobacter amalonaticus* SEQ ID NO: 48
*Citrobacter freundii* SEQ ID NO: 49
*Clostridium difficile* SEQ ID NO: 50
*Clostridium hylemonae* SEQ ID NO: 51
*Clostridium leptum* SEQ ID NO: 52
*Corynebacterium striatum* SEQ ID NO: 53
*Eggerthella lenta* SEQ ID NO: 54
*Eikenella corrodens* SEQ ID NO: 55
*Enterobacter aerogenes* SEQ ID NO: 56
*Enterobacter cloacae* SEQ ID NO: 57
*Enterococcus avium* SEQ ID NO: 58
*Enterococcus casseliflavus* SEQ ID NO: 59
*Enterococcus faecalis* SEQ ID NO: 60
*Enterococcus faecium* SEQ ID NO: 61
*Escherichia albertii* SEQ ID NO: 62
*Escherichia coli* SEQ ID NO: 63
*Finegoldia magna* SEQ ID NO: 64
*Fusobacterium necrophorum* SEQ ID NO: 65
*Gardnerella vaginalis* SEQ ID NO: 66
*Gemella morbillorum* SEQ ID NO: 67
*Haemophilus influenzae* SEQ ID NO: 68
*Halmonas venusta* SEQ ID NO: 69
*Klebsiella oxytoca* SEQ ID NO: 70
*Klebsiella pneumoniae* SEQ ID NO: 71
*Lactobacillus crispatus* SEQ ID NO:72

*Lactobacillus jensenii* SEQ ID NO: 73
*Lactococcus garvieae* SEQ ID NO: 74
*Listeria monocytogenes* SEQ ID NO: 75
*Morganella morganii* SEQ ID NO: 76
*Mycoplasma hominis* SEQ ID NO: 77
*Nocardia cyriacigeorgica* SEQ ID NO: 78
*Odoribacter splanchinicus* SEQ ID NO: 79
*Parvimonas micra* SEQ ID NO: 80
*Pasteurella multocida* SEQ ID NO: 81
*Prevotella corporis* SEQ ID NO: 82
*Prevotella intermedia* SEQ ID NO: 83
*Propionibacterium acnes* SEQ ID NO: 84
*Proteus mirabilis* SEQ ID NO: 85
*Pseudomonas aeruginosa* SEQ ID NO: 86
*Raoultella planticola* SEQ ID NO: 87
*Salmonella enterica* SEQ ID NO: 88
*Serratia marcescens* SEQ ID NO: 89
*Sphingomonas paucimobilis* SEQ ID NO: 90
*Staphylococcus aureus* SEQ ID NO: 91
*Staphylococcus capitis/epidermidis* SEQ ID NO: 92
*Staphylococcus cohnii* SEQ ID NO: 93
*Staphylococcus haemolyticus* SEQ ID NO: 94
*Staphylococcus hominis* SEQ ID NO: 95
*Staphylococcus lugdunensis* SEQ ID NO: 96
*Stenotrophomonas maltophilia* SEQ ID NO: 97
*Streptococcus agalactiae* SEQ ID NO: 98
*Streptococcus anginosus* SEQ ID NO: 99
*Streptococcus constellatus* SEQ ID NO: 100
*Streptococcus dysgalactiae* SEQ ID NO: 101
*Streptococcus gordonii* SEQ ID NO: 102
*Streptococcus mitis* SEQ ID NO: 103
*Streptococcus pneumoniae* SEQ ID NO: 104
*Streptococcus pyogenes* SEQ ID NO: 105
*Streptococcus salivarius* SEQ ID NO: 106

FIGS. 9A-9E illustrates similarity (Table 1) of Tm mapping shapes among 71 bacterial species in the database.

FIGS. 10A-10B illustrates results (Table 2) of individual identification performed by using a database constructed to include 71 bacterial species and a real-time PCR instrument with a thermal variation of ±0.1° C. and starting from whole blood samples.

FIGS. 11A-11G illustrates results (Table 3-1) of an individual blind test performed by using a database constructed to include 145 bacterial species and a real-time PCR instrument with a thermal variation of ±0.4° C.

FIGS. 12A-12E illustrates Table 3-2, a continuation of FIGS. 11A-11G.

FIGS. 13A-C illustrates results (Table 4) of individual identification performed by using a database constructed to include 145 bacterial species and a real-time PCR instrument with a thermal variation of ±0.4° C. and starting from whole blood samples.

DESCRIPTION OF EMBODIMENTS

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

The inventors investigated a novel Tm mapping method using long probes rather than PCR amplified products, leading to the disclosure.

According to the disclosure, the Tm mapping method can be performed in almost all commercial real-time PCR instruments.

As a long probe, for example, a quenching probe was designed to have an incompletely matched sequence with a very long length of about 40 bases. This led to the finding that the probes can bind to most microorganism sequences and can give wide Tm values.

Long probes, even with many mismatches, can bind to imperfect-match sequences because the long length of the probes results in increased hydrogen bonding force.

On the other hand, long probes have a strong tendency to form secondary structures and self-quench. Thus, optimum probes were selected by conducting research such as repeated trial production of long probes that form no secondary structures using Delta-G and by confirming operation, leading to completion of the present invention.

Depending on the number and position of mismatches, the probes allowed acquisition of wide differences in Tm values for each bacterial species, that is, differences up to 20° C. or more among bacterial species, as compared with the differences in Tm values of conventional PCR amplified products among bacterial species.

The inventors have designated such probes Imperfect-Match Linear Long (IMLL) probes.

Seven IMLL probes were actually used to construct first a preliminary database including the Tm mapping shapes for 71 bacterial species.

As a result, it is demonstrated that real-time PCR instruments whose measurement error of Tm values between PCR tubes is within ±0.5° C. theoretically enable correct distinction among or identification of microorganisms at least at the genus level and often at the species level.

The measurement error between PCR tubes of current commercial real-time PCR instruments is almost within ±0.3° C. Therefore, IMLL probes can be used to conduct the Tm mapping method in almost all real-time PCR instruments.

On the other hand, it is nearly impossible to distinguish between, for example, *Enterococcus faecalis* and *Enterococcus faecium* due to the limited ability of the designed probes, but at least the genus is correctly identified.

Also, because of sequence similarity among species belonging to the genus *Staphylococcus*, it is also difficult to distinguish them at the species level. However, an additional step was performed for only 10 minutes by using a short probe specifically recognizing *Staphylococcus aureus*, which allowed discrimination between *Staphylococcus aureus* and other species except *Staphylococcus aureus* belonging to the genus *Staphylococcus*.

The invention will be described below in detail.

The conventional Tm mapping method refers to a method of rapidly identifying infection-causing pathogenic microorganisms performed in the steps described below that represent a flow of steps as shown in FIG. 1.

It should be noted that FIG. 1 illustrates a flow of steps and the graphs are only conceptual illustrations.

A method of identifying infection-causing pathogenic microorganisms by (1) extracting a microbial DNA from a sample such as blood;
(2) performing nested PCR using the extracted microbial DNA, as a template, and a plurality of universal primers;
(3a) melting and analyzing a plurality of gene amplified products (PCR amplicons) obtained in the above-referenced step;
(4) two-dimensionally mapping a plurality of melting temperature (Tm) values; and
(5) checking the two-dimensionally mapped "shape" against a database.

Figure 2:
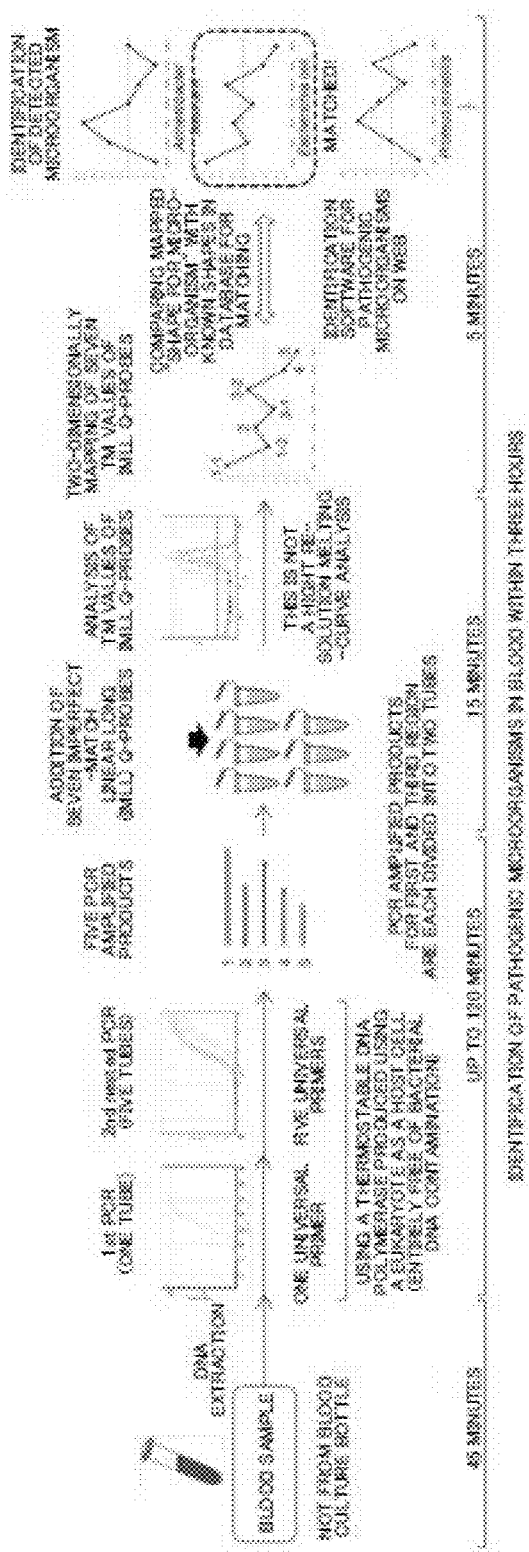
FIG. 2 illustrates an overview of an improved Tm mapping method of the disclosure. The graphs shown in the overview are conceptual illustrations and display no numerical values.

In the improved Tm mapping method of the disclosure, the conventional step (3a) is substituted with step (3) as shown in a flow of steps in FIG. 2. In step (3), Imperfect-Match Linear Long (IMLL) probes are added to the gene amplified products (PCR amplicons) obtained in the step (2) described above to analyze Tm values of IMLL probes rather than Tm values of the gene amplified products. The subsequent steps (4) and (5) are the same as in the conventional Tm mapping method.

Step (1): extracting a microbial DNA from a sample such as blood.

Bacterial DNA is extracted directly from a clinical sample (e.g., 2 mL of a whole blood sample) to utilize it as a template for PCR.

The extraction method is not limited to particular methods, and clinical sample collection, DNA extraction, and the like may be performed using any known method.

Step (2): Performing nested PCR using the extracted microbial DNA, as a template, and a plurality of bacterial universal primers (primers that detect almost all bacteria).

This step includes nested PCR using 5 to 7 bacterial universal primer sets (one primer set per tube in the second PCR).

These primers can detect almost all bacterial species.

To improve the accuracy of this step, it is preferable to use a thermostable DNA polymerase that is recombinantly produced using a eukaryote as a host cell, without bacterial DNA contamination.

The use of the polymerase enables highly sensitive and reliable detection of bacteria without false positive results in bacterial universal PCR. Therefore, the PCR allows direct identification of infection-causing pathogenic microorganisms from patient samples.

Figures 3, 4:
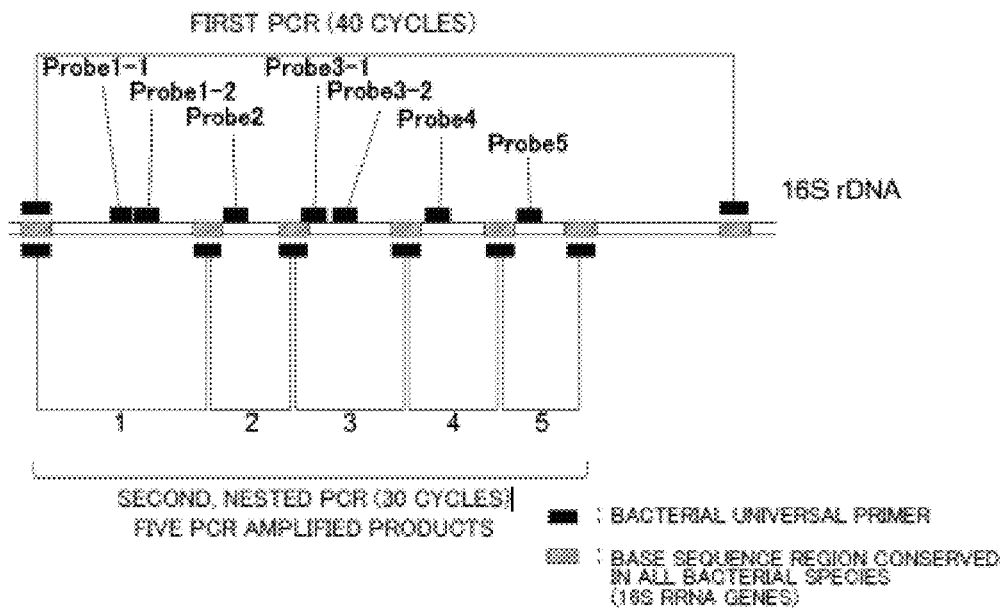
FIG. 3 illustrates a strategy of designing primers and probes. Nested PCR is performed using five bacterial universal primer sets, and then seven IMLL probes are additionally used for the PCR amplicons to obtain seven Tm values.
FIG. 4 illustrates binding sites of IMLL probes.
Figure 5A:
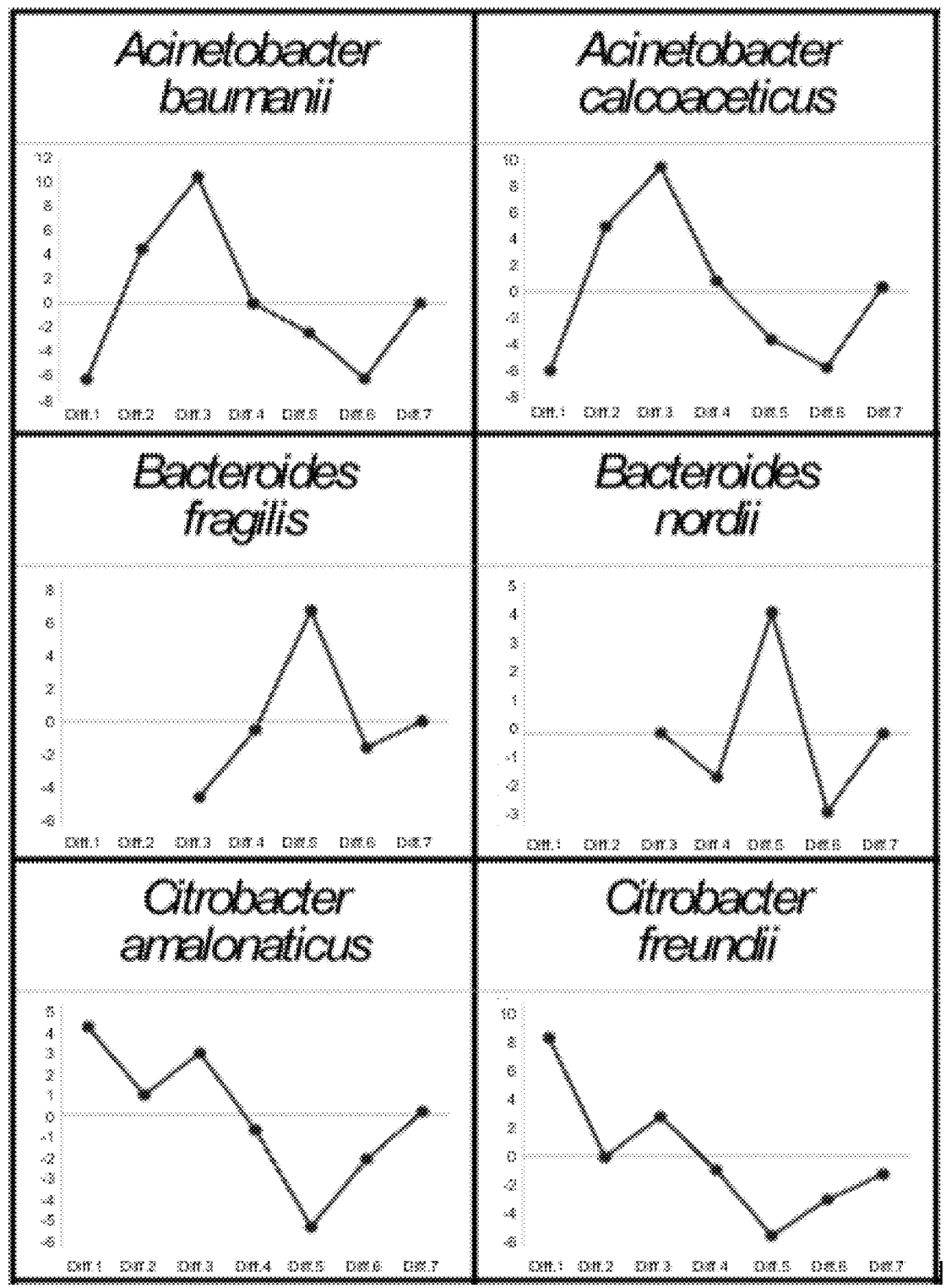
FIGS. 5A-5L illustrate Tm mapping shapes (IMLL probes) of 71 bacterial species registered in a database. It should be noted that FIGS. 5A-5L are conceptual illustrations of Tm mapping shapes, and thus the X axis shows the average of seven Tm values with specific numerical values omitted.
Figure 5B:
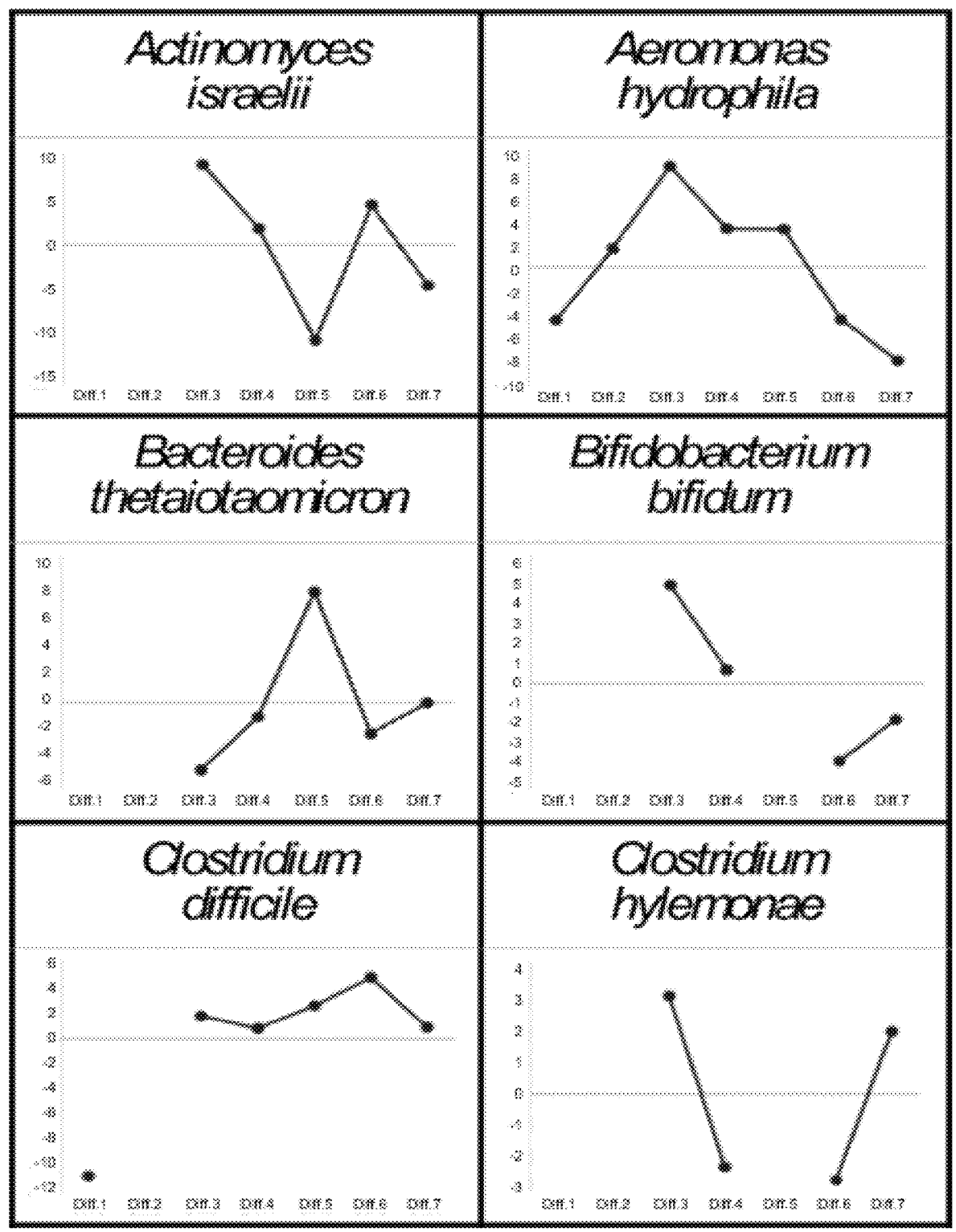
Figure 5C:
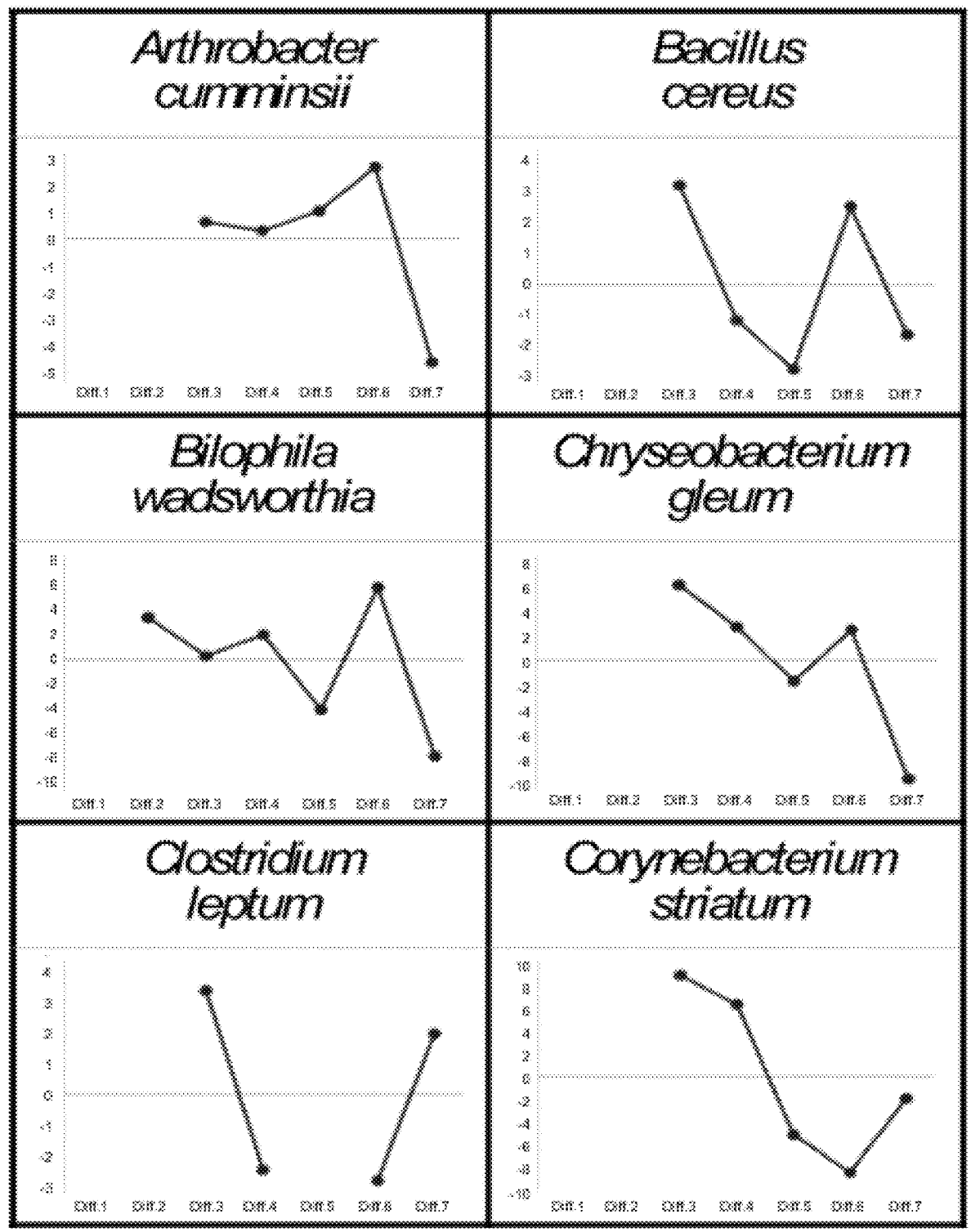
Figure 5D:
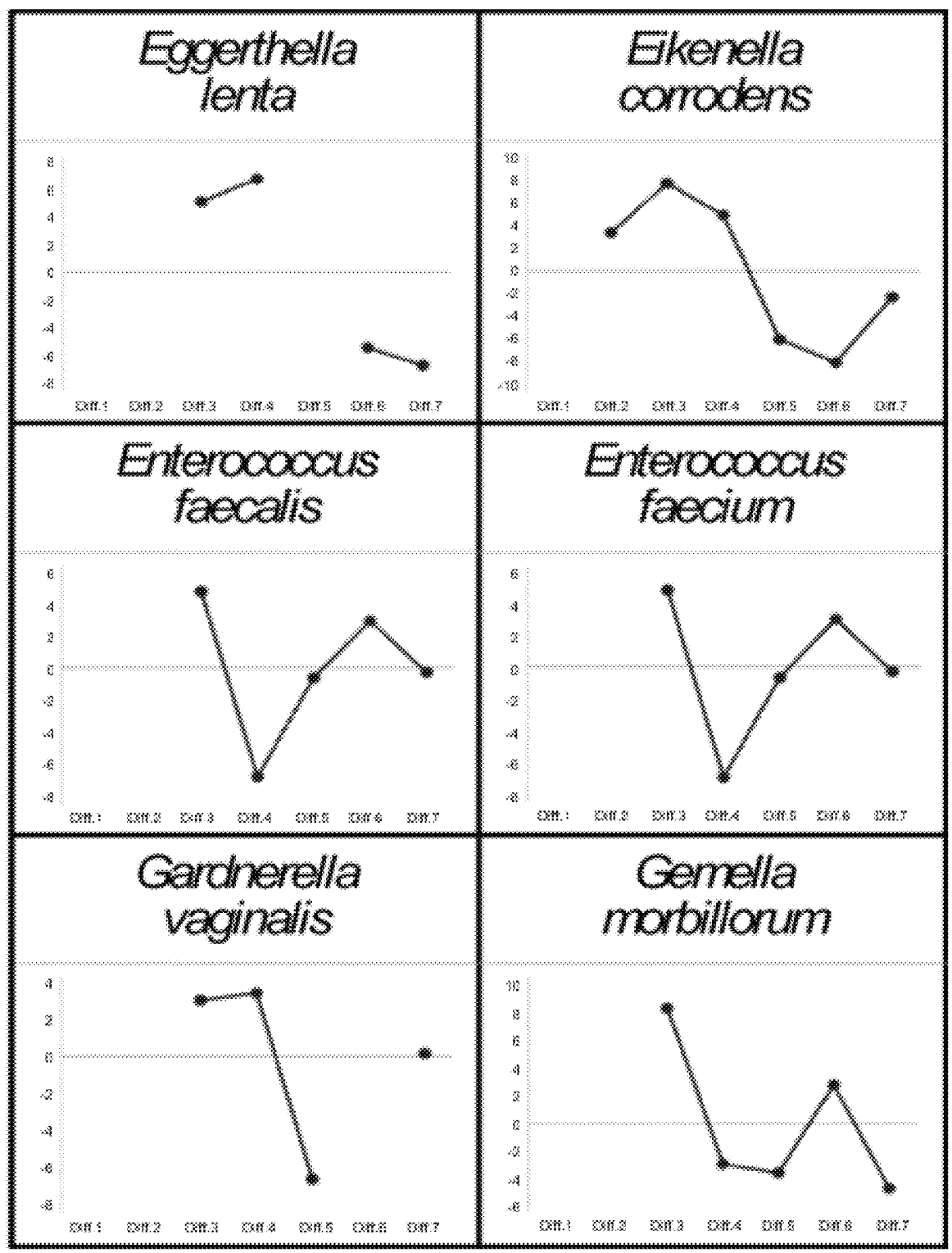
Figure 5E:
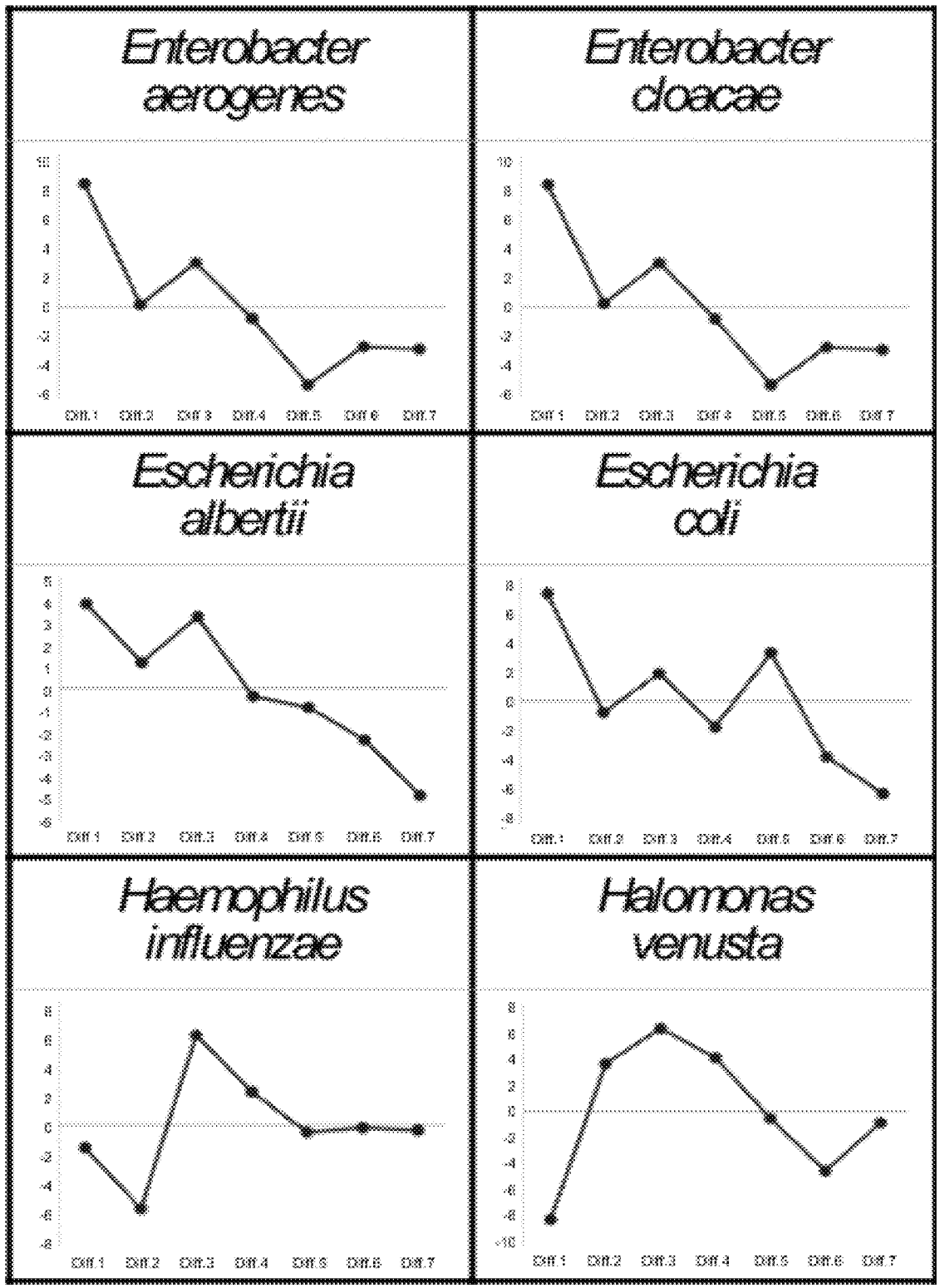
Figure 5F:
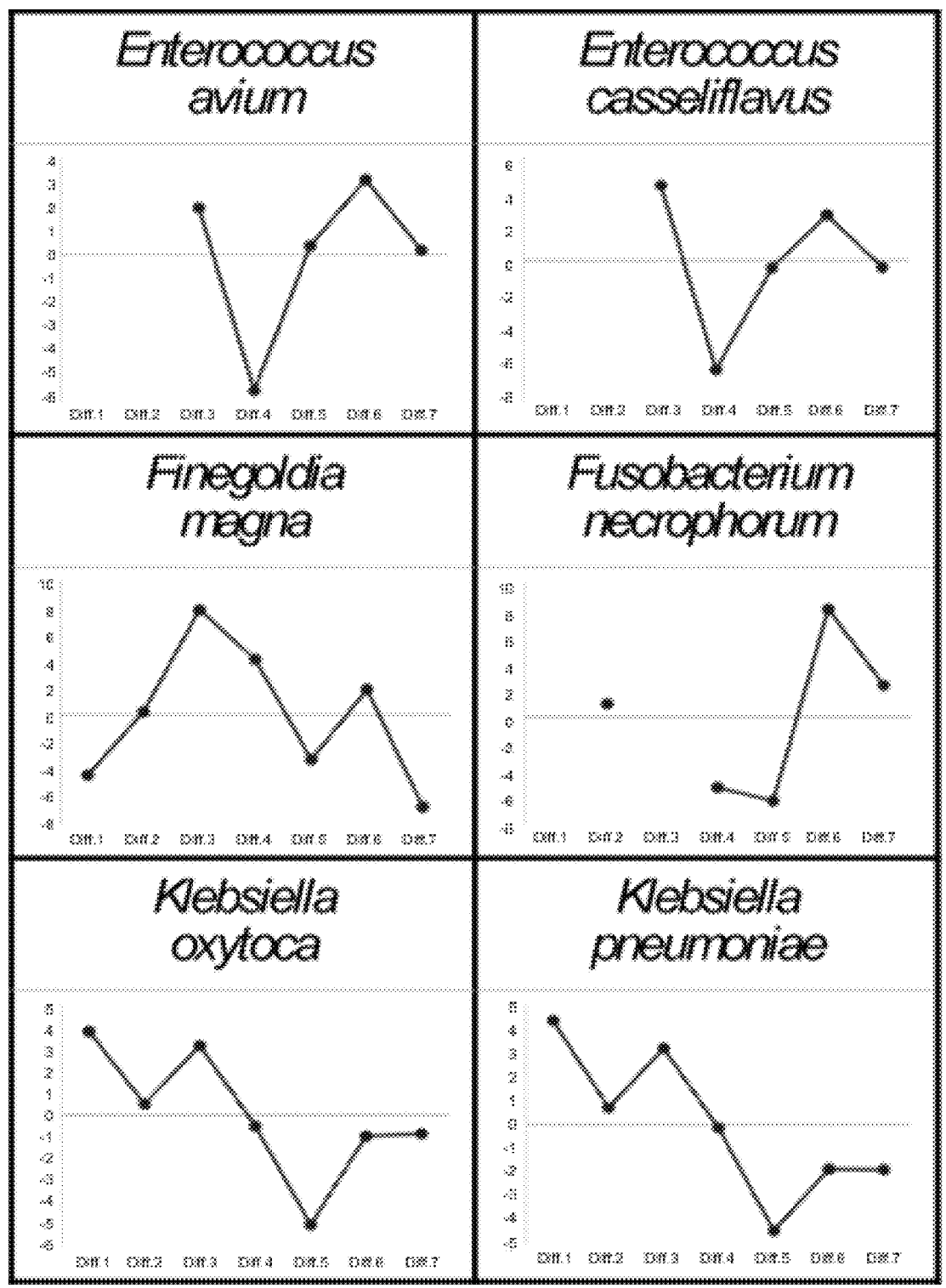
Figure 5G:
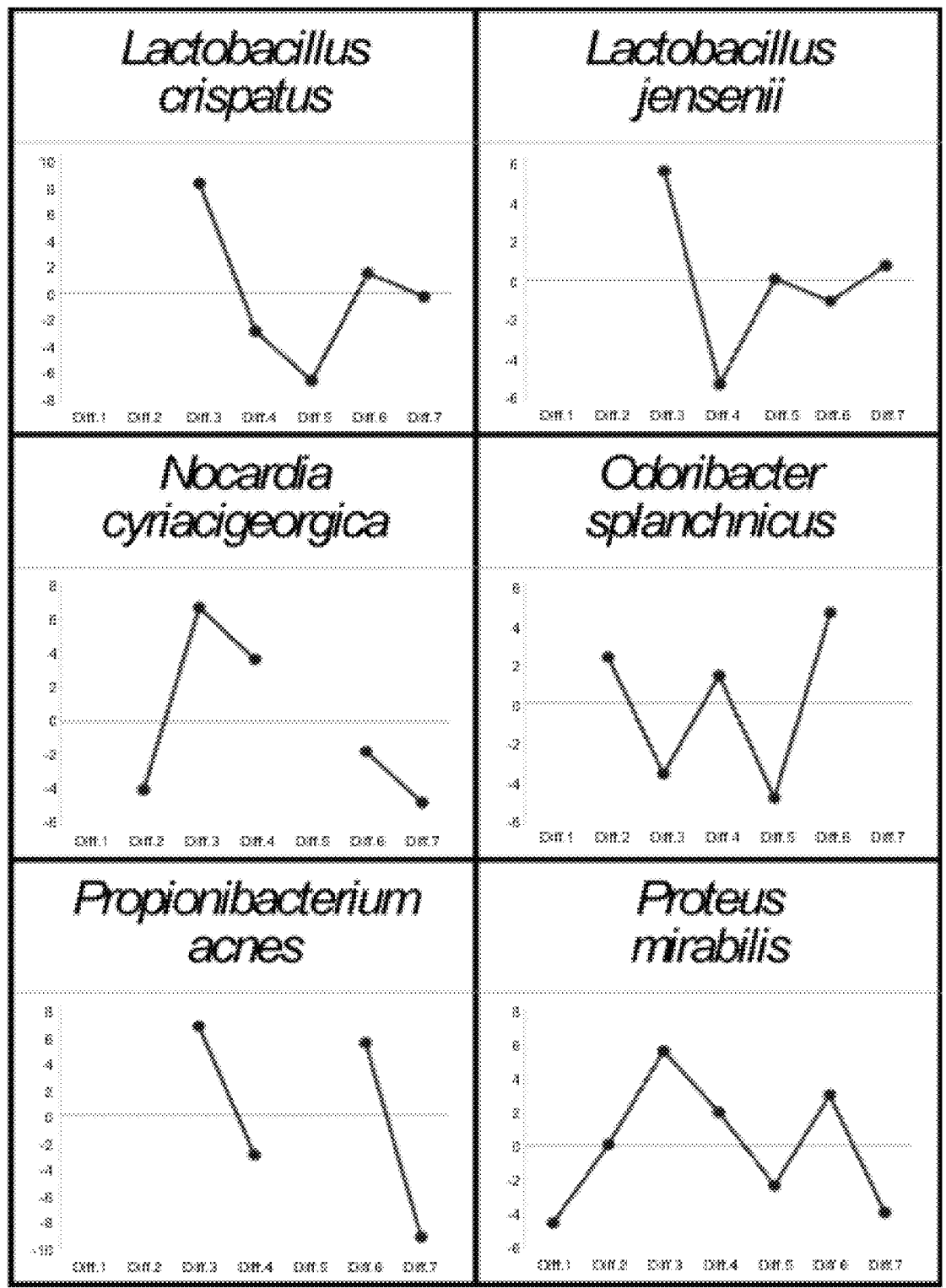
Figure 5H:
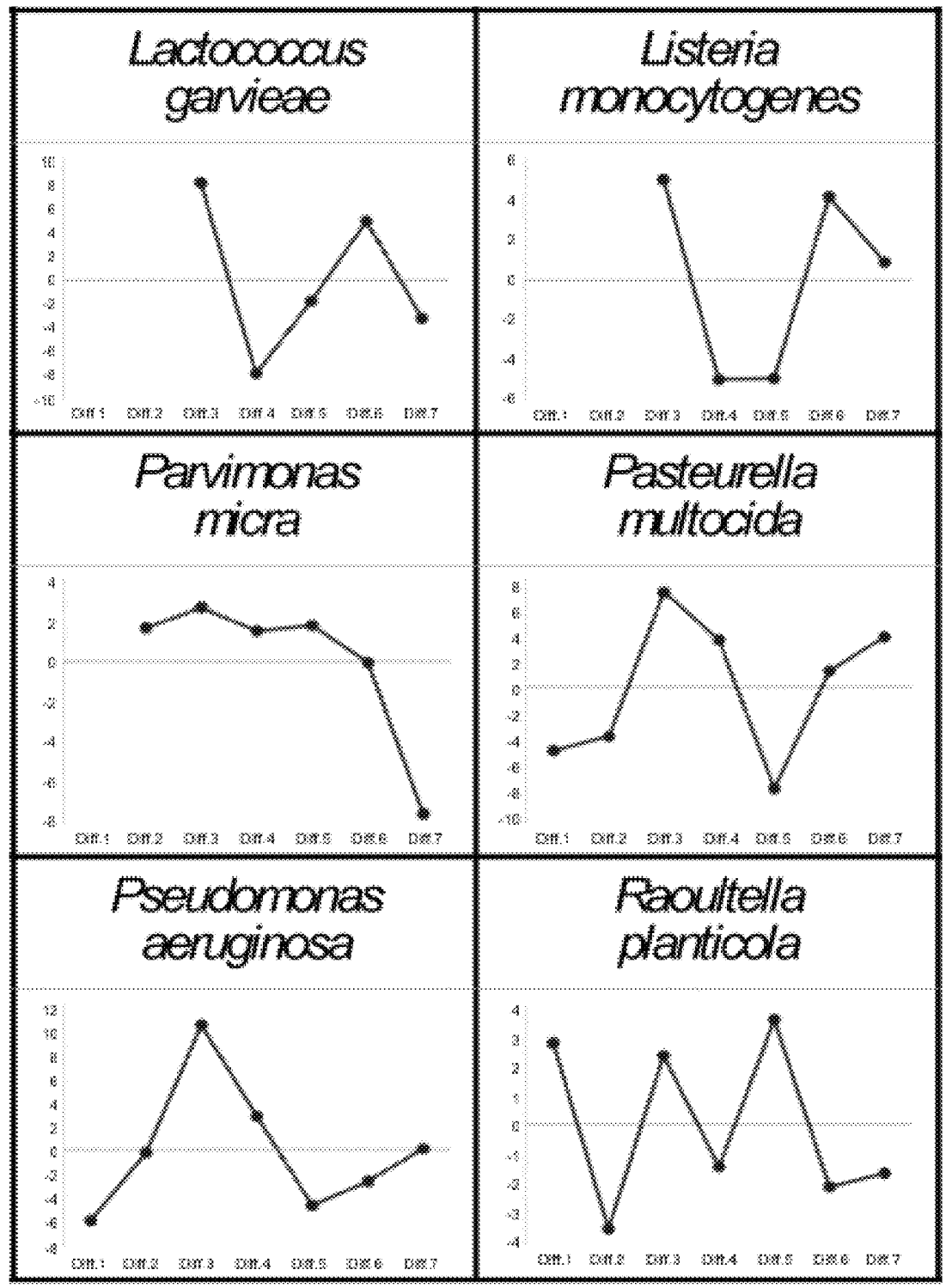
Figure 5I:
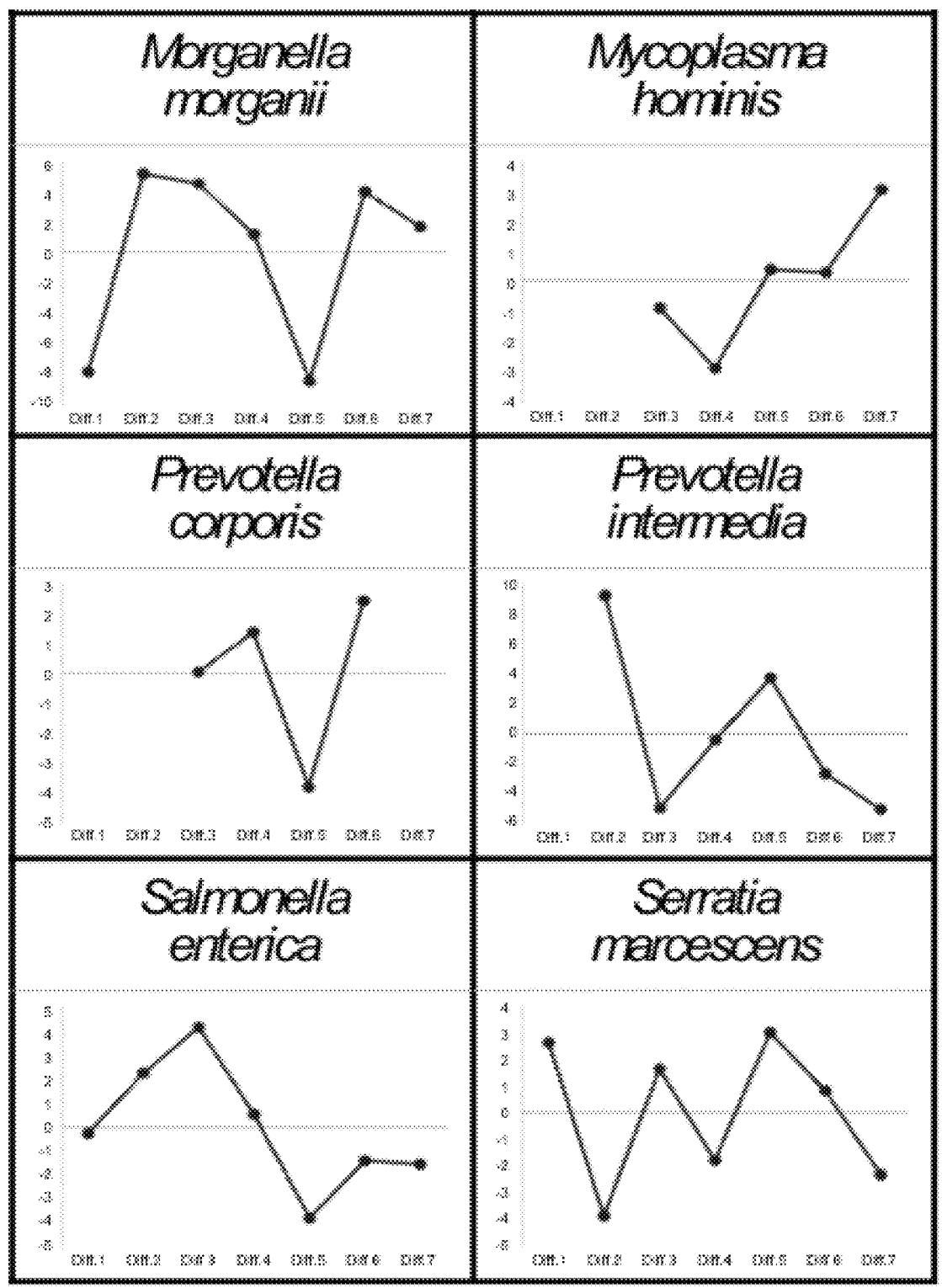
Figure 5J:
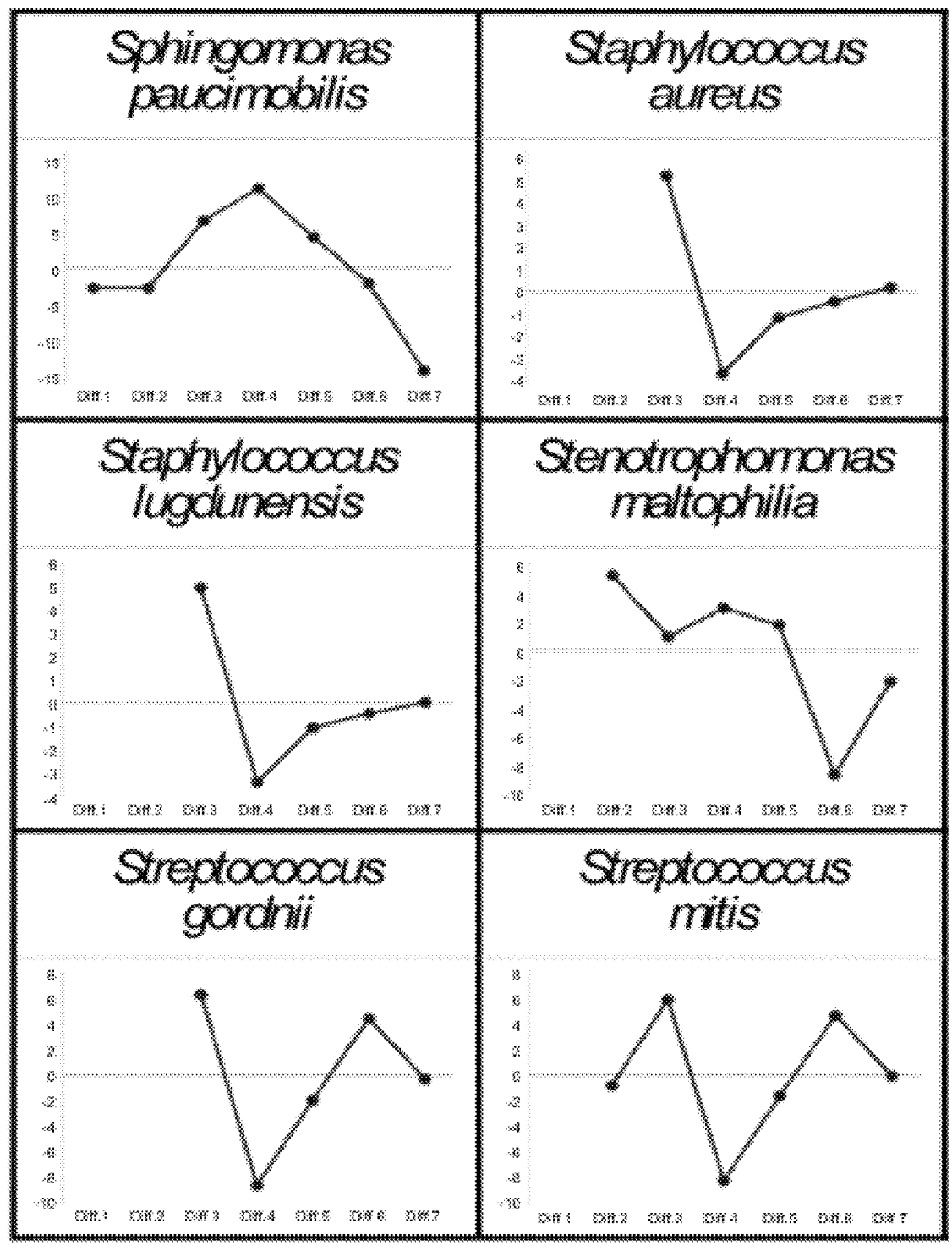
Figure 5K:
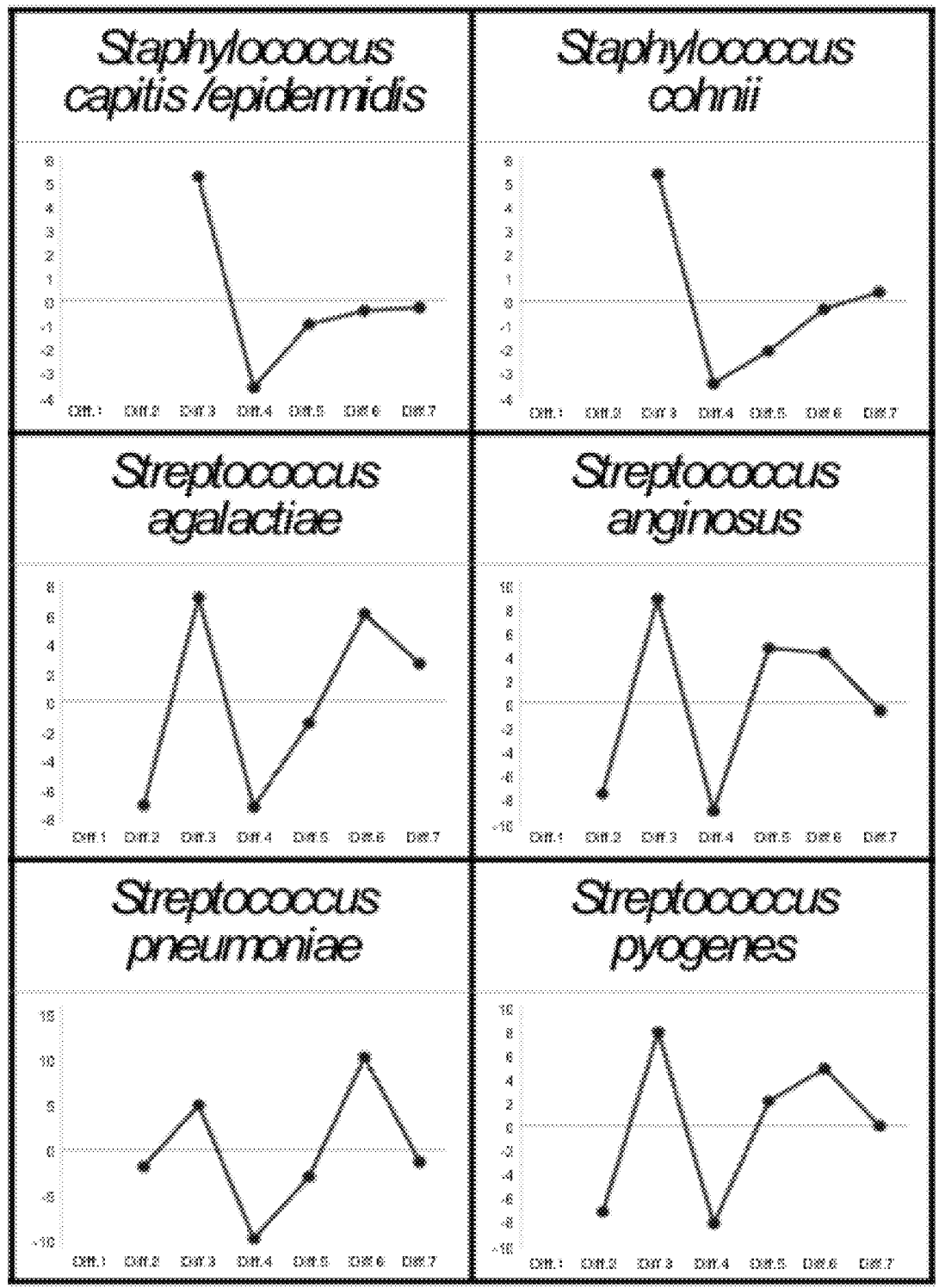
Figure 5L:
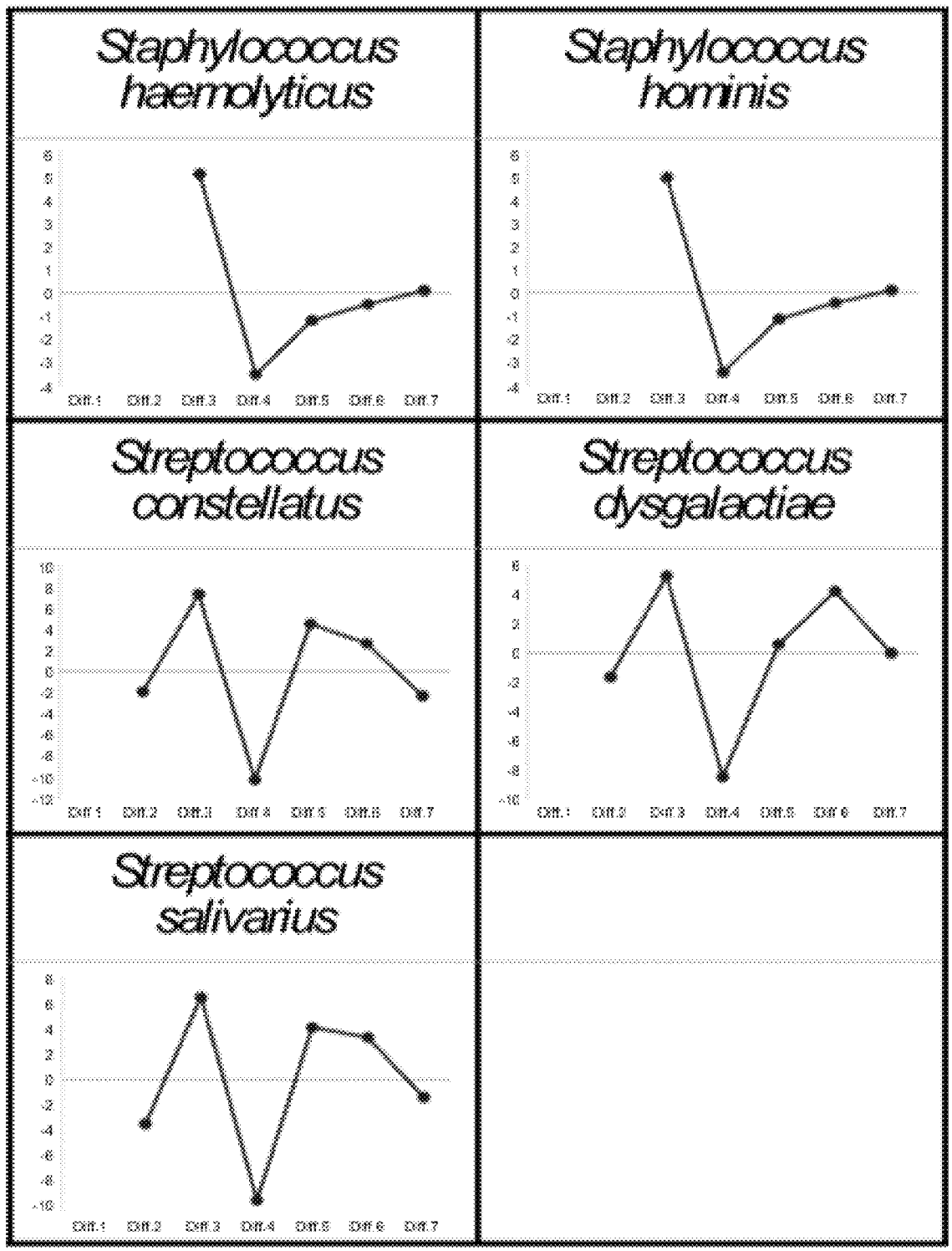

In this step, nested PCR is performed to obtain a plurality of, for example, five PCR amplified products (amplicons) (FIG. 3).

Step (3): Analyzing Tm values of IMLL probes.

For example, two probe targets are located in each of the PCR amplicons of Regions 1 and 3, and a total of 7 (5 types of) PCR amplicons are mixed with seven IMLL probes (FIG. 3 and FIG. 4).

Seven Tm values can be obtained by analyzing the seven IMLL probes.

Step (4): Two-dimensionally mapping a plurality of Tm values.

For example, seven Tm values are two-dimensionally mapped. The shape of plot (Tm mapping shape) indicates a shape specific to a species or genus as shown in FIGS. 5A-5L.

This is not High Resolution Melting-curve (HRM) analysis, but only Tm values are measured.

Step (5): Checking the two-dimensionally mapped "shape" against a database.

The infection-causing pathogenic microorganisms can be rapidly identified by comparing the Tm mapping shape with shapes in the database.

Figure 6:
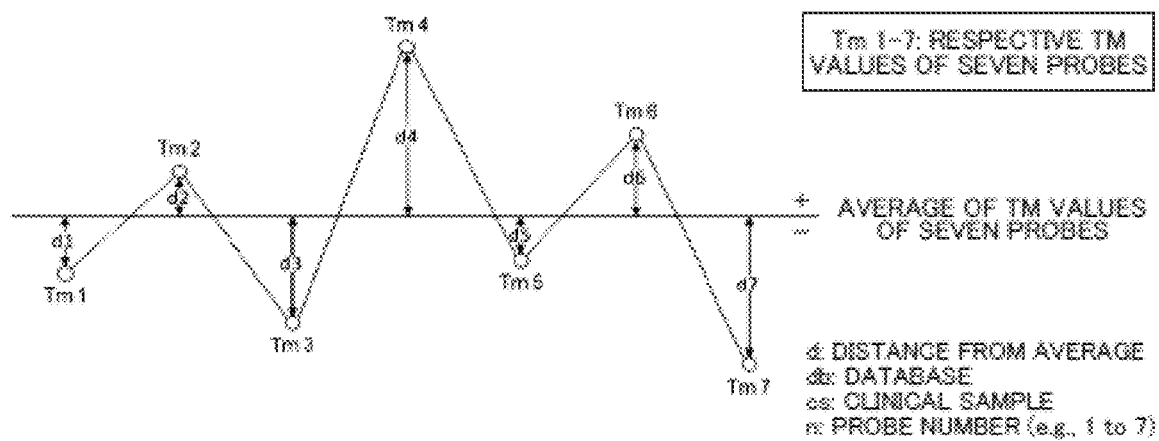
FIG. 6 illustrates an equation calculating the Difference Value. The Difference Value indicates the similarity of a Tm mapping shape to that of the species included in the database.

The degree of similarity with the shapes in the database is expressed quantitatively with the Difference Value calculation equation as shown in FIG. 6.

As the Difference Value is closer to 0, it means that the shapes are more consistent.

The "long probe" of Imperfect-Match Linear Long (IMLL) probe used in the improved Tm mapping method means an oligonucleotide with 35 to 50 bases, preferably 35 to 48 bases, and more preferably 38 to 45 bases.

The difference in Tm values due to the difference in bacterial species of the IMLL probes is up to 20° C. or more.

On the other hand, the difference in Tm values in the conventional Tm mapping method due to the difference in bacterial species is at most about 5° C.

Figure 7:
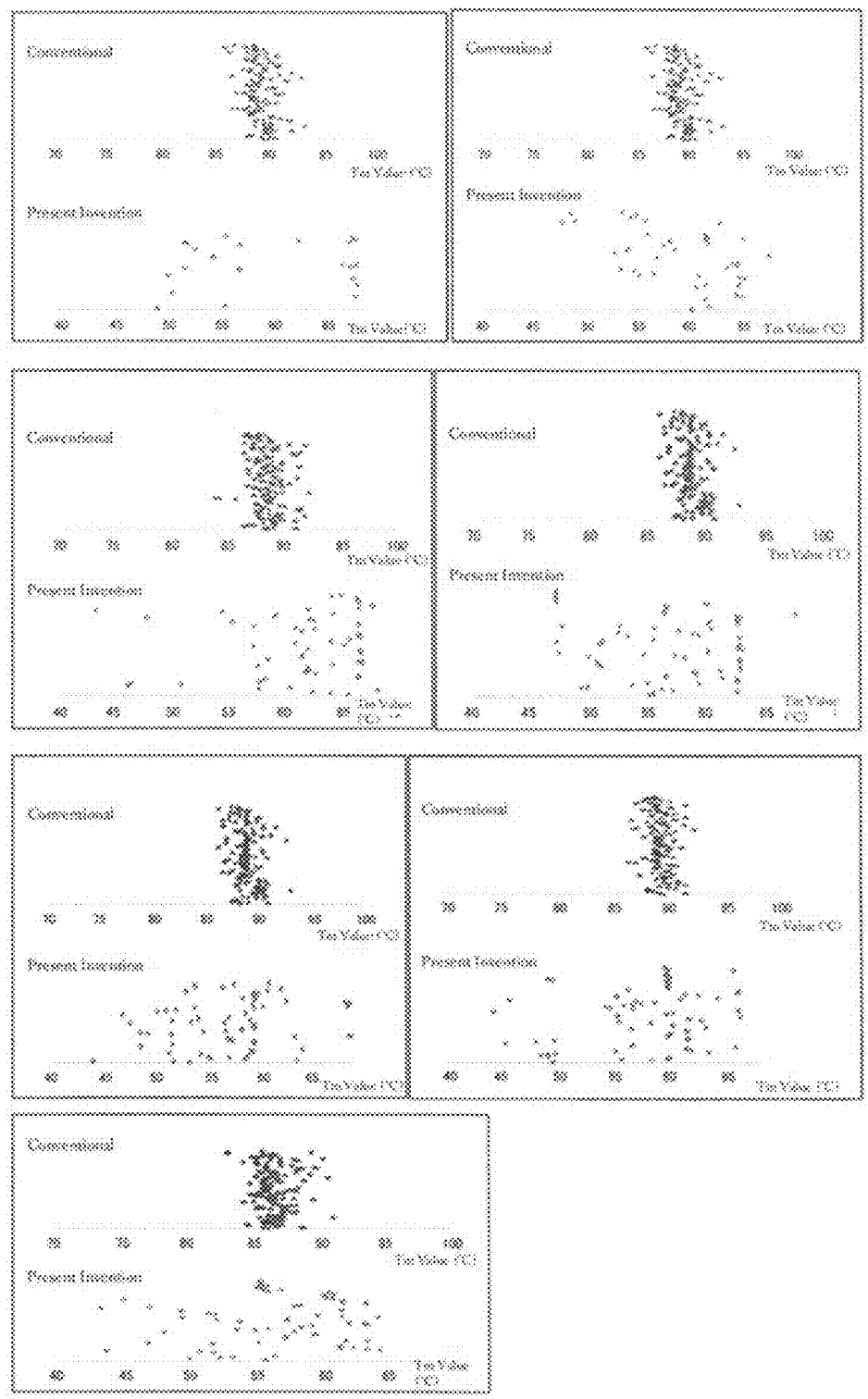
FIG. 7 illustrates differences between the variation range of Tm values from the conventional Tm mapping method and the variation range of Tm values from the improved Tm mapping method.

FIG. 7 illustrates the actual difference between the Tm value variation obtained in the conventional Tm mapping method and the Tm value variation obtained by using IMLL probes in the improved Tm mapping method, in the preliminary database for 71 bacterial species.

Furthermore, an IMLL probe is a probe having a length capable of binding to a site having a mismatch with the target sequence.

By way of example, FIGS. 8A-8E illustrates the mismatches between IMLL probe 1-2 produced below and each of 71 bacterial species included in the preliminary database.

The IMLL probes of the disclosure can bind to target sequences in many bacterial species having different base sequences.

The IMLL probes do not reduce binding to their target sequences because the probes themselves do not form secondary structures despite their long length.

Each of the IMLL probes is designed to have a plurality of sites that bind to, for example, *Escherichia coli* 16S ribosomal RNA (Accession No. AB548582) using a multiple alignment software program (ClustalX) and is chemically synthesized.

For example, the following probes were prepared as specific IMLL probes.

```
IMLL probe 1-1
                                     SEQ ID NO: 1
5'-GTTATCCCACTCTAATAAGCAGGTTACCTACGTATTACTCAC

CC-3':

[probe size: 44 bp, Binding site: positions 84-126 of Escherichia coli 16S rRNA (Accession No. AB548582)]

IMLL probe 1-2
                                     SEQ ID NO: 2
5'-CACCTACTAGCTAATCTTATCTGGGCACATCCGATGGC-3':

[probe size: 38 bp, Binding site: positions 193-230 of Escherichia coli 16S rRNA]
```

-continued

IMLL probe 2-1
SEQ ID NO: 3
5'-CACGCGGCATGGCTCCATCAGGCTTTCCCCCATTGTCGAAGATTC-3':

[probe size: 45 bp, Bindings ite: positions 335-379 of *Escherichia coli* 16S rRNA]

IMLL probe 3-1
SEQ ID NO: 4
5'-CGCCCTGTAATTCCGAATAACGCTAGCTCCCACCGTATTAC-3':

[probe size: 41 bp, Binding site: positions 503-543 of *Escherichia coli* 16S rRNA]

IMLL probe 3-2
SEQ ID NO: 5
5'-CCAAGTTGAGCCCGGGCCTTTCACTACTGACTTAACAAACCGCC-3':

[probe size: 44 bp, Binding site: positions 557-600 of *Escherichia coli* 16S rRNA]

IMLL probe 4-1
SEQ ID NO: 6
5'-GGCACAACCTCTTAATACTCATCGTTTACAGCGTGGAC-3':

[probe size: 38 bp, positions 776-813 of *Escherichia coli* 16S rRNA]

IMLL probe 5
SEQ ID NO: 7
5'-ATCTCTGCAAAGTTCTAAGGATGTCAAGATTAGGTAAGGTTC-3':

[probe size: 42 bp, Binding site: positions 949-990 of *Escherichia coli* 16S rRNA]

Short probe for detecting *S. aureus*
SEQ ID NO: 8
5'-TATCTAATGCAGCGCGGATC-3':

[probe size: 20 bp, Binding site: positions 211-230 of *Staphylococcus aureus* 16S rRNA (Accession No. AB681291)]

The IMLL probes were designed using a multiple alignment software program. The following IMLL probes may be also used depending on target binding sites.

IMLL probe 1-3
SEQ ID NO: 21
5'-CAGACCAGCTAACGATCGTCGCCTTAGTAAGCCGTTACCC-3':

[probe size: 40 bp, Binding site: positions 231-270 of *Escherichia coli* 16S rRNA]

IMLL probe 1-4
SEQ ID NO: 22
5'-CTCAGACCAGCTAACGATCGTTGCCTTAGTAAGCCGTTACCT-3':

[probe size: 42 bp, Binding site: positions 231-272 of *Escherichia coli* 16S rRNA]

IMLL probe 2-2
SEQ ID NO: 23
5'-GTACTTTACAACCCGAAGGCCTTCTTCATACACGCGGCATGGC-3':

[probe size: 43 bp, Binding site: positions 367-409 of *Escherichia coli* 16S rRNA]

IMLL probe 3-3
SEQ ID NO: 24
5'-CCTTATCGCCTTCCTCCCCGCTGAAAGTGCTTTAC-3':

[probe size: 35 bp, Binding site: positions 401-435 of *Escherichia coli* 16S rRNA]

IMLL probe 3-4
SEQ ID NO: 25
5'-CGCCCAGTAATTCCGATTAACGCTTGCACCCTCCGTATTAC-3':

[probe size: 41 bp, Binding site: positions 503-543 of *Escherichia coli* 16S rRNA]

IMLL probe 3-5
SEQ ID NO: 26
5'-GGCCGACTAATTCCGATTAACGCTTCCACGCTCCGTATTAC-3':

[probe size: 41 bp, Binding site: positions 503-543 of *Escherichia coli* 16S rRNA]

IMLL probe 3-6
SEQ ID NO: 27
5'-CTTAACAAACCGCCTACGCACCCTTTAAGCCCAATAATTCCGATTAACGC-3':

[probe size: 50 bp, Binding site: positions 521-570 of *Escherichia coli* 16S rRNA]

IMLL probe 3-7
SEQ ID NO: 28
5'-CTCAAGTTTGCCAGTTTCCGATGAAGTTCCCAGGTTGAGC-3':

[probe size: 40 bp, Binding site: positions 590-629 of *Escherichia coli* 16S rRNA]

IMLL probe 3-8
SEQ ID NO: 29
5'-CTCAAGTTTGCCAGTTTCGGATGCAGTTTCCAGGTTGAGC-3':

[probe size: 40 bp, Binding site: positions 590-629 of *Escherichia coli* 16S rRNA]

IMLL probe 4-2
SEQ ID NO: 30
5'-CCACCTCTATGCAGACATCGTTTACGGCGTGGACTACCAGGG-3':

[probe size: 42 bp, Binding site: positions 768-809 of *Escherichia coli* 16S rRNA]

-continued

IMLL probe 6-1

SEQ ID NO: 31
5'-CCTCCAGTTTGTCATCGGCAGTCTACATTGAGTTCCCAAC-3':

[probe size: 40 bp, Binding site: positions 1112-1151 of *Escherichia coli* 16S rRNA]

IMLL probe 6-2

SEQ ID NO: 32
5'-CCTCCAGTTTGTCACCGGCAGTCTACATTGAGTTCCCAAC-3':

[probe size: 40 bp, Binding site: positions 1112-1151 of *Escherichia coli* 16S rRNA]

IMLL probe 7-1

SEQ ID NO: 33
5'-CTTCATGTAATCAGGTTGCAGACTCCAATCCGGACTAAGACGC-3':

[probe size: 43 bp, Binding site: positions 1265-1307 of *Escherichia coli* 16S rRNA]

IMLL probe 7-2

SEQ ID NO: 34
5'-CTAGCGATTCCGACTTCATGAATACGAGTTGCAGCCTACAAT-3':

[probe size: 42 bp, Binding site: positions 1279-1320 of *Escherichia coli* 16S rRNA]

The universal primers used in step (2) in the improved Tm mapping method of the disclosure may be designed to target a bacterial conserved region so as to universally amplify, for example, seven regions of bacterial 16S ribosomal RNA gene.

Specifically, the universal primers are designed using a multiple alignment software program (Clustal X) and chemically synthesized.

Specific primers are as follows:

```
Primers for first PCR
Forward:
                                        SEQ ID NO: 9
5'-AGAGTTTGATCATGGCTCAG-3':

Reverse:
                                        SEQ ID NO: 10
5'-CCGGGAACGTATTCACC-3':

Region 1 primers for
second PCR (nested PCR)
Forward:
                                        SEQ ID NO: 11
5'-AGAGTTTGATCATGGCTCAG-3':

Reverse:
                                        SEQ ID NO: 12
5'-CGTAGGAGTCTGGACCGT-3':

Region 2 primers for
second PCR (nested PCR)
Forward:
                                        SEQ ID NO: 13
5'-GACTCCTACGGGAGGCA-3':

Reverse:
                                        SEQ ID NO: 14
5'-TATTACCGCGGCTGCTG-3':

Region 3 primers for
second PCR (nested PCR)
Forward:
                                        SEQ ID NO: 15
5'-AGCAGCCGCGGTAATA-3':

Reverse:
                                        SEQ ID NO: 16
5'-GGACTACCAGGGTATCTAATCCT-3':

Region 4 primers for
second PCR (nested PCR)
Forward:
                                        SEQ ID NO: 17
5'-AACAGGATTAGATACCCTGGTAG-3':

Reverse:
                                        SEQ ID NO: 18
5'-AATTAAACCACATGCTCCACC-3':

Region 5 primers for
second PCR (nested PCR)
Forward:
                                        SEQ ID NO: 19
5'-TGGTTTAATTCGATGCAACGC-3':

Reverse:
                                        SEQ ID NO: 20
5'-GAGCTGACGACAGCCAT-3':
```

Construction of Tm Mapping Database Using IMLL Probes

A preliminary database including Tm mapping shapes of 71 bacterial species was first constructed by employing the average of Tm values measured multiple times (e.g., 3 times) in a RotorGeneQ from QIAGEN (thermal variation: ±0.1° C.) (FIGS. 5A-5L).

Bacteria were obtained from clinical samples, and then their base sequences were sequenced. Identification at the species level was achieved.

The amount of data in the database can be changed, and the data can be easily changed and updated.

Each Tm mapping shape in the database reflects the number and position of probe-target mismatches in the hybridization of the IMLL Q probe with a target sequence in each bacterial species.

That is to say, each Tm mapping shape reflects the specific base sequence of each bacterial species and illustrates forms a unique shape.

Some Tm mapping shapes have no data points.

This is due to the fact that some IMLL probes do not bind to their target regions and thus the Tm value at the region cannot be obtained.

To identify pathogenic microorganisms, an identification software program calculates the Difference Value indicating the homology of the Tm mapping shapes and searches for similar patterns of the presence or absence of IMLL probe binding, thereby narrowing down the search range for bacteria in the database.

In other words, the pattern of IMLL probe binding is also utilized as a feature for distinguishing bacterial species.

Evaluation of the accuracy of the Tm mapping method using the IMLL probes (71 bacterial species)

To evaluate the accuracy of the Tm mapping method using the IMLL probes, a blind test was performed using bacterial DNAs of the same 71 bacterial species registered in the preliminary database in a RotorGeneQ from QIAGEN (thermal variation: ±0.1° C.).

That is to say, the bacterial DNAs were identified with the bacterial names hidden. The tests of 71 bacterial species failed to narrow down the Tm mapping results at the species level (*Staphylococcus aureus* or *Staphylococcus hemolyticus* or *Staphylococcus hominis* or *Staphylococcus lugdunensis*) in the genus *Staphylococcus*.

Similarly, it was impossible to distinguish between *Enterococcus faecalis* and *Enterococcus faecium* and identify them.

The results from Tm mapping shapes for the remaining 65 bacterial species were consistent with the results from sequenced bacterial DNAs in the database.

The Difference Values averaged 0.242 and ranged from 0.09 to 0.30 (standard deviation=0.08).

Evaluation of the similarity of Tm mapping shapes of 71 bacterial species in the preliminary database The evaluation is shown in Table 1 (FIGS. 9A-9E).

The defined Difference Value reflects the difference between each bacterial species registered in the database of Tm mapping shapes and other bacterial species.

As the Difference Value is closer to zero, the Tm mapping shapes are more similar to the shapes for bacterial species registered in the database.

If a measurement error of Tm values between PCR tubes in a measuring instrument (=thermal variation of the measuring instrument) is within ±0.1° C., the measurement error range of the Difference Values will be within 0.28.

Similarly, if a measurement error of Tm values between PCR tubes in a measuring instrument is within ±0.2° C., ±0.3° C., ±0.4° C., ±0.5° C., and ±0.6° C., the measurement error range of the Difference Values will be within 0.53, 0.80, 1.06, 1.33, and 1.59, respectively.

The similarity of bacterial species to each other was analyzed by using the Difference Values, which demonstrates that it is impossible to distinguish between *Enterococcus faecalis* and *Enterococcus faecium*.

It is also revealed that identification at the species level is difficult in the genus *Staphylococcus*.

Since Difference Values of the other 65 bacterial species to each other have 1.33 or more, it is found that use of a measuring instrument with a thermal variation (measurement error of Tm values between PCR tubes) within ±0.5° C. allows identification accurate at least at the genus level and often at the species level.

That is to say, although the conventional Tm mapping method allows only a measuring instrument having measurement errors of Tm values between PCR tubes within ±0.1° C., the disclosure significantly expands the scope of instruments capable of performing the Tm mapping method.

For example, seven IMLL probes (SEQ ID NOS: 1 to 7) were used to first construct a preliminary database of Tm mapping shapes for 71 bacterial species. As a result, it was shown that microorganisms can be accurately distinguished and identified at least at the genus level and often at the species level even in a real-time PCR instrument having measurement errors of Tm values between PCR tubes within ±0.5° C.

Since most of the current commercial real-time PCR instruments have a measurement error between PCR tubes within ±0.3° C., the Tm mapping method can be performed in almost all instruments when the IMLL probes are used.

By using 14 whole blood samples (in 2 mL EDTA blood collection tubes) collected from patients with sepsis, the accuracy of the Tm mapping method using the IMLL probe (SEQ ID NOS: 1 to 7) was compared with that of the conventional culture method to perform evaluation.

A RotorGeneQ (thermal variation: ±0.1° C.) from QIAGEN was used as a real-time PCR instrument, and a preliminary database including 71 bacterial species was used as a database of pathogenic microorganisms.

Table 2 (FIGS. 10A-10B) shows a comparison between the individual identification results of pathogenic microorganisms using the Tm mapping method with the IMLL probes and the identification results from the culture method or the sequencing method.

When the identification results of pathogenic microorganisms from the Tm mapping method were inconsistent with the results from the culture method, the sequencing method was used to identify the bacterial species again. The Tm mapping method was used to identify pathogenic microorganisms in a total of 14 samples, and the obtained results were consistent with the results from the culture method or sequencing method in all of the 14 samples (14/14).

However, when pathogenic microorganisms are identified to belong to the genus *Staphylococcus* in the method using IMLL probes, an additional test is performed using a short probe for detecting *S. aureus* to determine whether the pathogenic microorganisms are *S. aureus* or other species belonging to the genus *Staphylococcus* (=CNS) (this additional test can be completed in only about 10 minutes).

Seven IMLL probes of the disclosure (SEQ ID NOS: 1 to 7) were then used to construct an extensive database including Tm mapping shapes of 146 bacterial species by employing the average of Tm values measured multiple times (e.g., 3 times) in a RotorGeneQ from QIAGEN (thermal variation: ±0.1° C.).

The registered 145 bacterial species (65 bacterial genera) are as follows: *Achromobacter xylosoxidans, Acinetobacter baumanii, Acinetobacter calcoaceticus, Aeromonas hydrophila, Alistipes onderdonkii, Anaerococcus vaginalis, Arthrobacter cumminsii, Bacillus cereus, Bacillus coagulans, Bacillus licheniformis, Bacillus megaterium, Bacillus pumilus, Bacillus subtilis* subsp. *Subtilis, Bacteroides dorei, Bacteroides finegoldii, Bacteroides fragilis, Bacteroides nordii, Bacteroides salyersiae, Bacteroides thetaiotaomicron, Bacteroides uniformis, Bacteroides vulgatus, Bartonella henselae, Bifidobacterium bifidum, Bilophila wadsworthia, Bordetella pertussis, Borrelia burgdorferi, Brevibacillus laterosporus, Campylobacter coli, Campylobacter jejuni* subsp. *jejuni, Campylobacter rectus, Capnocytophaga gingivalis, Capnocytophaga granulosa, Capnocytophaga haemolytica, Capnocytophaga ochracea, Capnocytophaga sputigena, Chryseobacterium gleum, Citrobacter amalonaticus, Citrobacter freundii, Clostridium difficile, Clostridium histolyticum, Clostridium hylemonae, Clostridium paraputrificum, Clostridium perfringus, Clostridium sporogenes, Clostridium subterminal, Clostridium tertium, Corynebacterium amycolatum, Corynebacterium macginleyi, Corynebacterium striatum, Corynebacterium xerosis, Eggerthella lenta, Eikenella corrodens, Empedobacter brevis, Enterobacter aerogenes, Enterobacter cloacae* subsp. *cloacae, Enterococcus avium, Enterococcus casseliflavus, Enterococcus durans, Enterococcus faecalis, Enterococcus faecium, Enterococcus gallinarum, Enterococcus raffinosus, Escherichia albertii, Escherichia coli, Eubacterium limosum, Finegoldia magna, Fusobacterium necrophorum, Fusobacterium periodonticum, Fusobacterium varium, Gardnerella vaginalis, Gemella morbillorum, Geobacillus stearothermophilus, Haemophilus influenzae, Halmonas venusta, Klebsiella oxytoca, Klebsiella pneumoniae, Kocuria rosea, Lactobacillus acidophilus, Lactobacillus crispatus, Lactobacillus fermentum, Lactobacillus jensenii, Lactococcus garvieae, Legionella pneumophila* subsp. *pneumophila, Leptospira interrogans* serovar *Copenhageni, Listeria monocytogenes, Micrococcus luteus, Morganella morganii, Nocardia cyriacigeorgica, Odoribacter splanchinicus, Pantoea agglomerans, Parvimonas micra, Pasteurella multocida, Peptoniphilus asaccharolyticus, Peptoniphilus gorbachii, Peptostreptococcus anaerobius, Plesiomonas shigelloides, Porphyromonas gingivalis, Prevotella corporis, Prevotella intermedia, Prevotella melaninogenica, Prevotella timonen-* sis, *Prevotella veronalis, Propionibacterium acnes, Propionibacterium granulosum, Proteus mirabilis, Proteus vulgaris, Pseudomonas aeruginosa, Pseudomonas fluorescens, Pseudomonas putida, Salmonella enterica, Serratia marcescens, Serratia plymuthia, Staphylococcus aureus, Staphylococcus capitis/epidermidis, Staphylococcus cohnii, Staphylococcus haemolyticus, Staphylococcus hominis, Staphylococcus intermedius, Staphylococcus lugdunensis, Staphylococcus saprophyticus* subsp. *saprophyticus, Staphylococcus schleiferi* subsp. *coagulans, Staphylococcus simulans, Staphylococcus warneri, Stenotrophomonas maltophilia, Streptobacillus moniliformis, Streptococcus agalactiae, Streptococcus anginosus, Streptococcus bovis, Streptococcus constellatus, Streptococcus dysgalactiae, Streptococcus gallolyticus* subsp. *pasteurianus, Streptococcus gordonii, Streptococcus intermedius, Streptococcus mitis, Streptococcus orali, Streptococcus pneumoniae, Streptococcus pyogenes, Streptococcus salivarius, Streptococcus sanguinis, Tannerella forsythus, Treponema denticola, Vibrio fluvialis, Vibrio vulnificus, Yersinia enterocolitica* subsp. *enterocolitica, Yersinia pseudotuberculosis*

Evaluation of the Accuracy of the Tm Mapping Method Using IMLL Probes (145 Bacterial Species)

Next, the accuracy of the Tm mapping method using IMLL probes is evaluated in more detail. To achieve this, an extensive database was first constructed using bacterial DNAs from 145 species (65 bacterial genera). The same bacterial DNAs registered in the database including 145 bacterial species was then used to perform a blind test in a Light Cycler® 480 (thermal variation: ±0.4° C.) from Roche Life Science.

That is to say, the bacterial DNAs were identified using the Tm mapping method with IMLL probes, with the bacterial names hidden.

The results are shown in Table 3-1 (FIGS. 11A-11G) and Table 3-2 (FIGS. 12A-12E).

In the blind test results, 115 of 145 bacterial species were correctly identified at the species level, and all of 65 bacterial genera were correctly identified at the genus level. It was known that at the time of constructing the database, 30 bacterial species incorrectly identified at the species level were unable to be distinguished among the bacteria belonging to the same genus in an instrument with thermal variation of ±0.4° C.

In other words, the results were as expected.

The microorganisms that cannot be correctly identified at the species level in an instrument with thermal variation of ±0.4° C. were 3 of 6 bacterial species in the genus *Bacillus*, 2 of 8 bacterial species in the genus *Bacteroides*, 2 of 3 species in the genus *Campylobacter*, 2 of 4 bacterial species in the genus *Corynebacterium*, 5 of 7 bacterial species in the genus *Enterococcus*, 2 of 2 bacterial species in the genus *Proteus*, 9 of 11 bacterial species in the genus *Staphylococcus*, and 5 of 14 bacterial species in the genus *Streptococcus*.

The above results demonstrated that even when an instrument with thermal variation of ±0.4° C. was used, 65 bacterial genera were able to be correctly identified at the genus level, and 115 of 145 species were able to be correctly identified at the species level.

Antimicrobial agents can be selected in most cases if the pathogenic microorganisms can be rapidly identified at least at the genus level. When identification at the species level is required, a species-specific short probe may be used.

After the genus is known, an additional test of about 10 minutes can be performed using a selected short probe to identify bacterial species at the species level.

Finally, by using 40 whole blood samples (in 2 mL EDTA blood collection tubes) (9 bacterial species) collected from patients with sepsis, the accuracy of the Tm mapping method using the IMLL probe (SEQ ID NOS: 1 to 7) was compared with that of the conventional culture method to perform evaluation.

A Light Cycler® 480 (thermal variation: ±0.4° C.) from Roche Life Science was used as a real-time PCR instrument, and a database including 145 bacterial species was used as a pathogenic microorganism database.

Table 4 (FIGS. 13A-13C) illustrates a comparison between the individual identification results of pathogenic microorganisms using Tm mapping methods with the IMLL probes and those using the culture method or the sequencing method.

When the identification results of pathogenic microorganisms using the Tm mapping method merely narrowed down the pathogenic microorganisms to the genus *Staphylococcus*, a short probe for detecting *S. aureus* was additionally used to determine whether the microorganisms are *S. aureus* or other species except *S. aureus* belonging to the genus *Staphylococcus* (CNS).

The Tm mapping method was used to identify pathogenic microorganisms in a total of 40 samples, and the obtained results were consistent with the results from the conventional culture method in 39 samples (39/40).

However, when a plurality of microorganisms is detected in the culture method, only numerically dominant microorganisms are identified in the Tm mapping method.

When the plurality of microorganisms was almost equally present (sample No. 40), the Tm mapping method failed to identify them, and the result was considered inconsistent.

The above results demonstrated that even when an instrument with thermal variation of ±0.4° C. was used, 39 of 40 samples (9 bacterial species) from patients with sepsis were able to be correctly identified.

Antimicrobial agents can be selected in most cases if the pathogenic microorganisms can be rapidly identified at least at the genus level. However, when identification at the species level is required, a species-specific short probe such as a short probe for detecting *S. aureus* in the above case may be used.

After the genus is known, an additional test of about 10 minutes can be performed using a selected short probe to identify bacterial species at the species level.

Next, the improved Tm mapping method using linear long probes of imperfect-match sequences of the disclosure will be described in the Examples.

It should be noted that probes according to the disclosure are expressed as Imperfect-Match Linear Long (IMLL) probes.

The overall flow (workflow) is shown in FIG. 2.

The blood samples were whole blood collected from patients with suspected sepsis at Toyama University Hospital and Nagaresugi Hospital. All procedures in the Examples described below were performed under approval from the Ethics Committee at the University of Toyama and with written informed consent obtained from all patients. The methods performed in the Examples were carried out in accordance with the approved guidelines.

EXAMPLES

Example 1

Isolation of Bacterial Genomic DNA from Whole Blood

For example, blood is collected from vein into an EDTA blood collection tube and gently centrifuged (100×g) to separate blood cells and obtain a supernatant. The supernatant is transferred to a tube and strongly centrifuged (20,000×g) to obtain a bacterial pellet.

Specifically, 2 mL of venous blood was collected in an EDTA tube (EDTA-2K vacuum blood collection tube, NIPRO CORPORATION).

The blood sample was then centrifuged at 100×g for 5 minutes to spin down blood cells, and the resulting supernatant fraction (1 mL, with buffy coat) was used.

The supernatants were centrifuged again at 20,000×g for 10 minutes, and the resulting supernatant fractions were carefully removed so as not to disturb the pellets.

Next, 1 mL of molecular-grade distilled water (water deionized and sterilized for molecular biology, hereinafter referred to as sterile water, NACALAI TESQUE, INC.) was added, and the mixture was gently turned upside down and subsequently centrifuged at 20,000×g for 5 minutes.

Then, the supernatant fractions were again carefully removed so that the pellets were not resuspended before using a DNA extraction kit.

Next, DNA was isolated from the pellets using a DNA extraction kit (QIAamp UCP Pathogen Mini Kit, Qiagen, Germany) in accordance with the supplier's protocols.

Finally, bacterial DNA was eluted with 100 µL of elution buffer.

Isolation of Bacterial Genomic DNA from Bacterial Colonies

Bacterial colonies were picked up with a sterile inoculating loop and suspended in 1 mL of sterile water.

The suspensions were subsequently centrifuged at 20,000×g for 10 minutes followed by removal of the supernatants to obtain pellets.

DNA was isolated from the resulting pellets using a DNA extraction kit (QIAamp UCP Pathogen Mini Kit, Qiagen) in accordance with the supplier's protocols. Finally, bacterial DNA was eluted with 100 µL of elution buffer.

PCR Assays

A Veriti™ Thermal Cycler (Applied Biosystems) was used for amplification, and a LightCycler Nano (Roche Applied Science) was used for Tm value analysis of IMLL probes.

When using a LightCycler Nano that has two independent thermal blocks, the same thermal block is preferably used for all seven PCR tubes to identify pathogenic microorganisms using the Tm mapping method.

All PCR assays were performed as single-tube assays (no multiplex PCR).

RNase- and DNase-free PCR tubes (Eppendorf, Germany), 0.2 mL PCR tubes (Qiagen) were used for the first PCR [PCR (one tube)], and 0.1 mL Strip Tubes and Caps (Qiagen) were used for the nested PCR [Nested PCR (five tubes)].

All oligonucleotide primers were designed using a multiple alignment software program (Clustal X) and were synthesized by Life Technologies Japan Ltd. (Tokyo, Japan).

Quenching probes (Q-probes) were adopted as IMLL probes in the Example.

All quenching probes were designed using a multiple alignment software (Clustal X) and synthesized by NIPPON STEEL Eco-Tech Corporation (Tsukuba, Japan).

Bacterial universal primers were designed to universally amplify seven regions of bacterial 16S ribosomal RNA gene (FIG. 3).

```
First PCR primers
Forward:
                                      (SEQ ID NO: 9)
5'-AGAGTTTGATCATGGCTCAG-3'

Reverse:
                                      (SEQ ID NO: 10)
5'-CCGGGAACGTATTCACC-3'

(Amplicon size: 1378 bp)

Region 1 primers for second PCR
(nested PCR)
Forward:
                                      (SEQ ID NO: 11)
5'-AGAGTTTGATCATGGCTCAG-3'

Reverse:
                                      (SEQ ID NO: 12)
5'-CGTAGGAGTCTGGACCGT-3'

(Amplicon size: 338 bp)

Region 2 primers for second PCR
(nested PCR)
Forward:
                                      (SEQ ID NO: 13)
5'-GACTCCTACGGGAGGCA-3'
Reverse:
                                      (SEQ ID NO: 14)
5'-TATTACCGCGGCTGCTG-3'

(Amplicon size: 199 bp)

Region 3 primers for second PCR
(nested PCR)
Forward:
                                      (SEQ ID NO: 15)
5'-AGCAGCCGCGGTAATA-3'
Reverse:
                                      (SEQ ID NO: 16)
5'-GGACTACCAGGGTATCTAATCCT-3'
(Amplicon size: 287 bp)

Region 4 primers for second PCR
(nested PCR)
Forward:
                                      (SEQ ID NO: 17)
5'-AACAGGATTAGATACCCTGGTAG-3'
Reverse:
                                      (SEQ ID NO: 18)
5'-AATTAAACCACATGCTCCACC-3'
(Amplicon size: 181 bp)

Region 5 primers for second PCR
(nested PCR)
Forward:
                                      (SEQ ID NO: 19)
5'-TGGTTTAATTCGATGCAACGC-3'
Reverse:
                                      (SEQ ID NO: 20)
5'-GAGCTGACGACAGCCAT-3'
(Amplicon size: 120 bp)
```

Seven Q-probes described below that bind to each of five amplicons obtained from the nested PCR using the bacterial universal primers described above were designed (FIG. 3 and FIG. 4).

IMLL probe 1-1
(SEQ ID NO: 1)
5'-GTTATCCCACTCTAATAAGCAGGTTACCTACGTATTACTCACCC-3'

[probe size: 44 bp, Binding site: positions 84-126 of *Escherichia coli* 16S rRNA (Accession No. AB548582)]

IMLL probe 1-2
(SEQ ID NO: 2)
5'-CACCTACTAGCTAATCTTATCTGGGCACATCCGATGGC-3'

[probe size: 38 bp, Binding site: positions 193-230 of *Escherichia coli* 16S rRNA]

IMLL probe 2-1
(SEQ ID NO: 3)
5'-CACGCGGCATGGCTCCATCAGGCTTTCCCCCATTGTCGAAGATTC-3'

[probe size: 45 bp, Binding site: positions 335-379 of *Escherichia coli* 16S rRNA]

IMLL probe 3-1
(SEQ ID NO: 4)
5'-CGCCCTGTAATTCCGAATAACGCTAGCTCCCACCGTATTAC-3'

[probe size: 41 bp, Binding site: positions 503-543 of *Escherichia coli* 16S rRNA]

IMLL probe 3-2
(SEQ ID NO: 5)
5'-CCAAGTTGAGCCCGGGCCTTTCACTACTGACTTAACAAACCGCC-3'

[probe size: 44 bp, Binding site: positions 557-600 of *Escherichia coli* 16S rRNA]

IMLL probe 4-1
(SEQ ID NO: 6)
5'-GGCACAACCTCTTAATACTCATCGTTTACAGCGTGGAC-3'

[probe size: 38 bp, positions 776-813 of *Escherichia coli* 16S rRNA]

IMLL probe 5
(SEQ ID NO: 7)
5'-ATCTCTGCAAAGTTCTAAGGATGTCAAGATTAGGTAAGGTTC-3'

[probe size: 42 bp, Binding site: positions 949-990 of *Escherichia coli* 16S rRNA]

Short probe for detecting *S. aureus*
SEQ ID NO: 8
5'-TATCTAATGCAGCGCGGATC-3':

[probe size: 20 bp, Binding site: positions 211-230 of *Staphylococcus aureus* 16S rRNA (Accession No. AB681291)]

Procedure of the First PCR

A composition of a PCR reaction mixture (20 μL) was as follows: 200 μM of each Hot Start dNTP (CleanAmp™ Hot Start dNTP Mix, Sigma-Aldrich, USA: filtered through an Amicon Ultra 50 K centrifugal filter (Merck Millipore, Germany) before use), 2 μL of DNA template, 50 mM potassium chloride, 2.25 mM magnesium chloride, 10 mM Tris-HCl buffer (pH 8.3), 0.3 μM each primer, and 1.0 unit (0.5 μL) of "a thermostable DNA polymerase prepared using a eukaryote as a host cell" and dissolved in a stock buffer.

This PCR reaction mixture (20 μL) was used to perform the first PCR.

Generation of "the thermostable DNA polymerase prepared using a eukaryote as a host cell" using *Saccharomyces cerevisiae* was performed according to a known method.

In place of 2 μL of a DNA template, 2 μL (8.0 ng/μL) of DNA extracted from *Escherichia coli* (ATCC 25922) was used as a positive control, or 2 μL of sterile water (NACALAI TESQUE, INC.) was used as a negative control.

Each sample was incubated for 5 minutes at 95° C. to activate the Hot Start dNTPs followed by denaturation at 94° C. for 10 seconds, annealing at 57° C. for 10 seconds, and 40 cycles of extension at 72° C. for 30 seconds.

The resulting PCR products were diluted 100-fold with sterile water (NACALAI TESQUE, INC) and then used as a template for the second (nested) PCR.

Procedure of the Second (Nested) PCR

A composition of a PCR reaction mixture (20 μL) was as follows: 200 μM of each Hot Start dNTP (CleanAmp™ Hot Start dNTP Mix, Sigma-Aldrich, USA: filtered through an Amicon Ultra 50 K centrifugal filter (Merck Millipore, Germany) before use), 2 μL of a DNA template that was a 100-fold diluted 1st PCR product, 50 mM potassium chloride, 2.25 mM magnesium chloride, 10 mM Tris-HCl buffer (pH 8.3), 0.75 μM each forward primer, 0.25 μM each reverse primer, and 1.0 unit (0.5 μL) of "a thermostable DNA polymerase prepared using a eukaryote as a host cell" and dissolved in a stock buffer.

Each of seven PCR reaction mixtures used for the amplification of Regions 1 to 5 (20 μL) was incubated for 5 minutes at 95° C. to activate the Hot Start dNTPs followed by denaturation at 94° C. for 10 seconds, annealing at 57° C. for 10 seconds, and extension at 72° C. for 10 seconds. Thirty cycles were performed.

Tm Value Analysis

Eight μL was taken from 20 μL of the amplified product from the second PCR, and mixed with 0.12 μM IMLL Q-probe (a total of 10 μL).

As a previous step for a Tm value analysis, the resulting seven mixtures were heated at 95° C. for 5 minutes, gradually cooled at 4° C./second, and then kept at 40° C. for 1 minute.

A Tm value analysis was performed at temperatures ranging from 40° C. to 80° C. while the temperature was increased at 0.1° C./step.

The data profile was subsequently analyzed using a Light-Cycler® Nano software program to determine Tm values.

Determination of the Sensitivity of Pathogenic Microorganism Identification

Limits of identification and detection of microorganisms performed by using the Tm mapping method with IMLL probes were measured as described below. A known count (CFU) of *Escherichia coli* (*E. coli*) was suspended in phosphate-physiological saline and serially diluted ($\log^2$-fold). In each diluted suspension, identification was then performed using the Tm mapping method with IMLL Q probes.

The limit of identification was determined under the definition in which "the limit is the lowest $\log^2$ dilution in the dilution series where identification results from the Tm mapping method (Difference Value is 0.5 or less) are correct."

The limit of detection (LOD) was determined under the definition in which "the limit is the final $\log^2$ dilution of DNA template where at least one of seven Tm values is measured."

Bacterial species identification based on bacterial genomic DNA sequences using the sequencing method An amplicon from samples used in the first PCR procedure was purified (QIAquick PCR Purification Kit; QIAGEN) and then sequenced (3500 Genetic Analyzer; Applied Biosystems) using Region 1 forward primer and Region 5 reverse primer to determine the base sequence.

Bacterial species identification based on bacterial genomic DNA sequences was performed through an online homology search for bacterial species using the BLAST nucleotide database tool of the DNA Data Bank of Japan (http://www.ddbj.nig.ac.jp/index-j.html).

Biochemical Identification of Bacteria Using the Conventional Culture Method

Whole blood samples for culture (one aerobic blood culture bottle and one anaerobic blood culture bottle) were collected simultaneously with blood samples for Tm value analysis from the same puncture site.

In the biochemical identification of bacteria, the whole blood samples were analyzed according to standard methods used by the Department of Clinical Laboratory (certified ISO15189) at Toyama University Hospital.

The blood culture procedures were performed using a BacT/ALERT 3D system (bioMerieux, Inc., Mercy-l'Etoile, France).

Positive blood in blood culture bottles was subcultured in an appropriate medium and incubated aerobically or anaerobically until sufficient growth was achieved (usually 18 to 24 hours).

Aerobic microorganisms were mainly identified using a MicroScan WalkAway system (Siemens Healthcare Diagnostics, IL, USA) and a RapID ANA II (Thermo Fisher SCIENTICIC, UK) while anaerobic bacteria were mainly identified using various latex agglutination and biochemical spot tests.

However, specific identification methods were performed in some bacterial species.

INDUSTRIAL APPLICABILITY

The improved Tm mapping method using seven IMLL probes of the disclosure can accurately distinguish among and identify microorganisms at least at the genus level and often at the species level even in a real-time PCR instrument having measurement errors of Tm values between PCR tubes within ±0.5° C.

Therefore, since the Tm mapping method can be performed in almost all real-time PCR instruments, it is expected that the present test method that can identify unspecified infection-causing pathogenic microorganisms in about 4 hours after sample collection will be widely spread.

SEQUENCE LISTING

This application contains references to amino acid sequences and/or nucleic acid sequences which have been submitted concurrently herewith as the sequence listing text file entitled "000057usco_sequencelisting.TXT", file size 17.2 KiloBytes (KB), created on Dec. 20, 2022. The aforementioned sequence listing is hereby incorporated by reference in its entirety pursuant to 37 C.F.R. § 1.52(e)(5)

Although only some embodiments of the present disclosure have been described in detail above, those skilled in the art will readily appreciate that many modifications are possible in the embodiments without materially departing from the novel teachings and advantages of this disclosure. Accordingly, all such modifications are intended to be included within scope of this disclosure.

What is claimed is:

1. A method of identifying an infection-causing pathogenic microorganism, comprising the following steps (1) to (5):
   (1) extracting a microbial DNA from a blood sample;
   (2) performing nested PCR using the extracted microbial DNA, as a template, and a plurality of bacterial universal primers;
   (3) adding imperfect-match linear long probes (IMLL probes) to the gene amplified products to analyze melting temperature (Tm) values of the IMLL probes;
   (4) two-dimensionally mapping the Tm values of the plurality of IMLL probes to form a shape thereof; and
   (5) checking the two-dimensionally mapped "shape" against a database to identify the infection-causing pathogenic microorganism, wherein the two-dimensional mapping comprises the step of plotting points for seven IMLL probes when the SEQ ID NOs. of IMLL probes are set as the X axis and the Tm values when using the IMLL probes are set as the Y axis, wherein the "shape" of the two-dimensional mapping refers to the shape formed by connecting the points plotted for the seven IMLL probes with lines;

wherein the database consists of a two-dimensional mapping of the Tm values when the seven IMLL probes are used for the bacterial DNAs from 145 bacterial species; and wherein the 145 bacterial species are selected from the group consisting of *Achromobacter xylosoxidans, Acinetobacter baumanii, Acinetobacter calcoaceticus, Aeromonas hydrophila, Alistipes onderdonkii, Anaerococcus vaginalis, Arthrobacter cumminsii, Bacillus cereus, Bacillus coagulans, Bacillus licheniformis, Bacillus megaterium, Bacillus pumilus, Bacillus subtilis* subsp. *Subtilis, Bacteroides dorei, Bacteroides finegoldii, Bacteroides fragilis, Bacteroides nordii, Bacteroides salyersiae, Bacteroides thetaiotaomicron, Bacteroides uniformis, Bacteroides vulgatus, Bartonella henselae, Bifidobacterium bifidum, Bilophila wadsworthia, Bordetella pertussis, Borrelia burgdorferi, Brevibacillus laterosporus, Campylobacter coli, Campylobacter jejuni* subsp. *jejuni, Campylobacter rectus, Capnocytophaga gingivalis, Capnocytophaga granulosa, Capnocytophaga haemolytica, Capnocytophaga ochracea, Capnocytophaga sputigena, Chryseobacterium gleum, Citrobacter amalonaticus, Citrobacter freundii, Clostridium difficile, Clostridium histolyticum, Clostridium hylemonae, Clostridium paraputrificum, Clostridium perfringus, Clostridium sporogenes, Clostridium subterminal, Clostridium tertium, Corynebacterium amycolatum, Corynebacterium macginleyi, Corynebacterium striatum, Corynebacterium xerosis, Eggerthella lenta, Eikenella corrodens, Empedobacter brevis, Enterobacter aerogenes, Enterobacter cloacae* subsp. *cloacae, Enterococcus avium, Enterococcus casseliflavus, Enterococcus durans, Enterococcus faecalis, Enterococcus faecium, Enterococcus gallinarum, Enterococcus raffinosus, Escherichia albertii, Escherichia coli, Eubacterium limosum, Finegoldia magna, Fusobacterium necrophorum, Fusobacterium periodonticum, Fusobacterium varium, Gardnerella vaginalis, Gemella morbillorum, Geobacillus stearothermophilus, Haemophilus influenzae, Halmonas venusta, Klebsiella oxytoca, Klebsiella pneumoniae, Kocuria rosea, Lactobacillus acidophilus, Lactobacillus crispatus, Lactobacillus fermentum, Lactobacillus jensenii, Lactococcus garvieae, Legionella pneumophila* subsp. *pneumophila, Leptospira interrogans serovar Copenhageni, Listeria monocytogenes, Micrococcus luteus, Morganella morganii, Nocardia cyriacigeorgica, Odoribacter splanchinicus, Pantoea agglomerans, Parvimonas micra, Pasteurella multocida, Peptoniphilus asaccharolyticus, Peptoniphilus gorbachii, Peptostreptococcus anaerobius, Plesiomonas shigelloides, Porphyromonas gingivalis, Prevotella corporis, Prevotella intermedia, Prevotella melaninogenica, Prevotella timonensis, Prevotella veronalis, Propionibacterium acnes, Propionibacterium granulosum, Proteus mirabilis, Proteus vulgaris, Pseudomonas aeruginosa, Pseudomonas fluorescens, Pseudomonas putida, Salmonella enterica, Serratia marcescens, Serratia plymuthia, Staphylococcus aureus, Staphylococcus capitis/epidermidis, Staphylococcus cohnii, Staphylococcus haemolyticus, Staphylococcus hominis, Staphylococcus intermedius, Staphylococcus lugdunensis, Staphylococcus saprophyticus* subsp. *saprophyticus, Staphylococcus schleiferi* subsp. *coagulans, Staphylococcus simulans, Staphylococcus warneri, Stenotrophomonas maltophilia, Streptobacillus moniliformis, Streptococcus agalactiae, Streptococcus anginosus, Streptococcus bovis, Streptococcus constellatus, Streptococcus dysgalactiae, Streptococcus gallolyticus* subsp. *pasteurianus, Streptococcus gordonii, Streptococcus intermedius, Streptococcus mitis, Streptococcus orali, Streptococcus pneumoniae, Streptococcus pyogenes, Streptococcus salivarius, Streptococcus sanguinis, Tannerella forsythus, Treponema denticola, Vibrio fluvialis, Vibrio vulnificus, Yersinia enterocolitica* subsp. *enterocolitica, Yersinia pseudotuberculosis.*

2. The method of identifying an infection-causing pathogenic microorganism according to claim 1, wherein the performing nested PCR using the plurality of bacterial universal primers in the step (2) consists of a plurality of steps.

3. The method of identifying an infection-causing pathogenic microorganism according to claim 1, wherein the imperfect-match linear long probe in the step (3) consists of 35 to 50 bases, and a difference in Tm values of the probe that reflects a difference in bacterial species, due to the number and position of mismatches is larger than a difference in Tm values of the gene amplified products.

4. The method of identifying an infection-causing pathogenic microorganism according to claim 2, wherein the imperfect-match linear long probe in the step (3) consists of 35 to 50 bases, and a difference in Tm values of the probe that reflects a difference in bacterial species, due to the number and position of mismatches is larger than a difference in Tm values of the gene amplified products.

5. The method of identifying an infection-causing pathogenic microorganism according to claim 3, wherein the difference in Tm values that reflects the difference in the bacterial species is up to 20° C. among bacterial species.

6. The method of identifying an infection-causing pathogenic microorganism according to claim 4, wherein the difference in Tm values that reflects the difference in the bacterial species is up to 20° C. among bacterial species.

7. An imperfect-match linear long probe having any base sequence selected from the group consisting of SEQ ID NOs: 1 to 7 and 21 to 34, the probe having 35 to 50 bases and Tm value for each bacterial species depending on the number and position of mismatches, the largely different Tm value having a difference up to 20° C. among bacterial species.

* * * * *